US008252757B2

(12) United States Patent
Hessel et al.

(10) Patent No.: US 8,252,757 B2
(45) Date of Patent: Aug. 28, 2012

(54) LONG TERM DISEASE MODIFICATION USING IMMUNOSTIMULATORY OLIGONUCLEOTIDES

(75) Inventors: Edith M. Hessel, San Francisco, CA (US); Robert L. Coffman, Portola Valley, CA (US)

(73) Assignee: Dynavax Technologies Corporation, Berkeley, CA (US)

( * ) Notice: Subject to any disclaimer, the term of this patent is extended or adjusted under 35 U.S.C. 154(b) by 729 days.

(21) Appl. No.: 11/938,192

(22) Filed: Nov. 9, 2007

(65) Prior Publication Data
US 2009/0068208 A1 Mar. 12, 2009

Related U.S. Application Data

(60) Provisional application No. 60/865,089, filed on Nov. 9, 2006.

(51) Int. Cl.
*C12N 15/11* (2006.01)
*C07H 21/02* (2006.01)
(52) U.S. Cl. .................................... 514/44 R; 536/23.1
(58) Field of Classification Search ................ 514/44 R; 536/23.1
See application file for complete search history.

(56) References Cited

U.S. PATENT DOCUMENTS

| | | | |
|---|---|---|---|
| 4,458,066 A | 7/1984 | Caruthers et al. | |
| 4,650,675 A | 3/1987 | Borel et al. | |
| 4,849,513 A | 7/1989 | Smith et al. | |
| 4,910,300 A | 3/1990 | Urdea et al. | |
| 4,948,882 A | 8/1990 | Ruth | |
| 5,015,733 A | 5/1991 | Smith et al. | |
| 5,093,232 A | 3/1992 | Urdea et al. | |
| 5,118,800 A | 6/1992 | Smith et al. | |
| 5,118,802 A | 6/1992 | Smith et al. | |
| 5,124,246 A | 6/1992 | Urdea et al. | |
| 5,391,723 A | 2/1995 | Priest | |
| 5,453,496 A | 9/1995 | Caruthers et al. | |
| 5,460,831 A | 10/1995 | Kossovsky et al. | |
| 5,552,391 A | 9/1996 | Coutts et al. | |
| 6,194,388 B1 | 2/2001 | Krieg et al. | |
| 6,207,646 B1 | 3/2001 | Krieg et al. | |
| 6,498,148 B1 | 12/2002 | Raz | |
| 6,610,661 B1 | 8/2003 | Carson et al. | |
| 7,585,847 B2 * | 9/2009 | Bratzler et al. ............. | 514/44 R |
| 2004/0132677 A1 | 7/2004 | Fearon et al. | |
| 2006/0058254 A1 | 3/2006 | Dina et al. | |
| 2009/0017075 A1 | 1/2009 | Van Nest et al. | |

FOREIGN PATENT DOCUMENTS

| | | |
|---|---|---|
| WO | WO-97/28259 A1 | 8/1997 |
| WO | WO-98/16247 A1 | 4/1998 |
| WO | WO-98/55495 A2 | 12/1998 |
| WO | WO-98/55495 A3 | 12/1998 |
| WO | WO-99/11275 A2 | 3/1999 |
| WO | WO-99/11275 A3 | 3/1999 |
| WO | WO-99/62923 A2 | 12/1999 |
| WO | WO-99/62923 A3 | 12/1999 |
| WO | WO-00/61151 A2 | 10/2000 |
| WO | WO-00/61151 A3 | 10/2000 |
| WO | WO-2004/058179 A2 | 7/2004 |
| WO | WO-2004/058179 A3 | 7/2004 |
| WO | WO-2006/096497 A2 | 9/2006 |
| WO | WO-2006/096497 A3 | 9/2006 |
| WO | WO-2008/073661 A2 | 6/2008 |
| WO | WO-2008/073661 A3 | 6/2008 |

OTHER PUBLICATIONS

Tulic et al. Amb a 1-immunostimulatory oligodeoxynucleotide conjugate immunotherapy decreases the nasal inflammatory response. J Allergy Clin Immunol, 2004, vol. 113, 235-241.*
Tulic et al 2004 American Academy Allergy Asthma and Immunology pp. 235-241.*
Agrawal, S. ed. (1993). "Protocols for Oligonucletoides and Analogs: Synthesis and Properties," in *Methods in Molecular Biology*, vol. 20, Humana Press, Inc.: Totowa, New Jersey, 1 page, (Table of Contents Only.).
Aramaki, Y. et al. (1995). "Interferon-γ Inductive Effect of Liposomes as an Immunoadjuvant," *Vaccine* 13(18):1809-1814.
Arky, R. et al. (1998). *Physicians Desk Reference*, 52$^{nd}$ Edition, Medical Economics Company, Inc.: Montvale, NJ, 1 page, (Table of Contents Only.).
Arruda, L.K. et al. (Aug. 15, 1997). "Induction of IgE Antibody Responses by Glutathione S-Transferase from the German Cockroach (*Blattella germanica*)," *J. Biol. Chem.* 272(33):20907-20912.
Asanuma, H. et al. (Jan. 1995). "Cross-Protection Against Influenza Virus Infection in Mice Vaccinated by Combined Nasal/Subcutaneous Administration," *Vaccine* 13(1):3-5.
Asturias, J.A. et al. (1997). "Cloning and High Level Expression of *Cynodon dactylon* (Bermuda Grass) Pollen Profilin (Cyn d 12) in *Escherichia coli*: Purification and Characterization of the Allergen," *Clin. Exp. Allergy.* 27:1307-1313.
Asturias, J.A. et al. (1998). "Sequencing and High Level Expression in *Escherichia coli* of the Tropomyosin Allergen (Der p 10) from *Dermatophagoides pteronyssinus*," *Biochim. Biophys. Acta.* 1397:27-30.
Astwood, J.D. et al. (1996). "Molecular Characterization of *Hor v* 9: Conservation of a T-Cell Epitope Among Group IX Pollen Allergens and Human VCAM and CD2," Chapter 39 in *New Horizons in Allergy Immunotherapy*, Sehon et al. eds., Plenum Press: New York, NY, pp. 269-277.
Atherton, E. et al. (Jul. 1981). "Synthesis of a 21-Residue Fragment of Human Proinsulin by the Polyamide Solid Phase Method," *Hoppe-Seyler's Z. Physiol. Chem.* 362:833-839.
Ausubel, F.M. et al., eds. (1995). *Current Protocols in Molecular Biology*, vol. 1, John Wiley & Sons, Inc., pp. iii-xii (Table of Contents Only.)
Ballas, Z.K. et al. (1996). "Induction of NK Activity in Murine and Human Cells by CpG Motifs in Oligodeoxynucleotides and Bacterial DNA," *J. Immunol.* 157:1840-1845.
Banerjee, B. et al. (Jun. 1997). "Purification of a Major Allergen, Asp f 2 Binding to IgE in Allergic Bronchopulmonary Aspergillosis, from Culture Filtrate of *Aspergillus fumigatus*," *J. Allergy. Clin. Immunol.* 99(6-Part 1):821-827.
Bartolomé, B. et al. (1997). "Allergens from Brazil Nut: Immunochemical Characterization," *Allergol. Et Immunopathol.* 25(3):135-144.
Beaucage, S.L. (1993). "Oligodeoxyribonucleotide Synthesis," Chapter 3 in *Protocols for Oligonucleotides and Analogs: Synthesis and Properties*, Agrawal, S. ed., Humana Press: Totowa, NJ, 20:33-61.

(Continued)

*Primary Examiner* — Nita M Minnifield
*Assistant Examiner* — Nina Archie
(74) *Attorney, Agent, or Firm* — Morrison & Foerster LLP

(57) ABSTRACT

The invention provides methods for treating asthma by using multiple rounds of administration of ISS over a period of time to confer long term disease modification.

28 Claims, 8 Drawing Sheets

OTHER PUBLICATIONS

Beaucage, S.L. et al. eds. (2009). *Current Protocols in Nucleic Acid Chemistry*, vols. 1-3, John Wiley & Sons, Inc.: New York, NY, 17 pages. (Table of Contents Only.).

Ben Ahmeida, E.T.S. et al. (1993). "Immunopotentiation of Local and Systemic Humoral Immune Responses by ISCOMs, Liposomes and FCA: Role in Protection Against Influenza A in Mice," *Vaccine* 11(13):1302-1309.

Benoit, R. et al. (1987). "Peptides. Strategies for Antibody Production and Radioimmunoassays," Chapter 6 in *Neuromethods*, Boulton, A.A. et al., eds., Humana Press: Clifton, NJ, pp. 43-72.

Borel, H. et al. (1990). "A Novel Technique to Link Either Proteins or Peptides to Gammaglobulin to Construct Tolerogens," *Journal of Immunological Methods* 126:159-168.

Borel, Y. et al. (1995). "Food Allergens Transformed Into Tolerogens," *Int. Arch. Allergy. Immunol.* 107:264-267.

Borel, Y. et al. (1996). "Parenteral and Oral Administation of Tolerogens: Protein-IgG Conjugates," *Oral Tolerance: Mechanisms and Applications in Ann. N.Y. Acad. Sci.*, 778:80-87.

Boujrad, N. et al. (Jun. 1993). "Inhibition of Hormone-Stimulated Steroidogenesis in Cultured Leydig Tumor Cells by a Cholesterol-Linked Phosphorothioate Oligodeoxynucleotide Antisense to Diazepam-Binding Inhibitor," *PNAS USA* 90:5728-5731.

Bousquet, Y. et al. (1999). "Molecular Mechanisms of the Adsorption of a Model Protein (Human Serum Albumin) on Poly(Methylidene Malonate 2.1.2) Nanoparticles," *Pharm. Res.* 16(1):141-147.

Braun, R.P. et al. (Sep. 1988). "Immunogenic Duplex Nucleic Acids are Nuclease Resistant," *J. Immunol.* 141(6):2084-2089.

Breiteneder, H. et al. (1989). "The Gene Coding for the Major Birch Pollen Allergen *BetvI*, is Highly Homologous to a Pea Disease Resistance Response Gene," *EMBO J.* 8(7):1935-1938.

Breitwieser, A. et al. (Nov. 1996). "2-D Protein Crystals as an Immobilization Matrix for Producing Reaction Zones in Dipstick-Style Immunoassays," *Biotechniques* 21(5):918-925.

Broide, D. et al. (1998). "Immunostimulatory DNA Sequences Inhibit IL-5, Eosinophilic Inflammation, and Airway Hyper-responsiveness in Mice," *J. Immunol.* 161:7054-7062.

Bufe, A. et al. (1998). "Allergenic Activity of a Major Grass Pollen Allergen is Elevated in the Presence of Nasal Secretion," *Am. J. Respir. Crit. Care Med.* 157:1269-1276.

Burks, A.W. et al. (1995). "Isolation, Identification, and Characterization of Clones Encoding Antigens Responsible for Peanut Hypersensitivity," *Int. Arch. Allergy Immunol.* 107:248-250.

Burks, A.W. et al. (Oct. 1995). "Recombination Peanut Allergen *Ara h* I Expression and IgE Binding in Patients with Peanut Hypersensitivity," *J. Clin. Invest.* 96:1715-1721.

Caraballo, L. et al. (1996). "HLA-DR3 is Associated with the IgE Immune Responsiveness to a Recombinant Allergen from *Blomia tropicalis* (BT)," Chapter 11 in *New Horizons in Allergy Immunotherapy*, Sehon etl al. eds., Plenum Press: New York, NY, pp. 81-83.

Casale, T.B. et al. (Jul. 1997). "Use of an Anti-IgE Humanized Monoclonal Antibody in Ragweed-Induced Allergic Rhinitis," *J Allergy Clin Immunol*, 100(1):110-121.

Chang, S-F. et al. (1992). "Nasal Drug Delivery," Chapter 9 in *Treatise on Controlled Drug Delivery*, Kydonieus, A. ed, Marcel Dekker, Inc.: New York, NY, pp. 423-463.

Chatel, J-M. et al. (1996). "Expression, Purification and Immunochemical Characterization of Recombinant Bovine Beta-Lactoglobulin, A Major Cow Milk Allergen ," *Mol. Immunol.* 33(14):1113-1118.

Chaturvedi, S. et al. (1996). "Stabilization of Triple-Stranded Oligonucleotide Complexes: Use of Probes Containing Alternating Phosphodiester and Stereo-Uniform Cationic Phosphoramidate Linkages," *Nucleic Acids Res.* 24(12):2318-2323.

Chavany, C. et al. (1992). "Polyalkylcyanoacrylate Nanoparticles as Polymeric Carriers for Antisense Oligonucleotides," *Pharm. Res.* 9(4):441-449.

Chavany, C. et al. (1994). "Adsorption of Oligonucleotides onto Polyisohexylcyanoacrylate Nanoparticles Protects Them Against Nucleases and Increases Their Cellular Uptake," *Pharm. Res.* 11(9):1370-1378.

Chen, Z. et al. (1999). "Enhanced Protection Against a Lethal Influenza Virus Challenge by Immunization with Both Hemagglutinin- and Neuraminidase-Expressing DNAs," *Vaccine* 17:653-659.

Cho, J.Y. et al. (2004, e-pub. Nov. 14, 2003). "Immunostimulatory DNA Inhibits Transforming Growth Factor-β Expression and Airway Remodeling," *Am. J. Respir. Cell Mol. Biol.* 30:651-661.

Cho, J.Y. et al. (2006). "Remodeling Associated Expression of Matrix Metalloproteinase 9 But Not Tissue Inhibitor of Metalloproteinase 1 in Airway Epithelium: Modulation by Immunostimulatory DNA," *J. Allergy Clin. Immunol.* 117(3):618-625.

Chua, K.Y. et al. (Jan. 1988). "Sequence Analysis of cDNA Coding for a Major House Dust Mite Allergen, *Der p* 1: Homology with Cysteine Proteases," *J. Exp. Med.* 167:175-182.

Chua, K.Y. et al. (1990). "Expression of *Dermatophagoides pteronyssinus* Allergen, *Der p* II, in *Escherichia coli* and the Binding Studies with Human IgE," *Int. Arch. Allergy Appl. Immunol.* 91:124-129.

Coligan, J.E. et al. eds. (1992). *Current Protocols in Immunology*, vol. 1, John Wiley & Sons, Inc, pp. 1-9, (Table of Contents Only.).

Cooke, S.K. et al. (1997). "Allergenic Properties of Ovomucoid in Man," *J. Immunol.* 159:2026-2032.

Corey, D.R. et al. (Dec. 4, 1987). "Generation of a Hybrid Sequence-Specific Single-Stranded Deoxyribonuclease," *Science* 238:1401-1403.

Cowdery, J.S. et al. (1996). "Bacterial DNA Induces NK Cells to Produce IFN-γ in Vivo and Increases the Toxicity of Lipopolysaccharides," *J. Immunol.* 156:4570-4575.

Crameri, R. et al. (1996). "Automated Serology with Recombinant Allergens: A Feasibility Studay," Chapter 15 in *New Horizons in Allergy Immunotherapy*, Sehon et al. eds., Plenum Press: New York, NY, pp. 111-116.

Crameri, R. et al. (Sep. 1997). "Molecular Aspects and Diagnostic Value of Fungal Allergens," *Mycoses* 41(Suppl 1):56-60; English Language Summary Only.

Crameri, R. (1998). "Recombinant *Aspergillus fumigatus* Allergen: From the Nucleotide Sequences to Clinical Applications," *Int. Arch. Allergy. Immunol* 115:99-114.

Detmar, U. et al. (1989). "Allergy of Delayed Type to Recombinant Interferon α 2c," *Contact Dermatitis* 20:149-150.

Donovan, G.R. et al. (1993). "Immunoaffinity Analysis of Cross-Reacting Allergens by Protein Blotting," *Electrophoresis* 14:917-922.

Douglas, S. J. et al. (1987). "Nanoparticles in Drug Delivery," *Crit. Rev. Ther. Drug. Carrier Syst.* 3(3):233-261.

Dumas, V. et al. (1995). "Induction of Tolerance by Administration of Hapten-Immunoglobulin Conjugates is Associated with Decreased IL-2 and IL-4 Production," *Arch. Dermatol. Res.* 287:123-128.

Eckstein, F. ed. (1991). *Oligonucleotides and Analogues: A Practical Approach*, Oxford University Press: New York, NY, pp. ix-xvii, (Table of Contents Only.).

Elsayed, S. et al. (1991). "The Structural Requirements of Epitopes with IgE Binding Capacity Demonstrated by Three Major Allergens from Fish, Egg and Tree Pollen," *Scand. J. Clin. Lab. Invest.* 51(Suppl. 204):17-31.

Eriksson, T.L.J. et al.(Jan. 1998). "Cloning and Characterisation of a Group II Allergen from the Dust Mite *Tyrophagus putrescentiae*," *Eur. J. Biochem.* 251(1/2):443-447.

Fanucchi, M.V. et al. (2004). "Immunostimulatory Oligonucleotides Attenuate Airways Remodeling in Allergic Monkeys," *Am. J. Respis. Crit. Care Med.* 170:1153-1157.

Ferentz, A.E.. et al. (May 8, 1991). "Disulfide Cross-Linked Oligonucleotides," *J. Am. Chem. Soc.* 113(10):4000-4002.

Ferentz, A.E. et al. (Oct. 6, 1993). "Synthesis and Characterization of Disulfide Cross-Linked Oligonucleotides," *J. Am. Chem. Soc.* 115(20):9006-9014.

Förster, E. et al. (Jun. 1995). "Natural and Recombinant Enzymatically Active or Inactive Bee Venom Phospholipase $A_2$ has the Same Potency to Release Histamine from Basophils in Patients with Hymenoptera Allergy," *J. Allergy Clin. Immunol.* 95:1229-1235.

Fraley, R. et al. (Mar. 1981). "New Generation Liposomes: The Engineering of an Efficient Vehicle for Intracellular Delivery of Nucleic Acids" *Trends in Biochem. Sci.* 6:77-80.

Freshney, R.I. ed. (1986). *Animal Cell Culture: A Practical Approach*, IRL Press: Oxford, England, pp. vii-xii, (Table of Contents Only.).

Fuchs, T. et al. (1997). "Natural Latex, Grass Pollen, and Weed Pollen Share IgE Epitopes," *J. Allergy. Clin. Immunol.* 100(3):356-364.

Gait, M.J. ed. (1984). *Oligonucleotide Synthesis: A Practical Approach*, IRL Press: New York, NY, pp. vii-xii, (Table of Contents Only.).

Galland, A.V. et al. (1998). "Purification of a 41 kDa Cod-Allergenic Protein," *J. Chromatogr. B.* 706:63-71.

Ganz, M.A. et al. (1990). "Resistance and Allergy to Recombinant Human Insulin," *J. Allergy. Clin. Immunol.* 86(1):45-51.

Gao, H. et al. (1995). "Circularization of Oligonucleotides by Disulfide Bridge Formation," *Nucleic Acids Res.* 23(11):2025-2029.

Gauvreau, G.M. et al. (Jul. 1, 2006, e-pub. Match 30, 2006). "Immunostimulatory Sequences Regulate Interferon-Inducible Genes but not Allergic Airway Responses," *American Journal of Respiratory and Critical Care Medicine* 174(1):15-20.

Geoghegan, K.F. et al. (1992). "Site-Directed Conjugation of Nonpeptide Groups to Peptides and Proteins Via Periodate Oxidation of a 2-Amino Alcohol. Application to Modification at N-Terminal Serine," *Bioconjug. Chem.* 3(2):138-146.

Glick, G.D. (Oct. 11, 1991). "Synthesis of Conformationally Restricted DNA Hairpin," *J. Org. Chem.* 56(24):6746-6747.

Glick, G.D. et al. (Jun. 17, 1992). "Trapping and Isolation of an Alternate DNA Conformation," *J. Am. Chem. Soc.* 114(13):5447-5448.

Godard, G. et al. (1995). "Antisense Effects of Cholesterol-Oligodeoxynucleotide Conjugates Associated with Poly(Alkylcyanoacrylate) Nanoparticles," *Eur. J. Biochem.* 232:404-410.

González De La Peña, M.A. et al. (Jan. 29, 1993). "Cloning and Expression of the Major Allergen From Yellow Mustard Seeds, *Sin a* I," *Biochem. Bioph. Res Comm.* 190(2):648-653.

Gonzalo, M.A. et al. (1998). "Cutaneous Allergy to Human (Recombinant DNA) Insulin," *Allergy Net* 53:106-107.

Goodchild, J. (May/Jun. 1990). "Conjugates of Oligonucleotides and Modified Oligonucleotides: A Review of Their Synthesis and Properties," *Bioconjug. Chem.* 1(3):165-187.

Goodwin, J.T. et al. (1994). "Synthesis of a Disulfide Stabilized RNA Hairpin," *Tetrahedron Letters* 35(11):1647-1650.

Govorkova, E.A. et al. (1997). "Cross-Protection of Mice Immunized with Different Influenza A (H2) Strains and Challenged with Viruses of the Same HA Subtype," *Acta Virol.* 41:251-257.

Grabarek, Z. et al. (1990). "Zero-Length Crosslinking Procedure with the Use of Active Esters," *Anal. Biochem.* 185:131-135.

Grammer, L.C. et al. (Feb. 1987). "Specificity of Immunoglobulin E and Immunoglobulin G Against Human (Recombinant DNA) Insulin in Human Insulin Allergy and Resistance," *J. Lab Clin. Med.* 109:141-146.

Granoff, D.M. et al. (1993). "Effect of Immunity to the Carrier Protein on Antibody Responses to *Haemophilus influenzae* Type B Conjugate Vaccines," *Vaccine* 11(Suppl. 1):S46-551.

Graul, A.I. (2002). "Respiratory Drug Development Compendium 2002," *Drugs of the Future* 27(12):1181-1194.

Gregoire, C. et al. (Dec. 20, 1996). "cDNA Cloning and Sequencing Reveal the Major Horse Allergen Equ c1 to Be a Glycoprotein Member of the Lipocalin Superfamily," *J. Biol. Chem.* 271(51):32951-32959.

Hagiwara, A. et al. (1987). "A New Drug-Delivery-System of Anticancer Agents: Activated Carbon Particles Adsorbing Anticancer Agents," *In Vivo* 1:241-252.

Hakkaart, G.A.J. et al. (1998). "Expression of the House Dust Mite Allergen Der p 2 in the Baker's Yeast *Saccharomyces cerevisiae*," *Clin. Exp. Allergy* 28:45-52.

Hakkaart, G.A.J. et al. (1998). "Immune-Reactivity of Recombinant Isoforms of the Major Dust Mite Allergen Der p2," *Clin. Exp. Allergy* 28:169-174.

Hakkaart, G.A.J. et al. (1998). "Involvement of the N-Terminus of Der p 2 in IgE and Monoclonal Antibody Binding," *In. Arch. Allergy Immunol.* 115:150-156.

Hames, B.D. et al. eds. (1984). *Transcription and Translation: A Practical Approach*, IRL Press:Oxford, England, pp. vii-xiv (Table of Contents.).

Haralambidis, J. et al. (1990). "The Synthesis of Polyamide-Oligonucleotide Conjugate Molecules," *Nucleic Acids Res.* 18(3):493-499.

Haralambidis, J. et al. (1990). "The Preparation of Polyamide-Oligonucleotide Probes Containing Multiple Non-Radioactive Labels," *Nucleic Acids Res.* 18(3):501-505.

Harlow, E. et al. (1988). *Antibodies, A Laboratory Manual*, Cold Spring Harbor Laboratory: Cold Spring Harbor, NY, pp. iii-ix, (Table of Contents Only.).

Harlow, E. et al. (1999). *Using Antibodies: A Laboratory Manual*, Cold Spring Harbor Laboratory Press: Cold Spring Harbor, NY, 3 pages, (Table of Contents Only.).

Hedlin, G. (Dec. 1995). "The Role of Immunotherapy in Pediatric Allergic Disease," *Curr. Opin. Pediatr.* 7(6):676-682.

Heiss, S. et al. (1996). "Expression of Zm13, a Pollen Specific Maize Protein, in *Escherichia coli* Reveals IgE-Binding Capacity and Allergenic Potential," *FEBS Lett.* 381:217-221.

Helm, R. et al. (Jul. 1996). "Isolation and Characterization of a Clone Encoding a Major Allergen (*Bla g* Bd90K) Invloved in IgE-Mediated Cockroach Hypersensitivity," *J. Allergy Clin. Immunol.* 98(1):172-180.

Hemmann, S. et al. (1998). "Differential IgE Recognition of Recombinant *Aspergillus fumigatus* Allergens by Cystic Fibrosis Patients with Allergic Bronchopulmonary Aspergillosis or *Aspergillus* Allergy," *Eur. J. Immunol.* 28:1155-1160.

Hermanson, G.T. ed. (1996). *Bioconjugate Techniques*, Academic Press, Inc.: San Diego, CA, pp. ix-xx, (Table of Contents Only.).

Hessel, E.M. et al. (Dec. 5, 2005). "Immunostimulatory Oligonucleotides Block Allergic Airway Inflammation by Inhibiting Th2 Cell Activation and IgE-Mediated Cytokine Induction," *The Journal of Experimental Medicine* 202(11):1563-1573.

Hirschwehr, R. et al. (Feb. 1998). "Allergens, IgE, Mediators, Inflammatory Mechanisms," *J. Allergy Clin. Immunol.* 101(2-Part 1):196-206.

Hoffmann, A. et al. (Feb. 1997). "Biologic Allergen Assay for in Vivo Test Allergens with an In Vitro Model of the Murine Type 1 Reaction," *J. Allergy. Clin. Immunol.* 99(2):227-232.

Ikeda, R.K. et al. (2003). "Accumulation of Peribronchial Mast Cells in a Mouse Model of Ovalbumin Allergen Induced Chronic Airway Inflammation: Modulation by Immunostimulatory DNA Sequences," *The Journal of Immunology* 171:4860-4867.

Jäger, A. et al. (1988). "Oligonucleotide N-Alkylphosphoramidates: Synthesis and Binding to Polynucleotides," *Biochem.* 27(19):7237-7246.

Jahn-Schmid, B. et al. (1996). "Immunoreactivity of Allergen (Bet v 1) Conjugated to Crystalline Bacterial Cell Surface Layers (S-Layers)," *Immunotechnology* 2:103-113.

Kandimalla, E.R. et al. (2001). "Effect of Chemical Modifications of Cytosine and Guanine in a CpG-Motif of Oligonucleotides: Structure-Immunostimulatory Activity Relationships," *Bioorg. Med. Chem.* 9:807-813.

Kendrew, J. ed. (1994). *The Encyclopedia of Molecular Biology*, Blackwell Science:Cambridge, MA, pp. vi-viii (Table of Contents Only.).

Kessler, C. (Dec. 1992). "Nonradioactive Labeling Methods for Nucleic Acids," Chapter 2 in *Nonisotopic DNA Probe Techniques*, Kricka, L.J. ed., Academic Press, Inc., pp. 29-92.

Kikuta, K. et al. (Dec. 1990). "Cross-Protection Against Influenza B Type Virus Infection by Intranasal Inoculation of the HA Vaccines Combined with Cholera Toxin B Subunit," *Vaccine* 8(6):595-599.

King, T.P. et al. (Sep. 1996). "Yellow Jacket Venom Allergens, Hyaluronidase and Phospholipase: Sequences Similarity and Antigenic Cross-Reactivity with their Hornet and Wasp Homologs and Possible Implications for Clinical Allergy," *J. Allergy Clin. Immunol.* 98(3):588-600.

Kingetsu, I. et al. (2000). "Common Antigenicity between Japanese Cedar (*Ctyptomeria japonica*) Pollen and Japanese Cypress (*Chamaecyparis obtusa*) Pollen, I. H-2 Complex Affects Cross Responsiveness to Cry j 1 and Cha o 1 at the T- and B-cell Level in Mice," *Immunol.* 99:625-629.

Klinman, D.M. et al. (1997). "Contribution of CpG Motifs to the Immunogenicity of DNA Vaccines," *J. Immunol.* 158:3635-3639.

Kodihalli, S. et al. (May 1997). "Cross-Protection Among Lethal H5N2 Influenza Viruses Induced by DNA Vaccine to the Hemagglutinin," *J. Virol.* 71(5):3391-3396.

Konieczny, A. et al. (Dec. 1997). "The Major Dog Allergens, *Can f* 1 and *Can f* 2 are Salivary Lipocalin Proteins: Cloning and Immunological Characterization of the Recombinant Forms," *Immunology* 92(4):577-586.

Krieg, A.M. et al. (Apr. 8, 1995). "CpG Motifs in Bacterial DNA Trigger Direct B-Cell Activation," *Nature* 374:546-549.

Kuiken, C. et al. eds. (2000). *HIV Sequence Compendium 2000*, Theoretical Biology and Biophysics: Los Alamos, New Mexico, 1 page, (Table of Contents Only.).

Kullmann, W. (1997). *Enzymatic Peptide Synthesis*, CRC Press, Inc. Boca Raton, FL, 3 pages (Table of Contents Only.).

Lambert, G. et al. (1998) "Effect of Polyisobutylcyanoacrylate Nanoparticles and Lipofectin® Loaded with Oligonucleotides on Cell Viability and PKCα Neosynthesis in HepG2 Cells," *Biochimie* 80:969-976.

Lasic, D.D. (1993). *Liposomes: From Physics to Applications*, Elsevier, Amsterdam: pp. xi-xviii (Table of Contents Only.).

Latimer, L.J.P. et al. (1995). "Specificity of Monoclonal Antibodies Produced Against Phosphorothioate and Ribo Modified DNAs," *Mol. Immunol.* 32(14/15)1057-1064.

Lea, I.A. et al., (1996). "Cloning and Sequencing of cDNAs Encoding the Human Sperm Protein, Sp17," *Biochim. et Biophys. Acta* 1307:263-266.

Lee, S.Y. et al. Mar. (2006). "Immunostimulatory DNA Inhibits Allergen-Induced Peribronchial Angiogenesis in Mice," *J. Allergy Clin. Immunol.* 117(3):597-603.

Lehrer, S.B. et al. (1996). "Why are Some Proteins Allergenic? Implications for Biotechnology," *Crit. Rev. Food Sci. Nutr.* 36(6):553-564.

Lehrer, S.B. et al. (1997). "Recombinant Proteins in Newly Developed Foods: Identification of Allergenic Activity," *Int. Arch. Allergy Immunol.* 113:122-124.

Leung, P.S.C. et al. (Nov. 1996). "IgE Reactivity Against a Cross-Reactive Allergen in Crustacea and Mollusca: Evidence for Tropomyosin as the Common Allergen," *J. Allergy Clin. Iummunol.* 98(5-Part 1):954-961.

Leung, P.S.C. et al. (1998). "Molecular Identification of the Lobster Muscle Protein in Tropomyosin as a Seafood Allergen," *Mol. Mar. Biol. Biotechnol* 7(1):12-20.

Lipford, G.B. et al. (1997). "CpG-Containing Synthetic Oligonucleotides Promote B and Cytotoxic T Cell Responses to Protein Antigen: A New Class of Vaccine Adjuvants," *Eur. J. Immunol.* 27:2340-2344.

Lynch, N.R. et al. (Apr. 1998). "Association Between Allergic Disease and Reactivity to Recombinant Der p 2 Allergen of House Dust Mites in a Tropical Situation," *J. Allergy Clin. Immunol.* 101(4-Part 1):562-564.

Maniatis, T. et al. (1982). "Dephosphorylation of DNA," in *Molecular Cloning: A Laboratory Manual*, Cold Harbor Spring Laboratory: Cold Spring Harbor, NY, pp. 133-134.

Mannino, R.J. et al. (1988). "Liposome Mediated Gene Transfer," *Bio Techniques* 6(7):682-690.

Masseyeff, R.F. ed. (1993). *Methods of Immunological Analysis. vol. 1: Fundamentals*, Verlagsgesellschaft mbH, D-6940, Weinheim, Germany: pp. xi-xxii, (Table of Contents Only.).

Matteucci, M. (1997). "Oligonucleotide Analogs: An Overview," in *Oligonucleotides as Therapeutic Agents*, John Wiley and Sons: New York, NY, pp. 5-18.

Mayer, C. et al. (1997). "Cloning, Production, Characterization and IgE Cross-Reactivity of Different Manganese Superoxide Dismutases in Individuals Sensitized to *Aspergillus fumigatus*," *Int. Arch. Allergy Immunol.* 113:213-215.

Mbawuike, I.N. et al. (1994). "Influenza A Subtype Cross-Protection After Immunization of Outbred Mice with a Prefered Chimeric $NS_1$/$HA_2$ Influenza Virus Protein," *Vaccine* 12(14):1340-1348.

Mealy, N.E. et al. (Jan. 1, 2005). "Annual Update 2004/2005—Treatment of Respiratory Disorders," *Drugs of the Future* 30(1):51-107.

Messing, J. et al. (1981). "A System for Shotgun DNA Sequencing," *Nucleic Acids Res.* 9(2):309-321.

Miller, P.S. et al. (Dec. 1, 1971). "Syntheses and Properties of Adenine and Thymine Nucleoside Alkyl Phosphotriesters, the Neutral Analogs of Dinucleoside Monophosphates," *JACS* 93(24):6657-6665.

Miller, J.H. et al. eds. (1987). "Gene Transfer Vectors for Mammalian Cells," in *Current Communications in Molecular Biology*, Cold Spring Harbor Laboratory: Cold Spring Harbor, NY pp. vii-ix, (Table of Contents Only.).

Moser, M. et al. (Jan. 1994). "Clinical Aspects of Allergic Disease: Diagnostic Value of Recombinant *Aspergillus* Allergen I/a for Skin Testing and Serology," *J. Allergy Clin, Immunol*, 93(1-Part 1): 1-11.

Mueller, G.A. et al. (1997). "Expression and Secondary Structure Determination by NMR Methods of the Major Dust Mite Allergen Der p 2", *J. Biol. Chem.* 272(43):26893-26898.

Müller, U.R. et al. (Sep. 1995). "Type 1 Skin Reactivity to Native and Recombinant Phospholipase $A_2$ from Honeybee Venom is Similar," *J. Allergy Clin. Immunol.* 96(3):395-402.

Müller, U. et al. (1997). "Increased Specificity of Diagnostic Tests with Recombinant Major Bee Venom Allergen Phospholiapse A2," *Clin. Exp. Allergy* 27:915-920.

Mullis, K.B. et al. eds. (1994). *PCR: The Polymerase Chain Reaction*, Birkhäuser: Boston, MA, pp. xv-xvii (Table of Contents Only.).

Nelson, P.S. et al. (1989). "Bifunctional Oligonucleotide Probes Synthesized Using a Novel CPG Support are able to Detect Single Base Pair Mutations," *Nucleic Acids Res.* 17(18):7187-7194.

Nelson, J.S. et al. (1997). "N3'→P5' Oligodeoxyribonucleotide Phosphoramidates: A New Method of Synthesis Based on a Phosphoramidite Amine-Exchange Reaction," *J. Org. Chem.* 62(21):7278-7287.

Niederberger, V. et al. (Feb. 1998). "IgE Antibodies to Recombinant Pollen Allergens (Phl p 1, Phl p 2, Phl p 5, and Bet v 2) Account for a High Percentage of Grass Pollen-Specific Ige," *J. Allergy Clin. Immun.* 101(2-Part 1):258-264.

O'Shannessy, D.J. et al. (1985). "Specific Conjugation Reactions of the Oligosaccharide Moieties of Immunoglobulins," *J. Applied Biochem.* 7:347-355.

Osborne, S.E. et al. (1996). "Incorporating Disulfide Cross-Links at the Terminus of Oligonucleotides via Solid-Phase Nucleic Acid Synthesis," *Bioorganic & Medicinal Chemistry Letters* 6(19):2339-2342.

Osborne, S.E. et al. (Dec. 4, 1996). "Design, Synthesis, and Analysis of Disulfide Cross-Linked DNA Duplexes," *J. Am Chem. Soc.* 118(48):11993-12003.

Parronchi, P. et al. (Apr. 1996). "Effects of Interferon-α on Cytokine Profile, T Cell Receptor Repertoire and Peptide Reactivity of Human Allergen-Specific T Cells," *Eur. J. Immunol.* 26:697-703.

Pastorello, E.A. et al. (Dec. 1998). "Sensitization to the Major Allergen of Brazil Nut is Correlated with the Clinical Expression of Allergy," *J. Allergy Clin. Immunol.* 102(6-Part.1):1021-1027.

Pauli, G. et al. (May 1996). "Allergens, IgE, Mediators, Inflammatory Mechanims: Skin Testing with Recombinant Allergens rBet v 1 and Birch Profilin, rBet v 2: Diagnostic Value for Birch Pollen and Associated Allergies," *J. Allergy Clin. Immunol.* 97(5):1100-1109.

Peyrottes, S. et al. (1996). "Oligodeoxynucleoside Phosphoramidates (P-$NH_2$): Synthesis and Thermal Stability of Duplexes with DNA and RNA Targets," *Nucleic Acids Res.* 24(10):1841-1848.

Pisetsky, D.S. (Jan. 16, 1996). "The Immunologic Properties of DNA," *J. Immunol.* 156(2):421-423.

Rafnar, T. et al. (Jan. 15, 1991). "Cloning of *Amb a I* (Antigen E), the Major Allergen Family of Short Ragweed Pollen," *J. Biol. Chem.* 266(2):1229-1236.

Rautiainen, J. et al. (1998). "Molecular and Crystal Properties of Bos d 2, an Allergenic.Protein of the Lipocalin Family," *Biochem. Bioph. Res. Comm.* 247(3):746-750.

Reese, G. et al. (1997). "Characterization of Recombinant Shrimp Allergen Pen a 1 (Tropomyosin)," *Int. Arch. Allergy Immunol.* 113:240-242.

Rogers, B.L. et al. (1993). "Recombinant *Fel d* I: Expression, Purification, IgE Binding and Reaction with Cat-Allergic Human T Cells," *Mol. Immunol.* 30(6):559-568.

Roget, A. et al. (1989). "Synthesis and Use of Labelled Nucleoside Phosphoramidite Building Blocks Bearing a Reporter Group: Biotinyl, Dinitrophenyl, Pyrenyl and Dansyl," *Nucleic Acids Res.* 17(19):7643-7651.

Romagnani, S. (Jul. 2000). "T-Cell Subsets (Th1 versus Th2)," *Annals of Allergy, Asthma, & Immunology* 85(1):9-21.

Roman, M. et al. (Aug. 1997). "Immunostimulatory DNA Sequences Function as T Helper-1-Promoting Adjuvants," *Nature Med.* 3(8):849-854.

Ruth, J. L. (1991). "Oligodeoxynucleotides with Reporter Groups Attached to the Base," Chapter 11 in *Oligonucleotides and Analogues: A Practical Approach*, F. Eckstein, ed., IRL Press: pp. 255-282.

Sambrook, J. et al. eds. (1989). *Molecular Cloning: A Laboratory Manual*, Second Edition, Cold Spring Harbor Laboratory Press: Cold Spring Harbor, NY, pp. xi-xxxviii, (Table of Contents Only.).

Sato, Y. et al. (Jul. 1996). "Immunostimulatory DNA Sequences Necessary for Effective Intradermal Gene Immunization," *Science* 273:352-354.

Schacht, E. et al. (Oct. 5, 1996). "Biomedical Applications of Degradable Polyphosphazenes," *Biotechnol. Bioeng.* 52(1):102-108.

Scheerens, H. et al. (2001). "Characterization of Chemokines and Chemokine Receptors in Two Murine Models of Inflammatory Bowel Disease: IL-10$^{-/-}$ Mice and Rag 2$^{-/-}$ Mice Reconstituted with CD4$^+$CD45RB$^{high}$ T Cells," *Eur. J. Immunolgy* 31:1465-1474.

Scherle, P.A. et al. (Oct. 1986). "Functional Analysis of Influenza Specific-Helper T Cell Clones In Vivo," *J. Exp. Med.* 164:1114-1128.

Scherle, P.A. et al. (Jun. 1988). "Differential Ability of B Cells Specific for External vs. Internal Influenza Virus Proteins to Respond to Help from Influenza Virus-Specific T-cell Clones In Vivo," *PNAS USA* 85:4446-4450.

Scheurer, S. et al. (1997). "Molecular Cloning, Expression and Characterization of Pru a 1, the Major Cherry Allergen," *Mol. Immunol.* 34(8/9):619-629.

Schmidt, M. et al. (Jul. 1996). "Production of a Recombinant Imported Fire Ant Venom Allergen, Sol I 2, in Native and Immunoreactive Form," *J. Allergy Clin. Immunol.* 98(1):82-88.

Schramm, G. et al. (1998). "Molecular and Immunological Characterization of Group V Allergen Isoforms from Velvet Grass Pollen (*Holcus lanatus*)," *Eur. J. Biochem.* 252:200-206.

Schroeder, U. et al. (1998). "Efficacy of Oral Dalargin-Loaded Nanoparticle Delivery Across the Blood-Brain Barrier," *Peptides* 19(4):777-780.

Schultz, R.G. et al. (Jul. 1996). "Oligo-2'-Fluoro-2'-Deoxynucleotide N3'→P5' Phosphoramidates: Synthesis and Properties," *Nucleic Acids Res.* 24(15):2966-2973.

Sélo, I. et al. (1999). "Allergy to Bovine β-Lactoglobulin: Specificity of Human IgE to Tryptic Peptides," *Clin. Exp. Allergy* 29:1055-1063.

Shen, H.-D. et al. (1997). "Molecular Cloning and Expression of a *Penicillium citrinum* Allergen with Sequence Homology and Antigenic Crossreactivity to a hsp 70 Human Heat Shock Protein," *Clin. Exp. Allergy* 27:682-690.

Shimada, S. et al. (Aug. 1986). "In Vivo Augmentation of Natural Killer Cell Activity with a Deoxyribonucleic Acid Fraction of BCG," *Jpn. J. Cancer Res.* 77:808-816.

Slunt, J.B. et al. (Jun. 1995). "IgE Antibodies to Recombinant Forms of *Fel d* 1: Dichotomy Between Fluid-Phase and Solid-Phase Binding Studies," *J. Allergy Clin. Immunol.* 95:1221-1228.

Smith, P.M. et al. (1997). "Identification of Ca$^{2+}$ Binding Protein as a New Bermuda Grass Pollen Allergen Cyn d7: IgE Cross-reactivity with Oilseed Rape Pollen Allergen Bra r 1," *Int. Arch. Allergy Immunol.* 114:265-271.

Smith, A.M. et al. (Mar. 1998). "Recombinant Allergens for Immunotherapy: A Der p 2 Variant with Reduced IgE Reactivity Retains T-Cell Epitopes," *J. Allergy Clin. Immunol.* 101(3):423-425.

Soldatova, L.N. et al. (May 1998). "Superior Biologic Activity of the Recombinant Bee Venom Allergen Hyaluronidase Expressed in Baculovirus-Infected Insect Cells as Compared with *Escherichia coli*," *J. Allergy Clin. Immunol.* 101(5):691-698.

Sowka, S. et al. (1998). "cDNA Cloning of the 43-kDa Latex Allergen Hev b 7 with Sequence Similarity to Patatins and its Expression in the Yeast *Pichia Pastoris*," *Eur. J. Biochem.* 255:213-219.

Spitzauer, S. et al. (Mar. 1994). "Molecular Characterization of Dog Albumin as a Cross-Reactive Allergen," *J. Allergy Clin. Immunol.* 93(3):614-627.

Stanley, J.S. et al. (1996). "Peanut Hypersensitivity: IgE Binding Characteristics of a Recombinant *Ara h* 1 Protein," in *New Horizons in Allergy Immunotherapy*, Sehon, A. et al. eds., Plenum Press: New York, NY, pp. 213-216.

Staros, J.V. et al. (1986). "Enhancement by *N*-Hydroxysulfosuccinimide of Water-Soluble Carbodiimide-Mediated Coupling Reactions," *Anal. Biochem.* 156:220-222.

Stirchak, E.P. et al. (1989). "Uncharged Stereoregular Nucleic Acid Analogs: 2. Morpholino Nucleoside Oligomers with Carbamate Internucleoside Linkages," *Nucleic Acids Res.* 17(15):6129-6141.

Sun, L.K. et al. (Aug. 1995). "Human IgA Monoclonal Antibodies Specific for a Major Ragweed Pollen Antigen," *Biotechnology* 13:779-786.

Tamborini, E. et al. (1997). "Biochemical and Immunological Characterization of Recombinant Allergen Lol p 1," *Eur. J. Biochem.* 249:886-894.

Tamura, S-I. et al. (1992). "Superior Cross-Protective Effect of Nasal Vaccination to Subcutaneous Inoculation with Influenza Hemagglutinin Vaccine," *Eur. J. Immunol.* 22:477-481.

Tamura, S-I. et al. (1994). "Formulation of Inactivated Influenza Vaccines for Providing Effective Cross-Protection by Intranasal Vaccination in Mice," *Vaccine* 12(4):310-316.

Teuber, S.S. et al. (Jun. 1998). "Cloning and Sequencing of a Gene Encoding a 2S Albumin Seed Storage Protein Precursor from English Walnut (*Juglans Regia*), a Major Food Allergen," *J. Allergy Clin. Immun.* 101(6-Part 1):807-814.

Thiel, K. (Jun. 2004). "Oligo Oligarchy—The Surprisingly Small World of Aptamers," *Nature Biotechnology* 22(6):649-651.

Tinghino, R. et al. (Jun. 1998). "Allergens, IgE, Mediators, Inflammatory Mechanisms: Molecular Characterization of a Cross-Reactive *Juniperus oxycedrus* Pollen Allergen, June o 2: A Novel Calcium-Binding Allergen," *J. Allergy Clin. Immunol.* 101(6-Part 1):772-777.

Tomalski, M.D. et al. (1993). "Expression of Hornet Genes Encoding Venom Allergen Antigen 5 in Insects," *Arch. Insect Biochem. Physiol.* 22:303-313.

Tulic, M.K. et al. (Feb. 2004). "Amb a 1-Immunostimulatory Oligodeoxynucleotide Conjugate Immunotherapy Decreases the Nasal Inflammation Response," *The Journal of Allergy and Clinical Immunology* 113(2):235-241.

Tung, C.-H. et al. (1991). "Preparation of Oligonucleotide-Peptide Conjugates," *Bioconjug. Chem.* 2:464-465.

Twardosz, A. et al. (1997). "Molecular Characterization, Expression in *Escherichia coli*, and Epitope Analysis of a Tqo EF-Hand Calcium-Binding Birch Pollen Allergen, Bet v 4," *Biochem. Bioph. Res Comm.* 239(1):197-204.

Vailes, L.D. et al. (Feb. 1998). "High-Level Expression of Cockroach Allergen, Bla g 4, in *Pichia pastoris*," *J. Allergy Clin. Immunol.* 101(2-Part 1):274-280.

Vallverdú, A. et al. (Mar. 1998). "Characterization of Recombinant *Mercurialis annua* Major Allergen Mer a 1 (profilin)," *J. Allergy Clin. Immunol.* 101(3):363-370.

Van Do, T. et al. (1999). "Expression and Analysis of Recombinant Salmon Parvalbumin, the Major Allergen in Atlantic Salmon (*Salmo salar*)," *Scand. J. Immunol.* 50:619-625.

Van Neerven, R.J.J. et al. (1998). "Preserved Epitope-Specific T Cell Activation by Recombinant Bet v 1-MBP Fusion Proteins," *Clin. Exp. Allergy* 28:423-433.

Vrtala, S. et al. (Jun. 15, 1998). "Immunization with Purified Natural and Recombinant Allergens Induces Mouse IgG1 Antibodies That Recognize Similar Epitopes as Human IgE and Inhibit the Human IgE-Allergen Interaction and Allergen-Induced Basophil Degranulation," *J. Immunol.* 160:6137-6144.

Wang, S. et al. (1994). "Circular RNA Oligonucleotides. Synthesis, Nucleic Acid Binding Properties, and a Comparison with Circular DNAs," *Nucleic Acids Res.* 22(12):2326-2333.

Wang, H. et al. (Mar. 22, 1995). "Solution Structure of a Disulfide Cross-Linked DNA Hairpin," *J. Am Chem. Soc.* 117(11):2981-2991.

Warner, B.D. et al. (Oct. 1984). "Laboratory Methods: Construction and Evaluation of an Instrument for the Automated Synthesis of Oligodeoxyribonucleotides," *DNA* 3(5):401-411.

Watwe, R.M. et al. (Apr. 10, 1995). "Manufacture of Liposomes: A Review," *Current Science* 68(7):715-724.

Weir, D.M. et al. eds. (1986) "vol. 4: Applications of Immunological Methods in Biomedical Sciences," *Handbook of Experimental Immunology in Four Volumes*, Blackwell Scientific Publications, pp. v-x, (Table of Contents Only.).

Wild, D. ed. (1994). *The Immunoassay Handbook*, Stockton Press: New York, NY, pp. v-xvi, (Table of Contents Only.).

Wu, C.H. et al. (1997). "Sequencing and Immunochemical Characterization of the American Cockroach Per a 3 (cr-PI) Isoallergenic Variants," *Mol. Immunol.* 34:1-8.

Xu, W. et al. (1998). "Expression and Rapid Purification of an *Aedes aegypti* Salivary Allergen by a Baculovirus System," *Int. Arch. Allergy Immunol.* 115:245-251.

Yamamoto, S, et al. (Jun. 15, 1992). "Unique Palindromic Sequences in Synthetic Oligonucleotides are Required to Induce INF and Augment INF-Mediated Natural Killer Activity," *J. Immunol.* 148(12):4072-4076.

Yanagawa, H. et al. (Feb. 1988). "Analysis of Superhelical Structures of Nucleic Acid-Lipid Conjugates by Image Processing," *Nucleic Acids Symp. Series* 19:189-192.

Yasue, M. et al. (1997). "Inhibition of Airway Inflammation in rDer f 2-Sensitized Mice by Oral Administration of Recombinant Der f 2," *Cell Immunol.* 181:30-37.

Yasue, M. et al. (1998). "Hyposensitization to Allergic Reaction in rDer f 2-Sensitized Mice by the Intranasal Administration of a Mutant rDer f 2, C8/119S," *Clin. Exp. Immunol.* 113:1-9.

Yokoyama, M. et al. (2000). "Purification, Identification, and cDNA Cloning of Jun a 2, the Second Major Allergen of Mountain Cedar Pollen," *Biochem. Biophys. Res. Commun.* 275(1):195-202.

Youn, C.J. et al. (2004). "Immunostimulatory DNA Reverses Established Allergen-Induced Airway Remodeling," *The Journal of Immunology* 173:7556-7564.

Zeiler, T. et al. (Dec. 1997). "Clinical Aspects of Allergic Disease: Recombinant Allergen Fragments as Candidate Preparations for Allergen Immunotherapy," *J. Allergy Clin. Immunol.* 100(6-Part 1):721-727.

Zhang, L. et al. (Jul. 15, 1993). "Antigen- and Isotype-Specific Immune Responses to a Recombinant Antigen-Allergen Chimeric (RAAC) Protein," *J. Immunol.* 151(2):791-799.

Zon, G. (1993). "Oligonucleoside Phosphorothioates," Chapter 8 in *Protocols for Oligonucleotides and Analogs, Synthesis and Properties*, Agrawal, S. ed., vol. 20, Humana Press: Totowa, NJ, pp. 165-189.

Zuckermann, R. et al. (1987). "Efficient Methods for Attachment of Thiol Specific Probes to the 3'-Ends of Synthetic Oligodeoxyribonucleotides," *Nucleic Acids Res.* 15(13):5305-5321.

Creticos, P.S. (Feb. 2000). "The Consideration of Immunotherapy in the Treatment of Allergic Asthma," *Journal of Allergy and Clinical Immunology* 105(2, Part 2):S559-S574.

Krieg, A.M. (Jun. 2006). "Therapeutic Potential of Toll-Like Receptor 9 Activation," *Nature Reviews: Drug Discovery* 5(6):471-484.

Simmons, F.E.R. et al. (Jun. 2004). "Selective Immune Redirection in Humans with Ragweed Allergy by Injecting Amb a 1 Linked to Immunostimulatory DNA," *Journal of Allergy and Clinical Immunology* 113(6):1144-1151.

Creticos et al. (Oct. 5, 2006). "Immunotherapy with a Ragweed-Toll-Like Receptor 9 Agonist Vaccine for Allergic Rhinitis," *New England Journal of Medicine* 355(14):1445-1455.

Dynavax Technologies (Oct. 4, 2006). "New England Journal of Medicine Reports Positive Results From Dynavax' Ragweed Allergy Therapy Trial," located at <http://investors.dynavax.com/releasedetail.cfm?releaseid=231026 >, last visited on Nov. 9, 2009, 2 pages.

Rhee, C-S. et al. (2004). "Allergen-Independent Immunostimulatory Sequence Oligodeoxynucleotide Therapy Attenuates Experimental Allergic Rhinitis," *Immunology* 113:106-113.

Takabayashi, K. et al. (2003). "Intranasal Immunotherapy Is More Effective Than Intradermal Immunotherapy for the Induction of Airway Allergen Tolerance in Th2-Sensitized Mice," *The Journal of Immunology* 170:3898-3905.

Tighe, H. et al. (Jul. 2000). "Conjugation of Immunostimulatory DNA to the Short Ragweed Allergen Amb a 1 Enhances its Immunogenicity and Reduces its Allergenicity," *J. Allergy Clin. Immunol.* 106(1, part 1):124-134.

Voet, D. et al. (1990). "Table 26-1: Names and Abbreviations of Nucleic Acid Bases, Nucleosides, and Nucleotides," in *Biochemistry*, John Wiley & Sons: New York, NY, p. 742.

Wang, Y. (2007). "Tolamba™.TLR9 Receptor Agonist. Treatment of Allergic Rhinitis," *Drugs of the Future* 32(6):497-500.

* cited by examiner

Figure 3

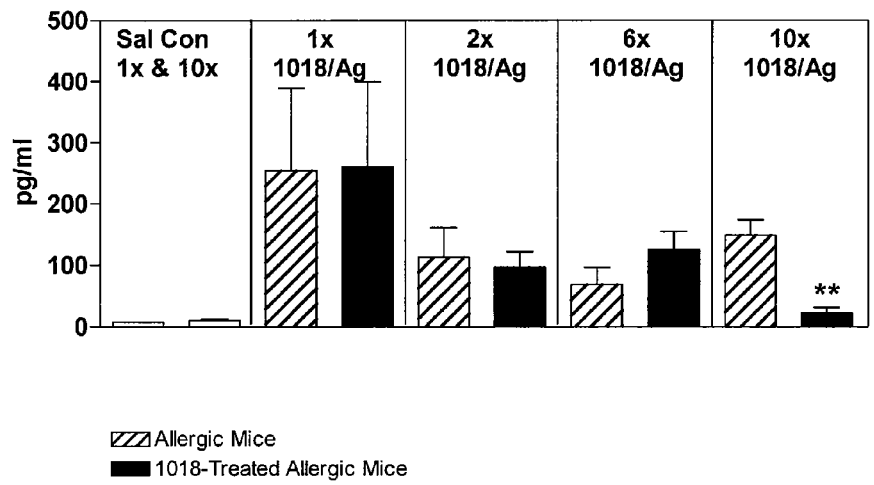

▨ Allergic Mice
■ 1018-Treated Allergic Mice

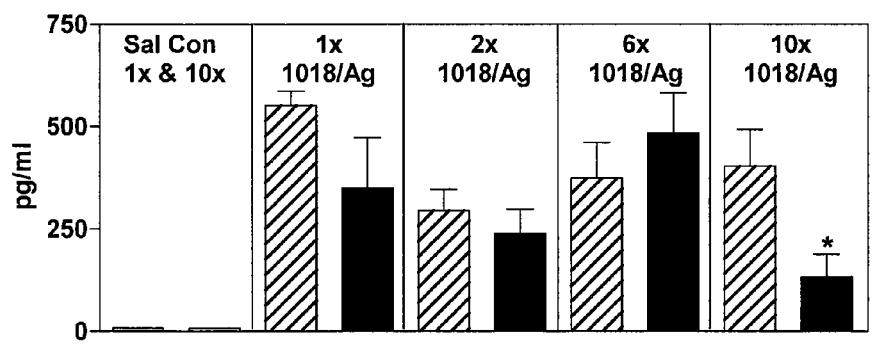

Open bars: ragweed sensitized, weekly saline challenge and saline treatment, after two weeks rest saline re-challenge.

Striped bars: ragweed sensitized, weekly ragweed challenge and saline treatment, after two weeks rest ragweed re-challenge.

Black bars: ragweed sensitized, weekly ragweed challenge and 1018 ISS treatment, after two weeks rest ragweed re-challenge.

Figure 4

IL-10 in BAL fluid

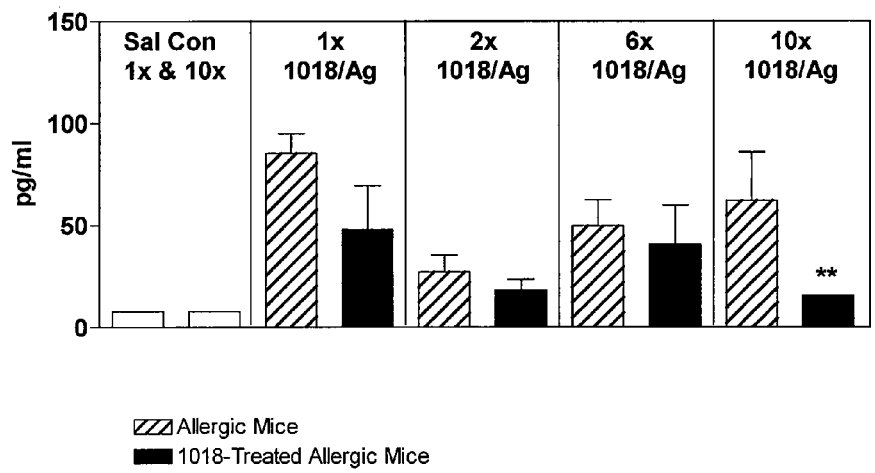

☒ Allergic Mice
■ 1018-Treated Allergic Mice

IFN-γ in BAL fluid

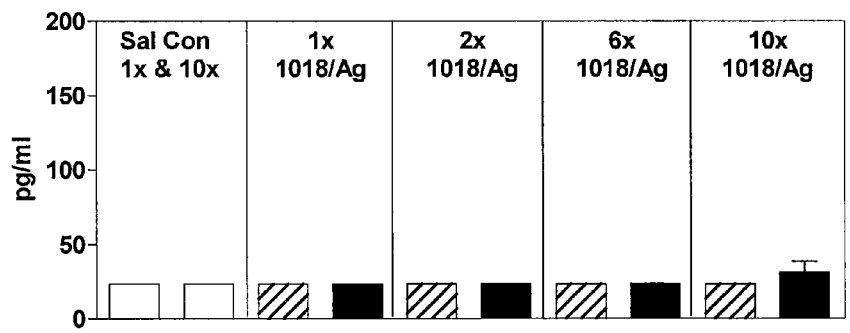

Open bars: ragweed sensitized, weekly saline challenge and saline treatment, after two weeks rest saline re-challenge.

Striped bars: ragweed sensitized, weekly ragweed challenge and saline treatment, after two weeks rest ragweed re-challenge.

Black bars: ragweed sensitized, weekly ragweed challenge and 1018 ISS treatment, after two weeks rest ragweed re-challenge.

Open bars: ragweed sensitized, weekly saline challenge and saline treatment, after two weeks rest saline re-challenge.

Striped bars: ragweed sensitized, weekly ragweed challenge and saline treatment, after two weeks rest ragweed re-challenge.

Black bars: ragweed sensitized, weekly ragweed challenge and 1018 ISS treatment, after two weeks rest ragweed re-challenge.

Long-Term Treatment with TOLAMBA or 1018 ISS Leads to Non-Responsiveness to Allergen in the Airways

SEQUENCE LISTING

```
<160> NUMBER OF SEQ ID NOS: 28

<210> SEQ ID NO 1
<211> LENGTH: 22
<212> TYPE: DNA
<213> ORGANISM: Artificial Sequence
<220> FEATURE:
<223> OTHER INFORMATION: Immunostimulatory polynucleotide

<400> SEQUENCE: 1
tgactgtgaa cgttcgagat ga                                              22

<210> SEQ ID NO 2
<211> LENGTH: 16
<212> TYPE: DNA
<213> ORGANISM: Artificial Sequence
<220> FEATURE:
<223> OTHER INFORMATION: Immunostimulatory polynucleotide
<220> FEATURE:
<221> NAME/KEY: misc_feature
<222> LOCATION: (1)...(3)
<223> OTHER INFORMATION: n = absent, A, T, C or G
<220> FEATURE:
<221> NAME/KEY: misc_feature
<222> LOCATION: (7)...(8)
<223> OTHER INFORMATION: n = absent, A, T, C or G
<220> FEATURE:
<221> NAME/KEY: misc_feature
<222> LOCATION: (4)...(8)
<223> OTHER INFORMATION: Sequence of bases 4-8 may be repeated up to 4
      times.
<220> FEATURE:
<221> NAME/KEY: misc_feature
<222> LOCATION: (9)...(10)
<223> OTHER INFORMATION: n = absent, A, T, C or G
<220> FEATURE:
<221> NAME/KEY: misc_feature
<222> LOCATION: 11
<223> OTHER INFORMATION: n = A, T, C or G and base is complementary to
      base 14
<220> FEATURE:
<221> NAME/KEY: misc_feature
<222> LOCATION: 14
<223> OTHER INFORMATION: n = A, T, C or G and base is complementary to
      base 11
<220> FEATURE:
<221> NAME/KEY: misc_feature
<222> LOCATION: (15)...(16)
<223> OTHER INFORMATION: Bases 15-16 may be absent
<220> FEATURE:
<221> NAME/KEY: misc_feature
<222> LOCATION: (11)...(16)
<223> OTHER INFORMATION: Sequence of bases 11-16 may be repeated up to
      20 times

<400> SEQUENCE: 2
```

```
nnntcgnnnn ncgncg                                              16
```

```
<210> SEQ ID NO 3
<211> LENGTH: 5
<212> TYPE: DNA
<213> ORGANISM: Artificial Sequence
<220> FEATURE:
<223> OTHER INFORMATION: Immunostimulatory polynucleotide
<220> FEATURE:
<221> NAME/KEY: misc_feature
<222> LOCATION: (4)...(5)
<223> OTHER INFORMATION: n = absent, A, T, C or G
<220> FEATURE:
<221> NAME/KEY: misc_feature
<222> LOCATION: (1)...(5)
<223> OTHER INFORMATION: Sequence of bases 1-5 may be repeated up to 4
      times

<400> SEQUENCE: 3 tcgnn                                                           5

<210> SEQ ID NO 4
<211> LENGTH: 20
<212> TYPE: DNA
<213> ORGANISM: Artificial Sequence
<220> FEATURE:
<223> OTHER INFORMATION: Immunostimulatory polynucleotide
<220> FEATURE:
<221> NAME/KEY: misc_feature
<222> LOCATION: (1)...(3)
<223> OTHER INFORMATION: n = absent, A, T, C or G
<220> FEATURE:
<221> NAME/KEY: misc_feature
<222> LOCATION: (7)...(8)
<223> OTHER INFORMATION: n = absent, A, T, C or G
<220> FEATURE:
<221> NAME/KEY: misc_feature
<222> LOCATION: (4)...(8)
<223> OTHER INFORMATION: Sequence of bases may be repeated up to 4 times
<220> FEATURE:
<221> NAME/KEY: misc_feature
<222> LOCATION: (9)...(10)
<223> OTHER INFORMATION: n = absent, A, T, C or G
<220> FEATURE:
<221> NAME/KEY: misc_feature
<222> LOCATION: 11
<223> OTHER INFORMATION: n = A, T, C or G and base is complementary to
      base 18
<220> FEATURE:
<221> NAME/KEY: misc_feature
<222> LOCATION: 12
<223> OTHER INFORMATION: n = A, T, C or G and base is complementary to
      base 17
<220> FEATURE:
<221> NAME/KEY: misc_feature
<222> LOCATION: 13
<223> OTHER INFORMATION: n = A, T, C or G and base is complementary to
      base 16
<220> FEATURE:
<221> NAME/KEY: misc_feature
<222> LOCATION: 16
<223> OTHER INFORMATION: n = A, T, C or G and base is complementary to
      base 13
<220> FEATURE:
<221> NAME/KEY: misc_feature
<222> LOCATION: 17
<223> OTHER INFORMATION: n = A, T, C or G and base is complementary to
      base 12
<220> FEATURE:
<221> NAME/KEY: misc_feature
<222> LOCATION: 18
<223> OTHER INFORMATION: n = A, T, C or G and base is complementary to
      base 11
<220> FEATURE:
<221> NAME/KEY: misc_feature
<222> LOCATION: (19)...(20)
<223> OTHER INFORMATION: Bases 19-20 may be absent
```

```
<220> FEATURE:
<221> NAME/KEY: misc_feature
<222> LOCATION: (11)...(20)
<223> OTHER INFORMATION: Sequence of bases 11-20 may be repeated up to
      20 times

<400> SEQUENCE: 4
nnntcgnnnn nnncgnnncg                                                    20

<210> SEQ ID NO 5
<211> LENGTH: 10
<212> TYPE: DNA
<213> ORGANISM: Artificial Sequence
<220> FEATURE:
<223> OTHER INFORMATION: Immunostimulatory polynucleotide
<220> FEATURE:
<221> NAME/KEY: misc_feature
<222> LOCATION: 1
<223> OTHER INFORMATION: n = A, T, G or C and base is complementary to
      base 8
<220> FEATURE:
<221> NAME/KEY: misc_feature
<222> LOCATION: 2
<223> OTHER INFORMATION: n = A, T, G or C and base is complementary to
      base 7
<220> FEATURE:
<221> NAME/KEY: misc_feature
<222> LOCATION: 3
<223> OTHER INFORMATION: n = A, T, G or C and base is complementary to
      base 6
<220> FEATURE:
<221> NAME/KEY: misc_feature
<222> LOCATION: 6
<223> OTHER INFORMATION: n = A, T, G or C and base is complementary to
      base 3
<220> FEATURE:
<221> NAME/KEY: misc_feature
<222> LOCATION: 7
<223> OTHER INFORMATION: n = A, T, G or C and base is complementary to
      base 2
<220> FEATURE:
<221> NAME/KEY: misc_feature
<222> LOCATION: 8
<223> OTHER INFORMATION: n = A, T, G or C and base is complementary to
      base 1
<220> FEATURE:
<221> NAME/KEY: misc_feature
<222> LOCATION: (9)...(10)
<223> OTHER INFORMATION: Bases 9-10 may be absent

<400> SEQUENCE: 5 nnncgnnncg                                                               10

<210> SEQ ID NO 6
<211> LENGTH: 22
<212> TYPE: DNA
<213> ORGANISM: Artificial Sequence
<220> FEATURE:
<223> OTHER INFORMATION: Immunostimulatory polynucleotide
<220> FEATURE:
<221> NAME/KEY: misc_feature
<222> LOCATION: (1)...(3)
<223> OTHER INFORMATION: n = absent, A, T, C or G
<220> FEATURE:
<221> NAME/KEY: misc_feature
<222> LOCATION: (7)...(8)
<223> OTHER INFORMATION: n = absent, A, T, C or G
<220> FEATURE:
<221> NAME/KEY: misc_feature
<222> LOCATION: (4)...(8)
<223> OTHER INFORMATION: Sequence of bases 4-8 may be repeated up to 4
      times
<220> FEATURE:
<221> NAME/KEY: misc_feature
<222> LOCATION: (9)...(10)
<223> OTHER INFORMATION: n = absent, A, T, C or G
```

```
<220> FEATURE:
<221> NAME/KEY: misc_feature
<222> LOCATION: 11
<223> OTHER INFORMATION: n = A, T, C or G and base is complementary to
      base 20
<220> FEATURE:
<221> NAME/KEY: misc_feature
<222> LOCATION: 12
<223> OTHER INFORMATION: n = A, T, C or G and base is complementary to
      base 19
<220> FEATURE:
<221> NAME/KEY: misc_feature
<222> LOCATION: 13
<223> OTHER INFORMATION: n = A, T, C or G and base is complementary to
      base 18
<220> FEATURE:
<221> NAME/KEY: misc_feature
<222> LOCATION: 14
<223> OTHER INFORMATION: n = A, T, C or G and base is complementary to
      base 17
<220> FEATURE:
<221> NAME/KEY: misc_feature
<222> LOCATION: 17
<223> OTHER INFORMATION: n = A, T, C or G and base is complementary to
      base 14
<220> FEATURE:
<221> NAME/KEY: misc_feature
<222> LOCATION: 18
<223> OTHER INFORMATION: n = A, T, C or G and base is complementary to
      base 13
<220> FEATURE:
<221> NAME/KEY: misc_feature
<222> LOCATION: 19
<223> OTHER INFORMATION: n = A, T, C or G and base is complementary to
      base 12
<220> FEATURE:
<221> NAME/KEY: misc_feature
<222> LOCATION: 20
<223> OTHER INFORMATION: n = A, T, C or G and base is complementary to
      base 11
<220> FEATURE:
<221> NAME/KEY: misc_feature
<222> LOCATION: (21)...(22)
<223> OTHER INFORMATION: Bases 21-22 may be absent
<220> FEATURE:
<221> NAME/KEY: misc_feature
<222> LOCATION: (11)...(22)
<223> OTHER INFORMATION: Sequence of bases 11-22 may be repeated up to
      20 times

<400> SEQUENCE: 6
nnntcgnnnn nnnncgnnnn cg                                             22

<210> SEQ ID NO 7
<211> LENGTH: 10
<212> TYPE: DNA
<213> ORGANISM: Artificial Sequence
<220> FEATURE:
<223> OTHER INFORMATION: Immunostimulatory polynucleotide
<220> FEATURE:
<221> NAME/KEY: misc_feature
<222> LOCATION: 1
<223> OTHER INFORMATION: n = A, T, C or G and base is complementary to
      base 10
<220> FEATURE:
<221> NAME/KEY: misc_feature
<222> LOCATION: 2
<223> OTHER INFORMATION: n = A, T, C or G and base is complementary to
      base 9
<220> FEATURE:
<221> NAME/KEY: misc_feature
<222> LOCATION: 3
<223> OTHER INFORMATION: n = A, T, C or G and base is complementary to
      base 8
<220> FEATURE:
<221> NAME/KEY: misc_feature
<222> LOCATION: 4
<223> OTHER INFORMATION: n = A, T, C or G and base is complementary to
```

-continued

```
      base 7
<220> FEATURE:
<221> NAME/KEY: misc_feature
<222> LOCATION: 7
<223> OTHER INFORMATION: n = A, T, C or G and base is complementary to
      base 4
<220> FEATURE:
<221> NAME/KEY: misc_feature
<222> LOCATION: 8
<223> OTHER INFORMATION: n = A, T, C or G and base is complementary to
      base 3
<220> FEATURE:
<221> NAME/KEY: misc_feature
<222> LOCATION: 9
<223> OTHER INFORMATION: n = A, T, C or G and base is complementary to
      base 2
<220> FEATURE:
<221> NAME/KEY: misc_feature
<222> LOCATION: 10
<223> OTHER INFORMATION: n = A, T, C or G and base is complementary to
      base 1

<400> SEQUENCE: 7 nnnncgnnnn                                                                10

<210> SEQ ID NO 8
<211> LENGTH: 12
<212> TYPE: DNA
<213> ORGANISM: Artificial Sequence
<220> FEATURE:
<223> OTHER INFORMATION: Immunostimulatory polynucleotide
<220> FEATURE:
<221> NAME/KEY: misc_feature
<222> LOCATION: 1
<223> OTHER INFORMATION: n = A, T, C or G and base is complementary to
      base 10
<220> FEATURE:
<221> NAME/KEY: misc_feature
<222> LOCATION: 2
<223> OTHER INFORMATION: n = A, T, C or G and base is complementary to
      base 9
<220> FEATURE:
<221> NAME/KEY: misc_feature
<222> LOCATION: 3
<223> OTHER INFORMATION: n = A, T, C or G and base is complementary to
      base 8
<220> FEATURE:
<221> NAME/KEY: misc_feature
<222> LOCATION: 4
<223> OTHER INFORMATION: n = A, T, C or G and base is complementary to
      base 7
<220> FEATURE:
<221> NAME/KEY: misc_feature
<222> LOCATION: 7
<223> OTHER INFORMATION: n = A, T, C or G and base is complementary to
      base 4
<220> FEATURE:
<221> NAME/KEY: misc_feature
<222> LOCATION: 8
<223> OTHER INFORMATION: n = A, T, C or G and base is complementary to
      base 3
<220> FEATURE:
<221> NAME/KEY: misc_feature
<222> LOCATION: 9
<223> OTHER INFORMATION: n = A, T, C or G and base is complementary to
      base 2
<220> FEATURE:
<221> NAME/KEY: misc_feature
<222> LOCATION: 10
<223> OTHER INFORMATION: n = A, T, C or G and base is complementary to
      base 1
<220> FEATURE:
<221> NAME/KEY: misc_feature
<222> LOCATION: (11)...(12)
<223> OTHER INFORMATION: Bases 11-12 may be absent

<400> SEQUENCE: 8
```

```
nnnncgnnnn cg                                                          12
```

<210> SEQ ID NO 9
<211> LENGTH: 18
<212> TYPE: DNA
<213> ORGANISM: Artificial Sequence
<220> FEATURE:
<223> OTHER INFORMATION: Immunostimulatory polynucleotide
<220> FEATURE:
<221> NAME/KEY: misc_feature
<222> LOCATION: (1)...(3)
<223> OTHER INFORMATION: n = absent, A, T, C or G
<220> FEATURE:
<221> NAME/KEY: misc_feature
<222> LOCATION: (7)...(8)
<223> OTHER INFORMATION: n = absent, A, T, C or G
<220> FEATURE:
<221> NAME/KEY: misc_feature
<222> LOCATION: (4)...(8)
<223> OTHER INFORMATION: Sequence of bases 4-8 may be repeated up to 4
      times
<220> FEATURE:
<221> NAME/KEY: misc_feature
<222> LOCATION: (9)...(10)
<223> OTHER INFORMATION: n = absent, A, T, C or G
<220> FEATURE:
<221> NAME/KEY: misc_feature
<222> LOCATION: 11
<223> OTHER INFORMATION: n = A, T, C or G and base is complementary to
      base 16
<220> FEATURE:
<221> NAME/KEY: misc_feature
<222> LOCATION: 16
<223> OTHER INFORMATION: n = A, T, C or G and base is complementary to
      base 11
<220> FEATURE:
<221> NAME/KEY: misc_feature
<222> LOCATION: (17)...(18)
<223> OTHER INFORMATION: Bases 17-18 may be absent
<220> FEATURE:
<221> NAME/KEY: misc_feature
<222> LOCATION: (11)...(18)
<223> OTHER INFORMATION: Sequence of bases 11-18 may be repeated up to
      20 times

<400> SEQUENCE: 9

```
nnntcgnnnn ncgcgncg                                                    18
```

<210> SEQ ID NO 10
<211> LENGTH: 18
<212> TYPE: DNA
<213> ORGANISM: Artificial Sequence
<220> FEATURE:
<223> OTHER INFORMATION: Immunostimulatory polynucleotide
<220> FEATURE:
<221> NAME/KEY: misc_feature
<222> LOCATION: (1)...(3)
<223> OTHER INFORMATION: n = absent, A, T, C or G
<220> FEATURE:
<221> NAME/KEY: misc_feature
<222> LOCATION: (7)...(8)
<223> OTHER INFORMATION: n = absent, A, T, C or G
<220> FEATURE:
<221> NAME/KEY: misc_feature
<222> LOCATION: (4)...(8)
<223> OTHER INFORMATION: Sequence of bases 4-8 may be repeated up to 4
      times
<220> FEATURE:
<221> NAME/KEY: misc_feature
<222> LOCATION: (9)...(10)
<223> OTHER INFORMATION: n = absent, A, T, C or G
<220> FEATURE:
<221> NAME/KEY: misc_feature
<222> LOCATION: 13
<223> OTHER INFORMATION: n = A, T, C or G and base is complementary to
      base 14
<220> FEATURE:

```
<221> NAME/KEY: misc_feature
<222> LOCATION: 14
<223> OTHER INFORMATION: n = A, T, C or G and base is complementary to
      base 13
<220> FEATURE:
<221> NAME/KEY: misc_feature
<222> LOCATION: (17)...(18)
<223> OTHER INFORMATION: Bases 17-18 may be absent
<220> FEATURE:
<221> NAME/KEY: misc_feature
<222> LOCATION: (11)...(18)
<223> OTHER INFORMATION: Sequence of bases 11-18 may be repeated up to
      20 times

<400> SEQUENCE: 10
nnntcgnnnn cgnncgcg                                                   18

<210> SEQ ID NO 11
<211> LENGTH: 22
<212> TYPE: DNA
<213> ORGANISM: Artificial Sequence
<220> FEATURE:
<223> OTHER INFORMATION: Immunostimulatory polynucleotide
<220> FEATURE:
<221> NAME/KEY: misc_feature
<222> LOCATION: (1)...(3)
<223> OTHER INFORMATION: n = absent, A, T, C or G
<220> FEATURE:
<221> NAME/KEY: misc_feature
<222> LOCATION: (7)...(8)
<223> OTHER INFORMATION: n = absent, A, T, C or G
<220> FEATURE:
<221> NAME/KEY: misc_feature
<222> LOCATION: (4)...(8)
<223> OTHER INFORMATION: Sequence of bases 4-8 may be repeated up to 4
      times
<220> FEATURE:
<221> NAME/KEY: misc_feature
<222> LOCATION: (9)...(10)
<223> OTHER INFORMATION: n = absent, A, T, C or G
<220> FEATURE:
<221> NAME/KEY: misc_feature
<222> LOCATION: 11
<223> OTHER INFORMATION: n = A, T, C or G and base is complementary to
      base 20
<220> FEATURE:
<221> NAME/KEY: misc_feature
<222> LOCATION: 12
<223> OTHER INFORMATION: n = A, T, C or G and base is complementary to
      base 19
<220> FEATURE:
<221> NAME/KEY: misc_feature
<222> LOCATION: 15
<223> OTHER INFORMATION: n = A, T, C or G and base is complementary to
      base 16
<220> FEATURE:
<221> NAME/KEY: misc_feature
<222> LOCATION: 16
<223> OTHER INFORMATION: n = A, T, C or G and base is complementary to
      base 15
<220> FEATURE:
<221> NAME/KEY: misc_feature
<222> LOCATION: 19
<223> OTHER INFORMATION: n = A, T, C or G and base is complementary to
      base 12
<220> FEATURE:
<221> NAME/KEY: misc_feature
<222> LOCATION: 20
<223> OTHER INFORMATION: n = A, T, C or G and base is complementary to
      base 11
<220> FEATURE:
<221> NAME/KEY: misc_feature
<222> LOCATION: (21)...(22)
<223> OTHER INFORMATION: Bases 21-22 may be absent
<220> FEATURE:
<221> NAME/KEY: misc_feature
<222> LOCATION: (11)...(22)
<223> OTHER INFORMATION: Sequence of bases 11-22 may be repeated up to
```

20 times

<400> SEQUENCE: 11
nnntcgnnnn nncgnncgnn cg        22

<210> SEQ ID NO 12
<211> LENGTH: 10
<212> TYPE: DNA
<213> ORGANISM: Artificial Sequence
<220> FEATURE:
<223> OTHER INFORMATION: Immunostimulatory polynucleotide
<220> FEATURE:
<221> NAME/KEY: misc_feature
<222> LOCATION: 1
<223> OTHER INFORMATION: n = A, T, C or G and base is complementary to base 10
<220> FEATURE:
<221> NAME/KEY: misc_feature
<222> LOCATION: 2
<223> OTHER INFORMATION: n = A, T, C or G and base is complementary to base 9
<220> FEATURE:
<221> NAME/KEY: misc_feature
<222> LOCATION: 5
<223> OTHER INFORMATION: n = A, T, C or G and base is complementary to base 6
<220> FEATURE:
<221> NAME/KEY: misc_feature
<222> LOCATION: 6
<223> OTHER INFORMATION: n = A, T, C or G and base is complementary to base 5
<220> FEATURE:
<221> NAME/KEY: misc_feature
<222> LOCATION: 9
<223> OTHER INFORMATION: n = A, T, C or G and base is complementary to base 2
<220> FEATURE:
<221> NAME/KEY: misc_feature
<222> LOCATION: 10
<223> OTHER INFORMATION: n = A, T, C or G and base is complementary to base 1

<400> SEQUENCE: 12 nncgnncgnn        10

<210> SEQ ID NO 13
<211> LENGTH: 12
<212> TYPE: DNA
<213> ORGANISM: Artificial Sequence
<220> FEATURE:
<223> OTHER INFORMATION: Immunostimulatory polynucleotide
<220> FEATURE:
<221> NAME/KEY: misc_feature
<222> LOCATION: 1
<223> OTHER INFORMATION: n = A, T, C or G and base is complementary to base 10
<220> FEATURE:
<221> NAME/KEY: misc_feature
<222> LOCATION: 2
<223> OTHER INFORMATION: n = A, T, C or G and base is complementary to base 9
<220> FEATURE:
<221> NAME/KEY: misc_feature
<222> LOCATION: 5
<223> OTHER INFORMATION: n = A, T, C or G and base is complementary to base 6
<220> FEATURE:
<221> NAME/KEY: misc_feature
<222> LOCATION: 6
<223> OTHER INFORMATION: n = A, T, C or G and base is complementary to base 5
<220> FEATURE:
<221> NAME/KEY: misc_feature
<222> LOCATION: 9
<223> OTHER INFORMATION: n = A, T, C or G and base is complementary to base 2

```
<220> FEATURE:
<221> NAME/KEY: misc_feature
<222> LOCATION: 10
<223> OTHER INFORMATION: n = A, T, C or G and base is complementary to
      base 1
<220> FEATURE:
<221> NAME/KEY: misc_feature
<222> LOCATION: (11)...(12)
<223> OTHER INFORMATION: Bases 11-12 may be absent

<400> SEQUENCE: 13
nncgnncgnn cg                                                             12

<210> SEQ ID NO 14
<211> LENGTH: 18
<212> TYPE: DNA
<213> ORGANISM: Artificial Sequence
<220> FEATURE:
<223> OTHER INFORMATION: Immunostimulatory polynucleotide
<220> FEATURE:
<221> NAME/KEY: misc_feature
<222> LOCATION: (1)...(3)
<223> OTHER INFORMATION: n = absent, A, T, C or G
<220> FEATURE:
<221> NAME/KEY: misc_feature
<222> LOCATION: (7)...(8)
<223> OTHER INFORMATION: n = absent, A, T, C or G
<220> FEATURE:
<221> NAME/KEY: misc_feature
<222> LOCATION: (4)...(8)
<223> OTHER INFORMATION: Sequence of bases 4-8 may be repeated up to 4
      times
<220> FEATURE:
<221> NAME/KEY: misc_feature
<222> LOCATION: (9)...(10)
<223> OTHER INFORMATION: n = absent, A, T, C or G
<220> FEATURE:
<221> NAME/KEY: misc_feature
<222> LOCATION: 11
<223> OTHER INFORMATION: n = A, T, C or G and base is complementary to
      base 16
<220> FEATURE:
<221> NAME/KEY: misc_feature
<222> LOCATION: 12
<223> OTHER INFORMATION: n = A, T, C or G and base is complementary to
      base 15
<220> FEATURE:
<221> NAME/KEY: misc_feature
<222> LOCATION: 15
<223> OTHER INFORMATION: n = A, T, C or G and base is complementary to
      base 12
<220> FEATURE:
<221> NAME/KEY: misc_feature
<222> LOCATION: 16
<223> OTHER INFORMATION: n = A, T, C or G and base is complementary to
      base 11
<220> FEATURE:
<221> NAME/KEY: misc_feature
<222> LOCATION: (17)...(18)
<223> OTHER INFORMATION: Bases 17-18 may be absent
<220> FEATURE:
<221> NAME/KEY: misc_feature
<222> LOCATION: (11)...(18)
<223> OTHER INFORMATION: Sequence of bases 11-18 may be repeated up to
      20 times

<400> SEQUENCE: 14
nnntcgnnnn nncgnncg                                                       18

<210> SEQ ID NO 15
<211> LENGTH: 24
<212> TYPE: DNA
<213> ORGANISM: Artificial Sequence
<220> FEATURE:
<223> OTHER INFORMATION: Immunostimulatory polynucleotide
<220> FEATURE:
```

```
<221> NAME/KEY: misc_feature
<222> LOCATION: (1)...(3)
<223> OTHER INFORMATION: n = absent, A, T, C or G
<220> FEATURE:
<221> NAME/KEY: misc_feature
<222> LOCATION: (7)...(8)
<223> OTHER INFORMATION: n = absent, A, T, C or G
<220> FEATURE:
<221> NAME/KEY: misc_feature
<222> LOCATION: (4)...(8)
<223> OTHER INFORMATION: Sequence of bases 4-8 may be repeated up to 4
      times
<220> FEATURE:
<221> NAME/KEY: misc_feature
<222> LOCATION: (9)...(10)
<223> OTHER INFORMATION: n = absent, A, T, C or G
<220> FEATURE:
<221> NAME/KEY: misc_feature
<222> LOCATION: 11
<223> OTHER INFORMATION: n = A, T, C or G and base is complementary to
      base 22
<220> FEATURE:
<221> NAME/KEY: misc_feature
<222> LOCATION: 12
<223> OTHER INFORMATION: n = A, T, C or G and base is complementary to
      base 21
<220> FEATURE:
<221> NAME/KEY: misc_feature
<222> LOCATION: 13
<223> OTHER INFORMATION: n = A, T, C or G and base is complementary to
      base 20
<220> FEATURE:
<221> NAME/KEY: misc_feature
<222> LOCATION: 14
<223> OTHER INFORMATION: n = A, T, C or G and base is complementary to
      base 19
<220> FEATURE:
<221> NAME/KEY: misc_feature
<222> LOCATION: 15
<223> OTHER INFORMATION: n = A, T, C or G and base is complementary to
      base 18
<220> FEATURE:
<221> NAME/KEY: misc_feature
<222> LOCATION: 18
<223> OTHER INFORMATION: n = A, T, C or G and base is complementary to
      base 15
<220> FEATURE:
<221> NAME/KEY: misc_feature
<222> LOCATION: 19
<223> OTHER INFORMATION: n = A, T, C or G and base is complementary to
      base 14
<220> FEATURE:
<221> NAME/KEY: misc_feature
<222> LOCATION: 20
<223> OTHER INFORMATION: n = A, T, C or G and base is complementary to
      base 13
<220> FEATURE:
<221> NAME/KEY: misc_feature
<222> LOCATION: 21
<223> OTHER INFORMATION: n = A, T, C or G and base is complementary to
      base 12
<220> FEATURE:
<221> NAME/KEY: misc_feature
<222> LOCATION: 22
<223> OTHER INFORMATION: n = A, T, C or G and base is complementary to
      base 11
<220> FEATURE:
<221> NAME/KEY: misc_feature
<222> LOCATION: (23)...(24)
<223> OTHER INFORMATION: Bases 23-24 may be absent
<220> FEATURE:
<221> NAME/KEY: misc_feature
<222> LOCATION: (11)...(24)
<223> OTHER INFORMATION: Sequence of bases 11-24 may be repeated up to
      20 times

<400> SEQUENCE: 15
nnntcgnnnn nnnnncgnnn nncg                                    24
```

```
<210> SEQ ID NO 16
<211> LENGTH: 12
<212> TYPE: DNA
<213> ORGANISM: Artificial Sequence
<220> FEATURE:
<223> OTHER INFORMATION: Immunostimulatory polynucleotide
<220> FEATURE:
<221> NAME/KEY: misc_feature
<222> LOCATION: 1
<223> OTHER INFORMATION: n = A, T, C or G and base is complementary to
      base 12
<220> FEATURE:
<221> NAME/KEY: misc_feature
<222> LOCATION: 2
<223> OTHER INFORMATION: n = A, T, C or G and base is complementary to
      base 11
<220> FEATURE:
<221> NAME/KEY: misc_feature
<222> LOCATION: 3
<223> OTHER INFORMATION: n = A, T, C or G and base is complementary to
      base 10
<220> FEATURE:
<221> NAME/KEY: misc_feature
<222> LOCATION: 4
<223> OTHER INFORMATION: n = A, T, C or G and base is complementary to
      base 9
<220> FEATURE:
<221> NAME/KEY: misc_feature
<222> LOCATION: 5
<223> OTHER INFORMATION: n = A, T, C or G and base is complementary to
      base 8
<220> FEATURE:
<221> NAME/KEY: misc_feature
<222> LOCATION: 8
<223> OTHER INFORMATION: n = A, T, C or G and base is complementary to
      base 5
<220> FEATURE:
<221> NAME/KEY: misc_feature
<222> LOCATION: 9
<223> OTHER INFORMATION: n = A, T, C or G and base is complementary to
      base 4
<220> FEATURE:
<221> NAME/KEY: misc_feature
<222> LOCATION: 10
<223> OTHER INFORMATION: n = A, T, C or G and base is complementary to
      base 3
<220> FEATURE:
<221> NAME/KEY: misc_feature
<222> LOCATION: 11
<223> OTHER INFORMATION: n = A, T, C or G and base is complementary to
      base 2
<220> FEATURE:
<221> NAME/KEY: misc_feature
<222> LOCATION: 12
<223> OTHER INFORMATION: n = A, T, C or G and base is complementary to
      base 1

<400> SEQUENCE: 16
nnnnncgnnn nn                                                           12

<210> SEQ ID NO 17
<211> LENGTH: 14
<212> TYPE: DNA
<213> ORGANISM: Artificial Sequence
<220> FEATURE:
<223> OTHER INFORMATION: Immunostimulatory polynucleotide
<220> FEATURE:
<221> NAME/KEY: misc_feature
<222> LOCATION: 1
<223> OTHER INFORMATION: n = A, T, C or G and base is complementary to
      base 12
<220> FEATURE:
<221> NAME/KEY: misc_feature
<222> LOCATION: 2
<223> OTHER INFORMATION: n = A, T, C or G and base is complementary to
      base 11
<220> FEATURE:
```

```
<221> NAME/KEY: misc_feature
<222> LOCATION: 3
<223> OTHER INFORMATION: n = A, T, C or G and base is complementary to
      base 10
<220> FEATURE:
<221> NAME/KEY: misc_feature
<222> LOCATION: 4
<223> OTHER INFORMATION: n = A, T, C or G and base is complementary to
      base 9
<220> FEATURE:
<221> NAME/KEY: misc_feature
<222> LOCATION: 5
<223> OTHER INFORMATION: n = A, T, C or G and base is complementary to
      base 8
<220> FEATURE:
<221> NAME/KEY: misc_feature
<222> LOCATION: 8
<223> OTHER INFORMATION: n = A, T, C or G and base is complementary to
      base 5
<220> FEATURE:
<221> NAME/KEY: misc_feature
<222> LOCATION: 9
<223> OTHER INFORMATION: n = A, T, C or G and base is complementary to
      base 4
<220> FEATURE:
<221> NAME/KEY: misc_feature
<222> LOCATION: 10
<223> OTHER INFORMATION: n = A, T, C or G and base is complementary to
      base 3
<220> FEATURE:
<221> NAME/KEY: misc_feature
<222> LOCATION: 11
<223> OTHER INFORMATION: n = A, T, C or G and base is complementary to
      base 2
<220> FEATURE:
<221> NAME/KEY: misc_feature
<222> LOCATION: 12
<223> OTHER INFORMATION: n = A, T, C or G and base is complementary to
      base 1
<220> FEATURE:
<221> NAME/KEY: misc_feature
<222> LOCATION: (13)...(14)
<223> OTHER INFORMATION: Bases 13-14 may be absent

<400> SEQUENCE: 17
nnnnncgnnn nncg                                                         14

<210> SEQ ID NO 18
<211> LENGTH: 20
<212> TYPE: DNA
<213> ORGANISM: Artificial Sequence
<220> FEATURE:
<223> OTHER INFORMATION: Immunostimulatory polynucleotide
<220> FEATURE:
<221> NAME/KEY: misc_feature
<222> LOCATION: (1)...(3)
<223> OTHER INFORMATION: n = absent, A, T, C or G
<220> FEATURE:
<221> NAME/KEY: misc_feature
<222> LOCATION: (7)...(8)
<223> OTHER INFORMATION: n = absent, A, T, C or G
<220> FEATURE:
<221> NAME/KEY: misc_feature
<222> LOCATION: (4)...(8)
<223> OTHER INFORMATION: Sequence of bases 4-8 may be repeated up to 4
      times
<220> FEATURE:
<221> NAME/KEY: misc_feature
<222> LOCATION: (9)...(10)
<223> OTHER INFORMATION: n = absent, A, T, C or G
<220> FEATURE:
<221> NAME/KEY: misc_feature
<222> LOCATION: 11
<223> OTHER INFORMATION: n = A, T, C or G and base is complementary to
      base 18
<220> FEATURE:
<221> NAME/KEY: misc_feature
<222> LOCATION: 12
```

```
<223> OTHER INFORMATION: n = A, T, C or G and base is complementary to
      base 17
<220> FEATURE:
<221> NAME/KEY: misc_feature
<222> LOCATION: 17
<223> OTHER INFORMATION: n = A, T, C or G and base is complementary to
      base 12
<220> FEATURE:
<221> NAME/KEY: misc_feature
<222> LOCATION: 18
<223> OTHER INFORMATION: n = A, T, C or G and base is complementary to
      base 11
<220> FEATURE:
<221> NAME/KEY: misc_feature
<222> LOCATION: (19)...(20)
<223> OTHER INFORMATION: Bases 19-20 may be absent
<220> FEATURE:
<221> NAME/KEY: misc_feature
<222> LOCATION: (11)...(20)
<223> OTHER INFORMATION: Sequence of bases 11-20 may be repeated up to
      20 times

<400> SEQUENCE: 18
nnntcgnnnn nncgcgnncg                                              20

<210> SEQ ID NO 19
<211> LENGTH: 10
<212> TYPE: DNA
<213> ORGANISM: Artificial Sequence
<220> FEATURE:
<223> OTHER INFORMATION: Immunostimulatory polynucleotide
<220> FEATURE:
<221> NAME/KEY: misc_feature
<222> LOCATION: 1
<223> OTHER INFORMATION: n = A, T, C or G and base is complementary to
      base 8
<220> FEATURE:
<221> NAME/KEY: misc_feature
<222> LOCATION: 2
<223> OTHER INFORMATION: n = A, T, C or G and base is complementary to
      base 7
<220> FEATURE:
<221> NAME/KEY: misc_feature
<222> LOCATION: 7
<223> OTHER INFORMATION: n = A, T, C or G and base is complementary to
      base 2
<220> FEATURE:
<221> NAME/KEY: misc_feature
<222> LOCATION: 8
<223> OTHER INFORMATION: n = A, T, C or G and base is complementary to
      base 1
<220> FEATURE:
<221> NAME/KEY: misc_feature
<222> LOCATION: (9)...(10)
<223> OTHER INFORMATION: Bases 9-10 may be absent

<400> SEQUENCE: 19 nncgcgnncg                                                         10

<210> SEQ ID NO 20
<211> LENGTH: 22
<212> TYPE: DNA
<213> ORGANISM: Artificial Sequence
<220> FEATURE:
<223> OTHER INFORMATION: Immunostimulatory polynucleotide
<220> FEATURE:
<221> NAME/KEY: misc_feature
<222> LOCATION: (1)...(3)
<223> OTHER INFORMATION: n = absent, A, T, C or G
<220> FEATURE:
<221> NAME/KEY: misc_feature
<222> LOCATION: (7)...(8)
<223> OTHER INFORMATION: n = absent, A, T, C or G
<220> FEATURE:
<221> NAME/KEY: misc_feature
<222> LOCATION: (4)...(8)
```

<223> OTHER INFORMATION: Sequence of bases 4-8 may be repeated up to 4
      times
<220> FEATURE:
<221> NAME/KEY: misc_feature
<222> LOCATION: (9)...(10)
<223> OTHER INFORMATION: n = absent, A, T, C or G
<220> FEATURE:
<221> NAME/KEY: misc_feature
<222> LOCATION: 11
<223> OTHER INFORMATION: n = A, T, C or G and base is complementary to
      base 20
<220> FEATURE:
<221> NAME/KEY: misc_feature
<222> LOCATION: 12
<223> OTHER INFORMATION: n = A, T, C or G and base is complementary to
      base 19
<220> FEATURE:
<221> NAME/KEY: misc_feature
<222> LOCATION: 13
<223> OTHER INFORMATION: n = A, T, C or G and base is complementary to
      base 18
<220> FEATURE:
<221> NAME/KEY: misc_feature
<222> LOCATION: 18
<223> OTHER INFORMATION: n = A, T, C or G and base is complementary to
      base 13
<220> FEATURE:
<221> NAME/KEY: misc_feature
<222> LOCATION: 19
<223> OTHER INFORMATION: n = A, T, C or G and base is complementary to
      base 12
<220> FEATURE:
<221> NAME/KEY: misc_feature
<222> LOCATION: 20
<223> OTHER INFORMATION: n = A, T, C or G and base is complementary to
      base 11
<220> FEATURE:
<221> NAME/KEY: misc_feature
<222> LOCATION: (21)...(22)
<223> OTHER INFORMATION: Bases 21-22 may be absent
<220> FEATURE:
<221> NAME/KEY: misc_feature
<222> LOCATION: (11)...(22)
<223> OTHER INFORMATION: Sequence of bases 11-22 may be repeated up to
      20 times

<400> SEQUENCE: 20
nnntcgnnnn nnncgcgnnn cg                                              22

<210> SEQ ID NO 21
<211> LENGTH: 10
<212> TYPE: DNA
<213> ORGANISM: Artificial Sequence
<220> FEATURE:
<223> OTHER INFORMATION: Immunostimulatory polynucleotide
<220> FEATURE:
<221> NAME/KEY: misc_feature
<222> LOCATION: 1
<223> OTHER INFORMATION: n = A, T, C or G and base is complementary to
      base 10
<220> FEATURE:
<221> NAME/KEY: misc_feature
<222> LOCATION: 2
<223> OTHER INFORMATION: n = A, T, C or G and base is complementary to
      base 9
<220> FEATURE:
<221> NAME/KEY: misc_feature
<222> LOCATION: 3
<223> OTHER INFORMATION: n = A, T, C or G and base is complementary to
      base 8
<220> FEATURE:
<221> NAME/KEY: misc_feature
<222> LOCATION: 8
<223> OTHER INFORMATION: n = A, T, C or G and base is complementary to
      base 3
<220> FEATURE:
<221> NAME/KEY: misc_feature
<222> LOCATION: 9

```
<223> OTHER INFORMATION: n = A, T, C or G and base is complementary to
      base 2
<220> FEATURE:
<221> NAME/KEY: misc_feature
<222> LOCATION: 10
<223> OTHER INFORMATION: n = A, T, C or G and base is complementary to
      base 1

<400> SEQUENCE: 21 nnncgcgnnn                                                              10

<210> SEQ ID NO 22
<211> LENGTH: 12
<212> TYPE: DNA
<213> ORGANISM: Artificial Sequence
<220> FEATURE:
<223> OTHER INFORMATION: Immunostimulatory polynucleotide
<220> FEATURE:
<221> NAME/KEY: misc_feature
<222> LOCATION: 1
<223> OTHER INFORMATION: n = A, T, C or G and base is complementary to
      base 10
<220> FEATURE:
<221> NAME/KEY: misc_feature
<222> LOCATION: 2
<223> OTHER INFORMATION: n = A, T, C or G and base is complementary to
      base 9
<220> FEATURE:
<221> NAME/KEY: misc_feature
<222> LOCATION: 3
<223> OTHER INFORMATION: n = A, T, C or G and base is complementary to
      base 8
<220> FEATURE:
<221> NAME/KEY: misc_feature
<222> LOCATION: 8
<223> OTHER INFORMATION: n = A, T, C or G and base is complementary to
      base 3
<220> FEATURE:
<221> NAME/KEY: misc_feature
<222> LOCATION: 9
<223> OTHER INFORMATION: n = A, T, C or G and base is complementary to
      base 2
<220> FEATURE:
<221> NAME/KEY: misc_feature
<222> LOCATION: 10
<223> OTHER INFORMATION: n = A, T, C or G and base is complementary to
      base 1
<220> FEATURE:
<221> NAME/KEY: misc_feature
<222> LOCATION: (11)...(12)
<223> OTHER INFORMATION: Bases 11-12 may be absent

<400> SEQUENCE: 22
nnncgcgnnn cg                                                           12

<210> SEQ ID NO 23
<211> LENGTH: 20
<212> TYPE: DNA
<213> ORGANISM: Artificial Sequence
<220> FEATURE:
<223> OTHER INFORMATION: Immunostimulatory polynucleotide
<220> FEATURE:
<221> NAME/KEY: misc_feature
<222> LOCATION: (1)...(3)
<223> OTHER INFORMATION: n = absent, A, T, C or G
<220> FEATURE:
<221> NAME/KEY: misc_feature
<222> LOCATION: (7)...(8)
<223> OTHER INFORMATION: n = absent, A, T, C or G
<220> FEATURE:
<221> NAME/KEY: misc_feature
<222> LOCATION: (4)...(8)
<223> OTHER INFORMATION: Sequence of bases 4-8 may be repeated up to 4
      times
<220> FEATURE:
<221> NAME/KEY: misc_feature
```

```
<222> LOCATION: (9)...(10)
<223> OTHER INFORMATION: n = absent, A, T, C or G
<220> FEATURE:
<221> NAME/KEY: misc_feature
<222> LOCATION: 13
<223> OTHER INFORMATION: n = A, T, C or G and base is complementary to
      base 16
<220> FEATURE:
<221> NAME/KEY: misc_feature
<222> LOCATION: 14
<223> OTHER INFORMATION: n = A, T, C or G and base is complementary to
      base 15
<220> FEATURE:
<221> NAME/KEY: misc_feature
<222> LOCATION: 15
<223> OTHER INFORMATION: n = A, T, C or G and base is complementary to
      base 14
<220> FEATURE:
<221> NAME/KEY: misc_feature
<222> LOCATION: 16
<223> OTHER INFORMATION: n = A, T, C or G and base is complementary to
      base 13
<220> FEATURE:
<221> NAME/KEY: misc_feature
<222> LOCATION: (19)...(20)
<223> OTHER INFORMATION: Bases 19-20 may be absent
<220> FEATURE:
<221> NAME/KEY: misc_feature
<222> LOCATION: (11)...(20)
<223> OTHER INFORMATION: Sequence of bases 11-20 may be repeated up to
      20 times

<400> SEQUENCE: 23
nnntcgnnnn cgnnnncgcg                                                      20

<210> SEQ ID NO 24
<211> LENGTH: 10
<212> TYPE: DNA
<213> ORGANISM: Artificial Sequence
<220> FEATURE:
<223> OTHER INFORMATION: Immunostimulatory polynucleotide
<220> FEATURE:
<221> NAME/KEY: misc_feature
<222> LOCATION: 3
<223> OTHER INFORMATION: n = A, T, C or G and base is complementary to
      base 6
<220> FEATURE:
<221> NAME/KEY: misc_feature
<222> LOCATION: 4
<223> OTHER INFORMATION: n = A, T, C or G and base is complementary to
      base 5
<220> FEATURE:
<221> NAME/KEY: misc_feature
<222> LOCATION: 5
<223> OTHER INFORMATION: n = A, T, C or G and base is complementary to
      base 4
<220> FEATURE:
<221> NAME/KEY: misc_feature
<222> LOCATION: 6
<223> OTHER INFORMATION: n = A, T, C or G and base is complementary to
      base 3
<220> FEATURE:
<221> NAME/KEY: misc_feature
<222> LOCATION: (9)...(10)
<223> OTHER INFORMATION: Bases 9-10 may be absent

<400> SEQUENCE: 24 cgnnnncgcg                                                                 10

<210> SEQ ID NO 25
<211> LENGTH: 9
<212> TYPE: PRT
<213> ORGANISM: Artificial Sequence
<220> FEATURE:
<223> OTHER INFORMATION: Synthetic Construct
```

```
<400> SEQUENCE: 25

Lys Phe Phe Lys Phe Phe Lys Phe Phe
1               5

<210> SEQ ID NO 26
<211> LENGTH: 30
<212> TYPE: PRT
<213> ORGANISM: Artificial Sequence
<220> FEATURE:
<223> OTHER INFORMATION: Synthetic Construct

<400> SEQUENCE: 26

Trp Glu Ala Lys Leu Ala Lys Ala Leu Ala Lys Ala Leu Ala Lys His
1               5                   10                  15

Leu Ala Lys Ala Leu Ala Lys Ala Leu Glu Ala Cys Glu Ala
            20                  25                  30

<210> SEQ ID NO 27
<211> LENGTH: 30
<212> TYPE: PRT
<213> ORGANISM: Artificial Sequence
<220> FEATURE:
<223> OTHER INFORMATION: Synthetic Construct

<400> SEQUENCE: 27

Trp Glu Ala Lys Leu Ala Lys Ala Leu Ala Lys Ala Leu Ala Lys His
1               5                   10                  15

Leu Ala Lys Ala Leu Ala Lys Ala Leu Lys Ala Cys Glu Ala
            20                  25                  30

<210> SEQ ID NO 28
<211> LENGTH: 8
<212> TYPE: DNA
<213> ORGANISM: Artificial Sequence
<220> FEATURE:
<223> OTHER INFORMATION: Immunostimulatory polynucleotide
<220> FEATURE:
<221> NAME/KEY: misc_feature
<222> LOCATION: 1
<223> OTHER INFORMATION: n = A, T, C or G and base is complementary to
      base 6
<220> FEATURE:
<221> NAME/KEY: misc_feature
<222> LOCATION: 2
<223> OTHER INFORMATION: n = A, T, C or G and base is complementary to
      base 5
<220> FEATURE:
<221> NAME/KEY: misc_feature
<222> LOCATION: 5
<223> OTHER INFORMATION: n = A, T, C or G and base is complementary to
      base 2
<220> FEATURE:
<221> NAME/KEY: misc_feature
<222> LOCATION: 6
<223> OTHER INFORMATION: n = A, T, C or G and base is complementary to
      base 1
<220> FEATURE:
<221> NAME/KEY: misc_feature
<222> LOCATION: (7)...(8)
<223> OTHER INFORMATION: Bases 7-8 may be absent
<220> FEATURE:
<221> NAME/KEY: misc_feature
<222> LOCATION: (1)...(8)
<223> OTHER INFORMATION: Sequence of bases 1-8 may be repeated up to 20
      times

<400> SEQUENCE: 28 nncgnncg                                                                     8
```

LONG TERM DISEASE MODIFICATION USING IMMUNOSTIMULATORY OLIGONUCLEOTIDES

RELATED APPLICATIONS

This application claims priority benefit of provisional patent application No. 60/865,089, filed on Nov. 9, 2006, the disclosure of which is herein incorporated by reference in its entirety.

FIELD OF THE INVENTION

The invention relates to methods for treating asthma by using multiple administrations of one or more immunostimulatory sequences ("ISS") that confer long term disease modification.

BACKGROUND OF THE INVENTION

The type of immune response generated by infection or other antigenic challenge can generally be distinguished by the subset of T helper (Th) cells involved in the response. The Th1 subset is responsible for classical cell-mediated functions such as delayed-type hypersensitivity and activation of cytotoxic T lymphocytes (CTLs), whereas the Th2 subset functions more effectively as a helper for B-cell activation. The type of immune response to an antigen is generally influenced by the cytokines produced by the cells responding to the antigen. Differences in the cytokines secreted by Th1 and Th2 cells are believed to reflect different biological functions of these two subsets. See, for example, Romagnani (2000) *Ann. Allergy Asthma Immunol.*, 85:9-18.

The Th1 subset may be particularly suited to respond to viral infections, intracellular pathogens, and tumor cells because it secretes IL-2 and IFN-γ, which activate CTLs. The Th2 subset may be more suited to respond to free-living bacteria and helminthic parasites and may mediate allergic reactions, since IL-4 and IL-5 are known to induce IgE production and eosinophil activation, respectively. In general, Th1 and Th2 cells secrete distinct patterns of cytokines and so one type of response can moderate the activity of the other type of response. A shift in the Th1/Th2 balance can result in an allergic response, for example, or, alternatively, in an increased CTL response.

It has been recognized for some time that a Th1-type immune response can be induced in mammals by administration of certain ISSs. The ISSs include sequences referred to as immunostimulatory sequences ("ISS"), often including a CG. See, e.g., PCT Publications WO 98/55495, WO 97/28259, U.S. Pat. Nos. 6,194,388; 6,207,646, and 6,498,148; and Krieg et al. (1995) *Nature*, 374:546-49. For many infectious diseases, such as tuberculosis and malaria, Th2-type responses are of little protective value against infection. Protein-based vaccines typically induce Th2-type immune responses, characterized by high titers of neutralizing antibodies but without significant cell-mediated immunity. Moreover, some types of antibody responses are inappropriate in certain indications, most notably in allergy where an IgE antibody response can result in anaphylactic shock.

In vertebrates, endothelial cell adhesion by granulocytes (eosinophils, basophils, neutrophils and mast cells) is followed by the release of inflammatory mediators, such as leukotrienes, major basic protein and histamine. In susceptible individuals, the resulting inflammation can damage affected individual tissues.

The most common pathologic inflammatory condition is asthma, which is characterized by marked eosinophil infiltration into respiratory airways, followed by inflammation-induced tissue damage. Routine treatment of such conditions is typically directed toward inhibiting the activity of inflammatory mediators released after granulocyte adhesion to endothelia (e.g., by delivering a corticoid composition to the affected tissues). Where the identity of an inflammation inducing antigen is known, some immune protection against further antigen challenge can be provided through immunization. However, although effective in stimulating production of neutralizing antibodies, canonical immunization does not effectively stimulate longer term cellular immunity. Moreover, antigen immunization stimulates individual production of IL-4 and IL-5. IL-5 encourages granulocyte adhesion to endothelia while IL-4 induces immunoglobulin switching to the IgE isotype at the risk of anaphylaxis.

With respect to allergic asthma, it has been shown that pretreatment with ISS inhibits allergen-induced airway eosinophilia and airway hyperresponsiveness in a mouse model for allergic asthma. Broide et al. (1998) *J. Immunol.* 161:7054. It also has been shown that this inhibition also correlates with ISS-induced down-regulation of Th2-type cytokine levels in the airways. Hessel et al., (2005) *J. Exp. Med.,* 202(11):1563. These effects, however, focused on the direct effects of ISS treatment since the ISS treatment was given shortly before the allergen challenge. However, the effects of long-term treatment with ISS are remains largely unknown. In addition, a treatment for asthma that could confer long term benefits has not been well-characterized either. The invention disclosed herein provides teachings useful to address the foregoing.

All patents, patent applications, and publications cited herein are hereby incorporated by reference in their entirety.

BRIEF SUMMARY OF THE INVENTION

The invention provides for methods for treating asthma in an individual in need thereof by administering to the individual multiple administrations of an effective amount of an ISS. In one embodiment, the ISS is administered at least 3 times. In another embodiment, the multiple administrations occur on a weekly basis. In another embodiment, the method results in long term disease modification of asthma. In another embodiment, the long term disease modification is a decrease of Th2 response in the individual. In another embodiment, the decrease of Th2 response in the individual is a decrease of any one of the cytokines selected from the group consisting of IL-4, IL-5, IL-10, and IL-13. In another embodiment, the long term disease modification lasts at least 13 weeks after the last administration of the ISS. In another embodiment, the method results in long term disease modification of asthma wherein the asthma is allergic asthma. In another embodiment, the ISS is selected from the group consisting of 1018 ISS, a CpG containing ISS, and a chimeric immunomodulatory compound. In another embodiment, the ISS is 1018 ISS. In another embodiment, the ISS is administered in the presence of an adventitious allergen. In another embodiment, the adventitious allergen is ragweed.

BRIEF DESCRIPTION OF THE DRAWINGS

FIG. 3 is a graph that depicts levels of the Th2-type cytokines IL-4 and IL-13 detected in BAL fluid. The double asterisks indicate a statistical significance of $p<0.01$. The single asterisk indicates a statistical significance of $p<0.05$.

FIG. 4 is a graph that depicts levels of the Th2-type cytokine IL-10 and Th1 type cytokine INF-γ detected in BAL fluid. The double asterisks indicate a statistical significance of $p<0.01$.

DETAILED DESCRIPTION OF THE INVENTION

Figure 1:
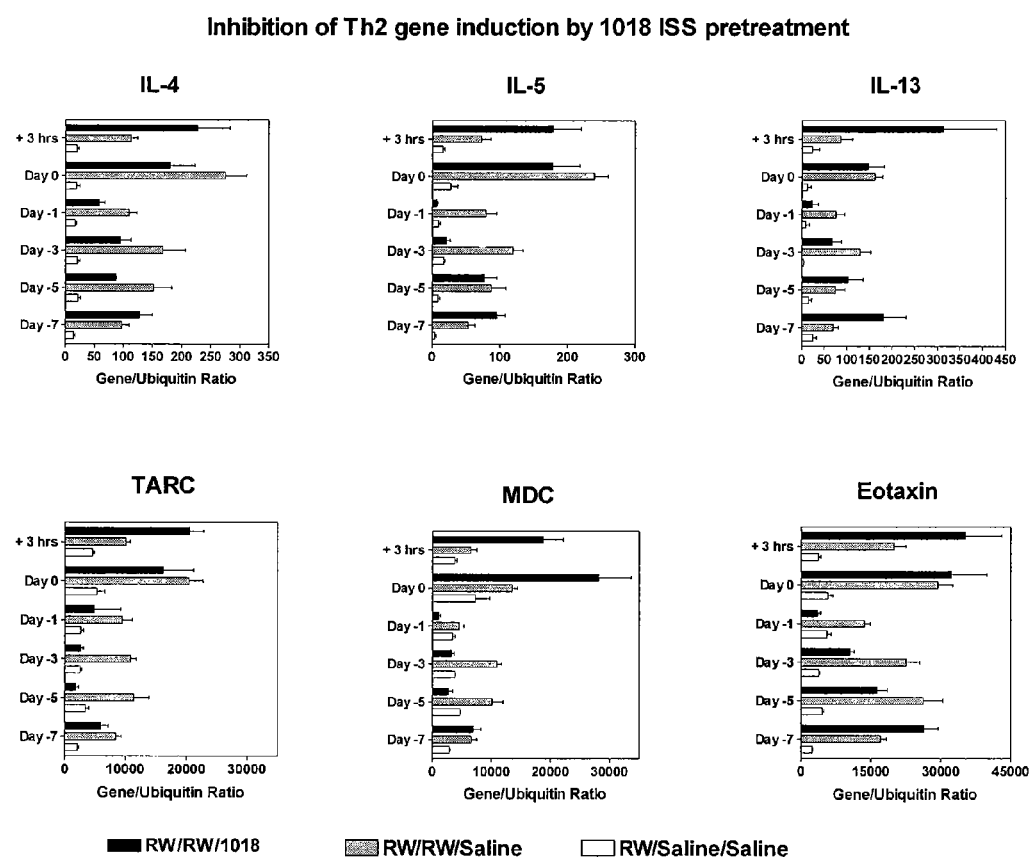
FIG. 1 is a graph that depicts results for six genes ISS important for the development of a Th2-type airway inflammatory response when sensitized mice are challenged intranasally with ragweed. The data are expressed as gene/ubiquitin ratio.

The invention herein provides method for treating asthma in an individual by administering an effective amount of an immunostimulatory sequence (ISS) over multiple administrations to the individual. In one aspect of the invention, long term disease modification can be conferred by using multiple administrations of ISS. Long term disease modification includes the suppression of a Th2 response in the individual. In some cases, the suppression is an inhibition of a Th2 response.

General Methods

The practice of the present invention will employ, unless otherwise indicated, conventional techniques of molecular biology (including recombinant techniques), microbiology, cell biology, biochemistry, nucleic acid chemistry, and immunology, which are within the skill of the art. Such techniques are explained fully in the literature, such as, *Molecular Cloning: A Laboratory Manual*, second edition (Sambrook et al., 1989) and *Molecular Cloning: A Laboratory Manual*, third edition (Sambrook and Russel, 2001), jointly and individually referred to herein as "Sambrook"); *Oligonucleotide Synthesis* (M. J. Gait, ed., 1984); *Animal Cell Culture* (R. I. Freshney, ed., 1987); *Handbook of Experimental Immunology* (D. M. Weir & C. C. Blackwell, eds.); *Gene Transfer Vectors for Mammalian Cells* (J. M. Miller & M. P. Calos, eds., 1987); *Current Protocols in Molecular Biology* (F. M. Ausubel et al., eds., 1987, including supplements through 2001); *PCR: The Polymerase Chain Reaction*, (Mullis et al., eds., 1994); *Current Protocols in Immunology* (J. E. Coligan et al., eds., 1991); *The Immunoassay Handbook* (D. Wild, ed., Stockton Press NY, 1994); *Bioconjugate Techniques* (Greg T. Hermanson, ed., Academic Press, 1996); *Methods of Immunological Analysis* (R. Masseyeff, W. H. Albert, and N. A. Staines, eds., Weinheim: VCH Verlags gesellschaft mbH, 1993), Harlow and Lane (1988) *Antibodies, A Laboratory Manual*, Cold Spring Harbor Publications, New York, and Harlow and Lane (1999) *Using Antibodies: A Laboratory Manual* Cold Spring Harbor Laboratory Press, Cold Spring Harbor, NY (jointly and individually referred to herein as "Harlow and Lane"), Beaucage et al. eds., *Current Protocols in Nucleic Acid Chemistry* (John Wiley & Sons, Inc., New York, 2000); and Agrawal, ed., *Protocols for Oligonucleotides and Analogs, Synthesis and Properties* (Humana Press Inc., New Jersey, 1993).

DEFINITIONS

As used herein, the term "allergen" means an antigen or antigenic portion of a molecule, usually a protein, which elicits an allergic response upon exposure to a subject. Typically the subject is allergic to the allergen as indicated, for instance, by the wheal and flare test or any method known in the art. A molecule is said to be an allergen even if only a small subset of subjects exhibit an allergic immune response (e.g., IgE) upon exposure to the molecule. An allergen may be present in the environment in minute quantities or in larger quantities depending on the season. Examples of allergens are listed in Table 1 infra.

An "individual" is a vertebrate, such as mouse, and is preferably a mammal, more preferably a human. Mammals include, but are not limited to, humans, primates, farm animals, sport animals, rodents and pets.

An "effective amount" of a substance is that amount sufficient to effect beneficial or desired results, including clinical results, and, as such, an "effective amount" depends upon the context in which it is being applied. In the context of administering a composition that modulates an immune response, either with or without a co-administered antigen, an effective amount of an ISS (and antigen, if applicable) is an amount sufficient to achieve such a modulation as compared to the immune response obtained when the antigen is administered alone. An effective amount can confer long term benefits of disease modification, such as suppression and/or inhibition of Th2 immune response. An effective amount can be administered in one or more administrations.

As used herein, and as well-understood in the art, "treatment" is an approach for obtaining beneficial or desired results, including clinical results. For purposes of this invention, beneficial or desired clinical results include, but are not limited to, alleviation or amelioration of one or more symptoms, diminishment of extent of disease, stabilized (i.e., not worsening) state of disease, delay or slowing of disease progression, and/or amelioration or palliation of the disease state. "Treatment" can also mean prolonging survival as compared to expected survival if not receiving treatment.

As used herein, the term "long term disease modification" refers to the reduction or elimination of one or more asthma symptoms for a period of at least 3 weeks following administration of the last dose of ISS, preferably for a period of at least 8 weeks, most preferably for a period of at least 12 weeks. The asthma symptoms include, but are not limited to, bronchial hyperresponsiveness, eosinophil infiltration in the airways, mucus production in the airways, Th2 cytokines in the airways, airway remodeling, immediate asthmatic reaction (airway constriction immediately after allergen exposure), and late asthmatic reaction (airway constriction several hours after allergen exposure).

Biological Effects of ISS

It been observed that long term disease modification can be conferred on individuals with asthma by using multiple administrations of ISS. The examples provide some illustration of this observation. Example 1 discloses that the direct effects of one type of ISS, the 1018 ISS for example, lasts about one week in a murine model of allergic asthma. Examples 2 and 3 illustrate that the Th2 response can be suppressed in individuals to whom 1018 ISS has been multiply administered for at least 8 weeks. The long term effects of Th2 suppression can last at least 13 weeks. Thus, in one aspect, the invention provides for treating asthma long term by administering to an individual an effective amount of ISS for at least 8 weeks. This long term effect of the treatment can last at least 13 weeks. The invention contemplates methods for providing the long term benefits for individuals who may have asthma by using multiple administration of ISS for at least 8 weeks to confer long term disease modification that persists for at least 13, 15, 17, 19, 21 or 25 weeks.

Functionally, ISS enhance the cellular and humoral immune responses in an individual, particularly lymphocyte proliferation and the release of cytokines (including interferon or IFN) by individual monocytes and natural killer (NK) cells. Immunostimulation by synthetic ISS in vivo occurs by contacting individual lymphocytes with, for example ISS, ISS oligonucleotide conjugates and ISS-containing recombinant expression vectors. See, for example, U.S. Pat. No. 6,610,661 and WO 97/28259. Thus, while native microbial ISS stimulate the individual immune system to respond to infection, synthetic analogs of these ISS are useful therapeutically to modulate the individual immune response not only to microbial antigens, but also to allergens and other substances.

ISS Compositions

The method of this invention can be practiced by using any type of ISS. In one embodiment, the 1018 ISS is used. The structure of 1018 ISS has been published in multiple scientific articles as well as patents. See, for example, Hessel et al. (2005) *J. Exp. Med.*, 202(11):1563. In general, 1018 ISS is (5'-TGACTGTAACGTTCGAGATGA-3') (SEQ ID NO:1). In another embodiment, one or more ISS containing CpG motif(s) can be used. See, for example, U.S. Publication No. 2006/0058254 or WO 2004/058179. In another embodiment, one or more chimeric immunomodulatory compound ("CIC") can be used. See, for example, U.S. Publication No. 2004/0132677.

In accordance with the present invention, the ISS contains at least one palindromic sequence (i.e., palindrome) of at least 8 bases in length containing at least one CG dinucleotide. The ISS also contains at least one TCG trinucleotide sequence at or near the 5' end of the polynucleotide (i.e., 5'-TCG). In some instances, the palindromic sequence and the 5'-TCG are separated by 0, 1 or 2 bases in the ISS. In some instances the palindromic sequence includes all or part of the 5'-TCG.

ISSs have been described in the art and their activity may be readily identified using standard assays which indicate various aspects of the immune response, such as cytokine secretion, antibody production, NK cell activation, B cell proliferation, T cell proliferation. See, e.g., WO 97/28259; WO 98/16247; WO 99/11275; Krieg et al. (1995) *Nature* 374:546-549; Yamamoto et al. (1992a); Ballas et al. (1996); Klinman et al. (1997); Sato et al. (1996); Pisetsky (1996a); Shimada et al. (1986) *Jpn. J. Cancer Res.* 77:808-816; Cowdery et al. (1996) *J. Immunol.* 156:4570-4575; Roman et al. (1997); Lipford et al. (1997a); WO 98/55495 and WO 00/61151. Accordingly, these and other methods can be used to identify, test and/or confirm immunomodulatory ISSs.

The ISS can be of any length greater than 10 bases or base pairs, preferably greater than 15 bases or base pairs, more preferably greater than 20 bases or base pairs in length. It is understood that, with respect to formulae described herein, any and all parameters are independently selected. For example, if x=0-2, y may be independently selected regardless of the values of x (or any other selectable parameter in a formula).

In some embodiments, an ISS comprises (a) a palindromic sequence at least 8 bases in length which contains at least two CG dinucleotides, where the CG dinucleotides are separated from each other by 0, 1, 2, 3, 4 or 5 bases, and (b) a $(TCG)_y$ sequence positioned 0, 1, 2, or 3 bases from the 5' end of the polynucleotide, where y is 1 or 2, and where the 3' end of the $(TCG)_y$ sequence is separated from the 5' end of the palindromic sequence by 0, 1 or 2 bases. In some embodiments, a CG dinucleotide of the $(TCG)_y$ sequence of (b) may count for one of the at least two CG dinucleotides in the palindromic sequence of (a). In some embodiments, the CG dinucleotides of the palindromic sequence are separated from each other by 1, 3 or 4 bases. In some ISSs of the invention, whether described in this paragraph or elsewhere in the application, the palindromic sequence has a base composition of less than two-thirds G's and C's. In some embodiments, the palindromic sequence has a base composition of greater than one-third A's and T's.

In some embodiments, an ISS comprises (a) a palindromic sequence at least 8 bases in length which contains at least two CG dinucleotides, where the CG dinucleotides are separated from each other by 0, 1, 2, 3, 4 or 5 bases, and (b) a $(TCG)_y$ sequence positioned 0, 1, 2, or 3 bases from the 5' end of the polynucleotide, where y is 1 or 2, where the palindromic sequence includes all or part of the $(TCG)_y$ sequence, and where a CG dinucleotide of the $(TCG)_y$ sequence of (b) may count for one of the CG dinucleotides of the palindromic sequence of (a). Preferably, in some embodiments, the CG dinucleotides of the palindromic sequence are separated from each other by 1, 3 or 4 bases.

Accordingly, in some embodiments, an ISS may comprise a sequence of the formula: $5'-N_x(TCG(N_w))_y N_w(X_1CGX_1'(CG)_p)_z$ (SEQ ID NO: 2) wherein N are nucleosides with x=0-3, y=1-4, w=-1, 0, 1 or 2, p=0 or 1, q=0, 1 or 2, and z=1-20, wherein $X_1$ and $X_1'$ are self-complimentary and wherein the 5' T of the $(TCG(N_q))_y$ (SEQ ID NO: 3) sequence is 0-3 bases from the 5' end of the polynucleotide. The ISS further comprises a palindromic sequence 8 bases in length or greater wherein the palindromic sequence comprises at least one of the $(X_1CGX_1'(CG)_p)$ sequences. In an ISS with w=-1, the 3' base of the $(TCG(N_q))_y$ (SEQ ID NO: 3) sequence is the 5' $X_1$ of the first $(X_1CGX_1'(CG)_p)$ sequence. In some embodiments, the $(TCG(N_q))_y$ (SEQ ID NO: 3) sequence is separated from the palindromic sequence by 0, 1 or 2 bases. In other embodiments, the palindromic sequence includes all or part of the $(TCG(N_q))_y$ (SEQ ID NO: 3) sequence. In some embodiments, when p=0, $X_1$ is either A or T.

In some embodiments, an ISS may comprise a sequence of the formula: $5'-N_x(TCG(N_q))_y N_w(X_1X_2X_3CGX_3'X_2'X_1'(CG)_p)_z$ (SEQ ID NO: 4) wherein N are nucleosides with x=0-3, y=1-4, w=-3, -2, -1, 0, 1 or 2, p=0 or 1, q=0, 1 or 2, and z=1-20, wherein $X_1$ and $X_1'$, $X_2$ and $X_2'$, and $X_3$ and $X_3'$ are self-complimentary and wherein the 5' T of the $(TCG(N_q))_y$ (SEQ ID NO: 3) sequence is 0-3 bases from the 5' end of the polynucleotide. The ISS further comprises a palindromic sequence 8 bases in length or greater wherein the palindromic sequence comprises the first $(X_1X_2X_3CGX_3'X_2'X_1')$ of the at least one $(X_1X_2X_3CGX_3'X_2'X_1'(CG)_p)$ (SEQ ID NO: 5) sequence. In an ISS with w=-1, the 3' base of the $(TCG(N_q))_y$ (SEQ ID NO: 3) sequence is the 5' $X_1$ of the first $(X_1X_2X_3CGX_3'X_2'X_1'(CG)_p)$ (SEQ ID NO: 5) sequence. In an ISS with w=-2, the penultimate (i.e., second to last) and the ultimate (i.e., last) 3' bases of the $(TCG(N_q))_y$ (SEQ ID NO: 3) sequence are the 5' $X_1$ and $X_2$, respectively, of the first $(X_1X_2X_3CGX_3'X_2'X_1'(CG)_p)$ (SEQ ID NO: 5) sequence. In an ISS with w=-3, the antepenultimate (i.e., third to last), the penultimate (i.e., second to last) and the ultimate (i.e., last) 3' bases of the $(TCG(N_q))_y$ (SEQ ID NO: 3) sequence are the 5' $X_1$, $X_2$, and $X_3$, respectively, of the first $(X_1X_2X_3CGX_3'X_2'X_1'(CG)_p)$ (SEQ ID NO: 5) sequence. In some embodiments, the $(TCG(N_q))_y$ (SEQ ID NO: 3) sequence is separated from the palindromic sequence by 0, 1 or 2 bases. In other embodiments, the palindromic sequence includes all or part of the $(TCG(N_q))_y$ (SEQ ID NO: 3) sequence. In some embodiments, when p=1, $X_1$, $X_2$, and $X_3$ are each either A or T. In some embodiments, when p=0, at least two of $X_1$, $X_2$, and $X_3$ are either A or T.

In some embodiments, an ISS may comprise a sequence of the formula: 5'-$N_x(TCG(N_q))_yN_w$ $(X_1X_2X_3X_4CGX_4'X_3'X_2'X_1'(CG)_p)_z$ (SEQ ID NO: 6) wherein N are nucleosides with x=0-3, y=1-4, w=−3, −2, −1, 0, 1 or 2, p=0 or 1, q=0, 1 or 2, and z=1-20, wherein $X_1$ and $X_1'$, $X_2$ and $X_2'$, $X_3$ and $X_3'$, and $X_4$ and $X_4'$ are self-complimentary and wherein the 5' T of the $(TCG(N_q))_y$ (SEQ ID NO: 3) sequence is 0-3 bases from the 5' end of the polynucleotide. The ISS further comprises a palindromic sequence 10 bases in length or greater wherein the palindromic sequence comprises the first $(X_1X_2X_3X_4CGVX_3'X_2'X_1')$ (SEQ ID NO: 7) of the at least one $(X_1X_2X_3X_4CGX_4'X_3'X_2'X_1'(CG)_p)$ (SEQ ID NO: 8) sequence. In an ISS with w=−1, the 3' base of the $(TCG(N_q))_y$ (SEQ ID NO: 3) sequence is the 5' $X_1$ of the first $(X_1X_2X_3X_4CGX_4'X_3'X_2'X_1'(CG)_p)$ (SEQ ID NO: 8) sequence. In an ISS with w=−2, the penultimate (i.e., second to last) and the ultimate (i.e., last) 3' bases of the $(TCG(N_q))_y$ (SEQ ID NO: 3) sequence are the 5' $X_1$ and $X_2$, respectively, of the first $(X_1X_2X_3X_4CGX_4'X_3'X_2'X_1'(CG)_p)$ (SEQ ID NO: 8) sequence. In an ISS with w=−3, the antepenultimate (i.e., third to last), the penultimate (i.e., second to last) and the ultimate (i.e., last) 3' bases of the $(TCG(N_q))_y$ (SEQ ID NO: 3) sequence are the 5' $X_1$, $X_2$, and $X_3$, respectively, of the first $(X_1X_2X_3X_4CGX_4'X_3'X^{2'}X_1'(CG)_p)$ (SEQ ID NO: 8) sequence. In some embodiments, the $(TCG(N_q))_y$ (SEQ ID NO: 3) sequence is separated from the palindromic sequence by 0, 1 or 2 bases. In other embodiments, the palindromic sequence includes all or part of the $(TCG(N_q))_y$ (SEQ ID NO: 3) sequence. In some embodiments, when p=1, at least three of $X_1$, $X_2$, $X_3$, and $X_4$ are either A or T. In some embodiments, when p=0, at least two of $X_1$, $X_2$, $X_3$, and $X_4$ are either A or T.

In some embodiments, an ISS may comprise a sequence of the formula: 5'-$N_x(TCG(N_q))_yN_w(X_1CGCGX_1'(CG)_p)_z$ (SEQ ID NO: 9) wherein N are nucleosides with x=0-3, y=1-4, w=−1, 0, 1 or 2, p=0 or 1, q=0, 1 or 2, and z=1-20, wherein $X_1$ and $X_1'$ are self-complimentary and wherein the 5' T of the $(TCG(N_q))_y$ (SEQ ID NO: 3) sequence is 0-3 bases from the 5' end of the polynucleotide. The ISS further comprises a palindromic sequence 8 bases in length or greater wherein the palindromic sequence comprises the first $(X_1CGCGX_1')$ of the at least one $(X_1CGCGX_1'(CG)_p)$ sequence. In an ISS with w=−1, the 3' base of the $(TCG(N_q))_y$ (SEQ ID NO: 3) sequence is the 5' $X_1$ of the first $(X_1CGCGX_1'(CG)_p)$ sequence. In some embodiments, the $(TCG(N_q))_y$ (SEQ ID NO: 3) sequence is separated from the palindromic sequence by 0, 1 or 2 bases. In other embodiments, the palindromic sequence includes all or part of the $(TCG(N_q))_y$ (SEQ ID NO: 3) sequence.

In some embodiments, an ISS may comprise a sequence of the formula: 5'-$N_x(TCG(N_q))_yN_w(CGX_1X_1'CG(CG)_p)_z$ (SEQ ID NO: 10) wherein N are nucleosides with x=0-3, y=1-4, w=−2, 0, 1 or 2, p=0 or 1, q=0, 1 or 2, and z=1-20, wherein $X_1$ and $X_1'$ are self-complimentary and wherein the 5' T of the $(TCG(N_q))_y$ (SEQ ID NO: 3) sequence is 0-3 bases from the 5' end of the polynucleotide. The ISS further comprises a palindromic sequence 8 bases in length or greater wherein the palindromic sequence comprises the first $(CGX_1X_1'CG)$ of the at least one $(CGX_1X_1'CG(CG)_p)$ sequence. In an ISS with w=−2, the penultimate (i.e., second to last) and the ultimate (i.e., last) 3' bases of the $(TCG(N_q))_y$ (SEQ ID NO: 3) sequence are CG and are the 5' CG of the first $(CGX_1X_1'(CG(CG)_p)$ sequence. In some embodiments, the $(TCG(N_q))_y$ (SEQ ID NO: 3) sequence is separated from the palindromic sequence by 0, 1 or 2 bases. In other embodiments, the palindromic sequence includes all or part of the $(TCG(N_q))_y$ (SEQ ID NO: 3) sequence.

In some embodiments, an ISS may comprise a sequence of the formula: 5'-$N_x(TCG(N_q))_yN_w(X_1X_2CGX_3X_3'CGX_2'X_1'(CG)_p)_z$ (SEQ ID NO: 11) wherein N are nucleosides with x=0-3, y=1-4, w=−2, −1, 0, 1 or 2, p=0 or 1, q=0, 1 or 2, and z=1-20, wherein $X_1$ and $X_1'$, $X_2$ and $X_2'$, and $X_3$ and $X_3'$ are self-complimentary and wherein the 5' T of the $(TCG(N_q))_y$ (SEQ ID NO: 3) sequence is 0-3 bases from the 5' end of the polynucleotide. The ISS further comprises a palindromic sequence 10 bases in length or greater wherein the palindromic sequence comprises the first $(X_1X_2CGX_3X_3'CGX_2'X_1')$ (SEQ ID NO: 12) of the at least one $(X_1X_2CGX_3X_3'CGX_2'X_1'(CG)_p)$ (SEQ ID NO: 13) sequence. In an ISS with w=−1, the 3' base of the $(TCG(N_q))_y$ (SEQ ID NO: 3) sequence is the 5' $X_1$ of the first $(X_1X_2CGX_3X_3'CGX_2'X_1'(CG)_p)$ (SEQ ID NO: 13) sequence. In an ISS with w=−2, the penultimate (i.e., second to last) and the ultimate (i.e., last) 3' bases of the $(TCG(N_q))_y$ (SEQ ID NO: 3) sequence are the 5' $X_1$ and $X_2$, respectively, of the first $(X_1X_2CGX_3X_3'CGX_2'X_1'(CG)_p)$ (SEQ ID NO: 13) sequence. In some embodiments, the $(TCG(N_q))_y$ (SEQ ID NO: 3) sequence is separated from the palindromic sequence by 0, 1 or 2 bases. In other embodiments, the palindromic sequence includes all or part of the $(TCG(N_q))_y$ (SEQ ID NO: 3) sequence. In some embodiments, when p=1, $X_1$, $X_2$, and $X_3$ are each either A or T. In some embodiments, when p=0, at least two of $X_1$, $X_2$, and $X_3$ are either A or T.

In some embodiments, an ISS may comprise a sequence of the formula: 5'-$N_x(TCG(N_q))_yN_w(X_1X_2CGX_2'X_1'(CG)_p)_z$ (SEQ ID NO: 14) wherein N are nucleosides with x=0-3, y=1-4, w=−2, −1, 0, 1 or 2, p=0 or 1, q=0, 1 or 2, and z=1-20, wherein $X_1$ and $X_1'$, $X_2$ and $X_2'$ are self-complimentary, and wherein the 5' T of the $(TCG(N_q))_y$ (SEQ ID NO: 3) sequence is 0-3 bases from the 5' end of the polynucleotide. The ISS further comprises a palindromic sequence 8 bases in length or greater wherein the palindromic sequence comprises the first $(X_1X_2CGX_2'X_1')$ of the at least one $(X_1X_2CGX_2'X_1'(CG)_p)_z$ (SEQ ID NO: 28) sequence. In an ISS with w=−1, the 3' base of the $(TCG(N_q))_y$ (SEQ ID NO: 3) sequence is the 5' $X_1$ of the first $(X_1X_2CGX_2'X_1'(CG)_p)$ sequence. In an ISS with w=−2, the penultimate (i.e., second to last) and the ultimate (i.e., last) 3' bases of the $(TCG(N_q))_y$ (SEQ ID NO: 3) sequence are the 5' $X_1$ and $X_2$, respectively, of the first $(X_1X_2CGX_2'X_1'(CG)_p)$ sequence. In some embodiments, the $(TCG(N_q))_y$ (SEQ ID NO: 3) sequence is separated from the palindromic sequence by 0, 1 or 2 bases. In other embodiments, the palindromic sequence includes all or part of the $(TCG(N_q))_y$ (SEQ ID NO: 3) sequence. In some embodiments, $X_1$ and $X_2$ are each either A or T.

In some embodiments, an ISS may comprise a sequence of the formula: 5'-$N_x(TCG(N_q))_yN_w$ $(X_1X_2X_3X_4X_5CGX_5'X_4'X_3'X_2'X_1'(CG)_p)_z$ (SEQ ID NO: 15) wherein N are nucleosides with x=0-3, y=1-4, w=−3, −2, −1, 0, 1 or 2, p=0 or 1, q=0, 1 or 2, and z=1-20, wherein $X_1$ and $X_1'$, $X_2$ and $X_2'$, $X_3$ and $X_3'$, $X_4$ and $X_4'$, and $X_5$ and $X_5'$ are self-complimentary, and wherein the 5' T of the $(TCG(N_q))_y$ (SEQ ID NO: 3) sequence is 0-3 bases from the 5' end of the polynucleotide. The ISS further comprises a palindromic sequence 12 bases in length or greater wherein the palindromic sequence comprises the first $(X_1X_2X_3X_4X_5CGX_5'X_4'X_3'X_2'X_1')$ (SEQ ID NO: 16) of the at least one (($X_1X_2X_3X_4X_5CGX_5'X_4'X_3'X_2'X_1'(CG)_p$) (SEQ ID NO: 17) sequence. In an ISS with w=−1, the 3′ base of the ($TCG(N_q))_y$ (SEQ ID NO: 3) sequence is the 5′ $X_1$ of the first ($X_1X_2X_3X_4X_5CGX_5'X_4'X_3'X_2'X_1'(CG)_p$) (SEQ ID NO: 17) sequence. In an ISS with w=−2, the penultimate (i.e., second to last) and the ultimate (i.e., last) 3′ bases of the $(TCG(N_q))_y$ (SEQ ID NO: 3) sequence are the 5′ $X_1$ and $X_2$, respectively, of the first ($X_1X_2X_3X_4X_5CGX_5'X_4'X_3'X_2'X_1'(CG)_p$) (SEQ ID NO: 17) sequence. In an ISS with w=−3, the antepenultimate (i.e., third to last), the penultimate (i.e., second to last) and the ultimate (i.e., last) 3′ bases of the $(TCG(N_q))_y$ (SEQ ID NO: 3) sequence are the 5′ $X_1$, $X_2$, and $X_3$, respectively, of the first ($X_1X_2X_3X_4X_5CGX_5'X_4'X_3'X_2'X_1'(CG)_p$) (SEQ ID NO: 17) sequence. In some embodiments, the $(TCG(N_q))_y$ (SEQ ID NO: 3) sequence is separated from the palindromic sequence by 0, 1 or 2 bases. In other embodiments, the palindromic sequence includes all or part of the $(TCG(N_q))_y$ (SEQ ID NO: 3) sequence. In some embodiments, at least three of $X_1$, $X_2$, $X_3$, $X_4$, and $X_5$ are either A or T.

In some embodiments, an ISS may comprise a sequence of the formula: 5′-$N_x(TCG(N_q))_yN_w(X_1X_2CGCGX_2'X_1'(CG)_p)_z$ (SEQ ID NO: 18) wherein N are nucleosides with x=0-3, y=1-4, w=−2, −1, 0, 1 or 2, p=0 or 1, q=0, 1 or 2, and z=1-20, wherein $X_1$ and $X_1'$, and $X_2$ and $X_2'$ are self-complimentary, and wherein the 5′ T of the $(TCG(N_q))_y$ (SEQ ID NO: 3) sequence is 0-3 bases from the 5′ end of the polynucleotide. The ISS further comprises a palindromic sequence 8 bases in length or greater wherein the palindromic sequence comprises the first ($X_1X_2CGCGX_2'X_1'$) of the at least one ($X_1X_2CGCGX_2'X_1'(CG)_p$) (SEQ ID NO: 19) sequence. In an ISS with w=−1, the 3′ base of the $(TCG(N_q))_y$ (SEQ ID NO: 3) sequence is the 5′ $X_1$ of the first ($X_1X_2CGCGX_2'X_1'(CG)_p$) (SEQ ID NO: 19) sequence. In an ISS with w=−2, the penultimate (i.e., second to last) and the ultimate (i.e., last) 3′ bases of the $(TCG(N_q))_y$ (SEQ ID NO: 3) sequence are the 5′ $X_1$ and $X_2$, respectively, of the first ($X_1X_2CGCGX_2'X_1'(CG)_p$) (SEQ ID NO: 19) sequence. In some embodiments, the $(TCG(N_q))_y$ (SEQ ID NO: 3) sequence is separated from the palindromic sequence by 0, 1 or 2 bases. In other embodiments, the palindromic sequence includes all or part of the $(TCG(N_q))_y$ (SEQ ID NO: 3) sequence. In some embodiments, $X_1$ and $X_2$ are each either A or T.

In some embodiments, an ISS may comprise a sequence of the formula: 5′-$N_x(TCG(N_q))_yN_w(X_1X_2X_3CGCGX_3'X_2'X_1'(CG)_p)_z$ (SEQ ID NO: 20) wherein N are nucleosides with x=0-3, y=1-4, w=−3, −2, −1, 0, 1 or 2, p=0 or 1, q=0, 1 or 2, and z=1-20, wherein $X_1$ and $X_1'$, $X_2$ and $X_2'$ and $X_3$ and $X_3'$ are self-complimentary, and wherein the 5′ T of the $(TCG(N_q))_y$ (SEQ ID NO: 3) sequence is 0-3 bases from the 5′ end of the polynucleotide. The ISS further comprises a palindromic sequence 10 bases in length or greater wherein the palindromic sequence comprises the first ($X_1X_2X_3CGCGX_3'X_2'X_1'$) (SEQ ID NO: 21) of the at least one ($X_1X_2X_3CGCGX_3'X_2'X_1'(CG)_p$) (SEQ ID NO: 22) sequence. In an ISS with w=−1, the 3′ base of the $(TCG(N_q))_y$ (SEQ ID NO: 3) sequence is the 5′ $X_1$ of the first ($X_1X_2X_3CGCGX_3'X_2'X_1'(CG)_p$) (SEQ ID NO: 22) sequence. In an ISS with w=−2, the penultimate (i.e., second to last) and the ultimate (i.e., last) 3′ bases of the $(TCG(N_q))_y$ (SEQ ID NO: 3) sequence are the 5′ $X_1$ and $X_2$, respectively, of the first ($X_1X_2X_3CGCGX_3'X_2'X_1'(CG)_p$) (SEQ ID NO: 22) sequence. In an ISS with w=−3, the antepenultimate (i.e., third to last), the penultimate (i.e., second to last) and the ultimate (i.e., last) 3′ bases of the $(TCG(N_q))_y$ (SEQ ID NO: 3) sequence are the 5′ $X_1$, $X_2$, and $X_3$, respectively, of the first ($X_1X_2X_3CGCGX_3'X_2'X_1'(CG)_p$) (SEQ ID NO: 22) sequence. In some embodiments, the $(TCG(N_q))_y$ (SEQ ID NO: 3) sequence is separated from the palindromic sequence by 0, 1 or 2 bases. In other embodiments, the palindromic sequence includes all or part of the $(TCG(N_q))_y$ (SEQ ID NO: 3) sequence. In some embodiments, when p=1, $X_1$, $X_2$, and $X_3$ are each either A or T. In some embodiments, when p=0, at least two of $X_1$, $X_2$, and $X_3$ are either A or T.

In some embodiments, an ISS may comprise a sequence of the formula: 5′-$N_x(TCG(N_q))_yN_w(CGX_1X_2X_2'X_1'CG(CG)_p)_z$ (SEQ ID NO: 23) wherein N are nucleosides with x=0-3, y=1-4, w=−2, 0, 1 or 2, p=0 or 1, q=0, 1 or 2, and z=1-20, wherein $X_1$ and $X_1'$, and $X_2$ and $X_2'$ are self-complimentary, and wherein the 5′ T of the $(TCG(N_q))_y$ (SEQ ID NO: 3) sequence is 0-3 bases from the 5′ end of the polynucleotide. The ISS further comprises a palindromic sequence 8 bases in length or greater wherein the palindromic sequence comprises the first ($CGX_1X_2X_2'X_1'CG$) of the at least one ($CGX_1X_2X_2'X_1'CG(CG)_p$) (SEQ ID NO: 24) sequence. In an ISS with w=−2, the penultimate (i.e., second to last) and the ultimate (i.e., last) 3′ bases of the $(TCG(N_q))_y$ (SEQ ID NO: 3) sequence are CG and are the 5′ CG of the first ($CGX_1X_2X_2'X_1'CG(CG)_p$) (SEQ ID NO: 24) sequence. In some embodiments, the $(TCG(N_q))_y$ (SEQ ID NO: 3) sequence is separated from the palindromic sequence by 0, 1 or 2 bases. In other embodiments, the palindromic sequence includes all or part of the $(TCG(N_q))_y$ (SEQ ID NO: 3) sequence. In some embodiments, $X_1$ and $X_2$ are each either A or T.

For ISSs comprising any of the motifs described herein where y=2 or more, the $(N_q)$ in each of the y repetitions of the $(TCG(N_q))$ is independently selected. For example, in an ISS with y=2, the first $TCG(N_q)$ may have N=A and q=1 and the second $TCG(N_q)$ may have q=0 in which case this portion of the ISS would be . . . TCGATCG . . . . In some embodiments of ISSs comprising any of the motifs described herein in some embodiments, x is preferably 0 or 1. In some embodiments of ISSs comprising any of the motifs described herein, y is preferably 1 or 2. In some embodiments of ISSs comprising any of the motifs described herein, w is preferably 0. In some embodiments of ISSs comprising any of the motifs described herein, z is preferably 1, 2, 3, 4, 5, 6, 7 or 8.

As noted above, the ISSs contain at least one the palindromic sequence at least 8 bases in length. In some embodiments, an ISS contains at least one palindromic sequence of at least the following lengths (in bases): 10, 12, 14, 16, 18, 20, 22, 24, 26, 28, 30. In some embodiments, the palindromic sequence is repeated at least once in an ISS. In some embodiments, the palindromic sequence also includes bases 5′ of the $(TCG(N_q))_y$ sequence, if any.

Non-limiting examples of specific ISSs that can be used in accordance with the teachings above can be found in U.S. Publication No. 2006/0058254 and also in U.S. Publication No. 2004/0132677.

Modifications to ISS

An ISS may contain modifications. Modifications of ISS include any known in the art, but are not limited to, modifications of the 3′OH or 5′OH group, modifications of the nucleotide base, modifications of the sugar component, and modifications of the phosphate group. Modified bases may be included in the palindromic sequence of an ISS as long as the modified base(s) maintains the same specificity for its natural complement through Watson-Crick base pairing (e.g., the palindromic portion of the ISS is still self-complementary).

An ISS may contain naturally-occurring or modified, non-naturally occurring bases, and may contain modified sugar, phosphate, and/or termini. For example, in addition to phosphodiester linkages, phosphate modifications include, but are not limited to, methyl phosphonate, phosphorothioate, phosphoramidate (bridging or non-bridging), phosphotriester and phosphorodithioate and may be used in any combination. Other non-phosphate linkages may also be used. In some embodiments, polynucleotides of the present invention comprise only phosphorothioate backbones. In some embodiments, polynucleotides of the present invention comprise only phosphodiester backbones. In some embodiments, an ISS may comprise a combination of phosphate linkages in the phosphate backbone such as a combination of phosphodiester and phosphorothioate linkages.

Sugar modifications known in the field, such as 2'-alkoxy-RNA analogs, 2'-amino-RNA analogs, 2'-fluoro-DNA, and 2'-alkoxy- or amino-RNA/DNA chimeras and others described herein, may also be made and combined with any phosphate modification. Examples of base modifications include, but are not limited to, addition of an electron-withdrawing moiety to C-5 and/or C-6 of a cytosine of the ISS (e.g., 5-bromocytosine, 5-chlorocytosine, 5-fluorocytosine, 5-iodocytosine) and C-5 and/or C-6 of a uracil of the ISS (e.g., 5-bromouracil, 5-chlorouracil, 5-fluorouracil, 5-iodouracil). See, for example, WO 99/62923. The use of a base modification in a palindromic sequence of an ISS should not interfere with the self-complimentary ability of the bases involved for Watson-Crick base pairing. However, outside of a palindromic sequence, modified bases may be used without this restriction.

In addition, backbone phosphate group modifications (e.g., methylphosphonate, phosphorothioate, phosphoroamidate and phosphorodithioate internucleotide linkages) can confer immunomodulatory activity on the ISS and enhance their stability in vivo, making them particularly useful in therapeutic applications. A particularly useful phosphate group modification is the conversion to the phosphorothioate or phosphorodithioate forms of the ISS oligonucleotides. In addition to their potentially immunomodulatory properties, phosphorothioates and phosphorodithioates are more resistant to degradation in vivo than their unmodified oligonucleotide counterparts, making the ISS of the invention more available to the individual.

Synthesis of and Screening for ISS

The ISS can be synthesized using techniques and nucleic acid synthesis equipment which are well known in the art including, but not limited to, enzymatic methods, chemical methods, and the degradation of larger oligonucleotide sequences. See, for example, Ausubel et al. (1987) and Sambrook et al. (1989). When assembled enzymatically, the individual units can be ligated, for example, with a ligase such as T4 DNA or RNA ligase. See, for example, U.S. Pat. No. 5,124,246. Oligonucleotide degradation can be accomplished through the exposure of an oligonucleotide to a nuclease, as exemplified in U.S. Pat. No. 4,650,675.

The ISS can also be isolated using conventional polynucleotide isolation procedures. Such procedures include, but are not limited to, hybridization of probes to genomic or cDNA libraries to detect shared nucleotide sequences, antibody screening of expression libraries to detect shared structural features and synthesis of particular native sequences by the polymerase chain reaction.

Circular ISS can be isolated, synthesized through recombinant methods, or chemically synthesized. Where the circular ISS is obtained through isolation or through recombinant methods, the ISS will preferably be a plasmid. The chemical synthesis of smaller circular oligonucleotides can be performed using any method described in the literature. See, for instance, Gao et al. (1995) *Nucleic Acids Res.* 23:2025-2029; and Wang et al. (1994) *Nucleic Acids Res.* 22:2326-2333.

Duplex (i.e., double stranded) and hairpin forms of most ISSs are in dynamic equilibrium, with the hairpin form generally favored at low polynucleotide concentration and higher temperatures. Covalent interstrand or intrastrand cross-links increases duplex or hairpin stability, respectively, towards thermal-, ionic-, pH-, and concentration-induced conformational changes. Chemical cross-links can be used to lock the polynucleotide into either the duplex or the hairpin form for physicochemical and biological characterization. Cross-linked ISSs that are conformationally homogeneous and are "locked" in their most active form (either duplex or hairpin form) could potentially be more active than their uncross-linked counterparts. Accordingly, some ISSs of the invention contain covalent interstrand and/or intrastrand cross-links.

A variety of ways to chemically cross-link duplex DNA are known in the art. Any cross-linking method may be used as long as the cross-linked polynucleotide product possesses the desired immunomodulatory activity.

One method, for example, results in a disulfide bridge between two opposing thymidines at the terminus of the duplex or hairpin. For this cross-linking method, the oligonucleotide(s) of interest is synthesized with a 5'-DMT-N3-(tBu-SS-ethyl)thymidine-3'-phosphoramidite ("T*"). To form the disulfide bridge, the mixed disulfide bonds are reduced, oligonucleotide purified, the strands hybridized and the compound air-oxidized to form the intrastrand cross-link in the case of a hairpin form or the interstrand cross-link in the case of a duplex form. Alternatively, the oligonucleotides may be hybridized first and then reduced, purified and air-oxidized. Such methods and others are described, for example, in Glick et al. (1991) *J. Org. Chem.* 56:6746-6747, Glick et al. (1992) *J. Am. Chem. Soc.* 114:5447-5448, Goodwin et al. (1994) *Tetrahedron Letters* 35:1647-1650, Wang et al. (1995) *J. Am. Chem. Soc.* 117:2981-2991, Osborne et al. (1996) *Bioorganic & Medicinal Chemistry Letters* 6:2339-2342 and Osborne et al. (1996) *J. Am. Chem. Soc.* 118:11993-12003.

Another cross-linking method forms a disulfide bridge between offset residues in the duplex or hairpin structure. For this cross-linking method, the oligonucleotide(s) of interest is synthesized with convertible nucleosides (commercially available, for example, from Glen Research). This method utilizes, for example, an A-A disulfide or a C-A disulfide bridge and linkages through other bases are also possible. To form the disulfide-modified polynucleotide, the polynucleotide containing the convertible nucleoside is reacted with cystamine (or other disulfide-containing amine). To form the disulfide bridge, the mixed disulfide bonds are reduced, oligonucleotide purified, the strands hybridized and the compound air-oxidized to form the intrastrand cross-link in the case of a hairpin form or the interstrand cross-link in the case of a duplex form. Alternatively, the oligonucleotides may be hybridized first and then reduced, purified and air-oxidized. Such methods and others are described, for example, in Glick et al. (1991) *J. Org. Chem.* 56:6746-6747, Glick et al. (1992) *J. Am. Chem. Soc.* 114:5447-5448, Goodwin et al. (1994) *Tetrahedron Letters* 35:1647-1650, Wang et al. (1995) *J. Am. Chem. Soc.* 117:2981-2991, Osborne et al. (1996) *Bioorganic & Medicinal Chemistry Letters* 6:2339-2342 and Osborne et al. (1996) *J. Am. Chem. Soc.* 118:11993-12003.

Another cross-linking method forms a disulfide bridge between offset residues in the duplex or hairpin structure. For this cross-linking method, the oligonucleotide(s) of interest is synthesized with convertible nucleosides (commercially available, for example, from Glen Research). This method utilizes, for example, an A-A disulfide or a C-A disulfide bridge and linkages through other bases are also possible. To form the disulfide-modified polynucleotide, the polynucleotide containing the convertible nucleoside is reacted with cystamine (or other disulfide-containing amine). To form the disulfide bridge, the mixed disulfide bonds are reduced, oligonucleotide purified, the strands hybridized and the compound air-oxidized to form the intrastrand cross-link in the case of a hairpin form or the interstrand cross-link in the case of a duplex form. Alternatively, the oligonucleotides may be hybridized first and then reduced, purified and air-oxidized. Such methods are described, for example, in Ferentz et al. (1991) *J. Am. Chem. Soc.* 113:4000-4002 and Ferentz et al. (1993) *J. Am. Chem. Soc.* 115:9006-9014.

The techniques for making polynucleotides and modified polynucleotides are known in the art. Naturally occurring DNA or RNA, containing phosphodiester linkages, is generally synthesized by sequentially coupling the appropriate nucleoside phosphoramidite to the 5'-hydroxy group of the growing oligonucleotide attached to a solid support at the 3'-end, followed by oxidation of the intermediate phosphite triester to a phosphate triester. Once the desired polynucleotide sequence has been synthesized, the polynucleotide is removed from the support, the phosphate triester groups are deprotected to phosphate diesters and the nucleoside bases are deprotected using aqueous ammonia or other bases. See, for example, Beaucage (1993) "Oligodeoxyribonucleotide Synthesis" in Protocols for Oligonucleotides and Analogs, Synthesis and Properties (Agrawal, ed.) Humana Press, Totowa, N.J.; Warner et al. (1984) *DNA* 3:401 and U.S. Pat. No. 4,458,066.

The ISS can also contain phosphate-modified polynucleotides, some of which are known to stabilize the polynucleotide. Accordingly, some embodiments includes stabilized ISSs. Synthesis of polynucleotides containing modified phosphate linkages or non-phosphate linkages is also known in the art. For a review, see Matteucci (1997) "Oligonucleotide Analogs: an Overview" in Oligonucleotides as Therapeutic Agents, (D. J. Chadwick and G. Cardew, ed.) John Wiley and Sons, New York, N.Y. The phosphorous derivative (or modified phosphate group) which can be attached to the sugar or sugar analog moiety in the polynucleotides of the present invention can be a monophosphate, diphosphate, triphosphate, alkylphosphonate, phosphorothioate, phosphorodithioate, phosphoramidate or the like. The preparation of the above-noted phosphate analogs, and their incorporation into nucleotides, modified nucleotides and oligonucleotides, per se, is also known and need not be described here in detail. Peyrottes et al. (1996) *Nucleic Acids Res.* 24:1841-1848; Chaturvedi et al. (1996) *Nucleic Acids Res.* 24:2318-2323; and Schultz et al. (1996) *Nucleic Acids Res.* 24:2966-2973. For example, synthesis of phosphorothioate oligonucleotides is similar to that described above for naturally occurring oligonucleotides except that the oxidation step is replaced by a sulfurization step (Zon (1993) "Oligonucleoside Phosphorothioates" in Protocols for Oligonucleotides and Analogs, Synthesis and Properties (Agrawal, ed.) Humana Press, pp. 165-190). Similarly the synthesis of other phosphate analogs, such as phosphotriester (Miller et al. (1971) *JACS* 93:6657-6665), non-bridging phosphoramidates (Jager et al. (1988) *Biochem.* 27:7247-7246), N3' to P5' phosphoramidiates (Nelson et al. (1997) *JOC* 62:7278-7287) and phosphorodithioates (U.S. Pat. No. 5,453,496) has also been described. Other non-phosphorous based modified oligonucleotides can also be used (Stirchak et al. (1989) *Nucleic Acids Res.* 17:6129-6141). Polynucleotides with phosphorothioate backbones can be more immunogenic than those with phosphodiester backbones and appear to be more resistant to degradation after injection into the host. Braun et al. (1988) *J. Immunol.* 141:2084-2089; and Latimer et al. (1995) *Mol. Immunol.* 32:1057-1064.

ISSs used in the invention can comprise one or more ribonucleotides (containing ribose as the only or principal sugar component), deoxyribonucleotides (containing deoxyribose as the principal sugar component), or, as is known in the art, modified sugars or sugar analogs can be incorporated in the ISS. Thus, in addition to ribose and deoxyribose, the sugar moiety can be pentose, deoxypentose, hexose, deoxyhexose, glucose, arabinose, xylose, lyxose, and a sugar "analog" cyclopentyl group. The sugar can be in pyranosyl or in a furanosyl form. In the ISS, the sugar moiety is preferably the furanoside of ribose, deoxyribose, arabinose or 2'-0-alkylribose, and the sugar can be attached to the respective heterocyclic bases either in α or β anomeric configuration. Sugar modifications include, but are not limited to, 2'-alkoxy-RNA analogs, 2'-amino-RNA analogs, 2'-fluoro-DNA, and 2'-alkoxy- or amino-RNA/DNA chimeras. For example, a sugar modification in the ISS includes, but is not limited to, 2'-O-methyl-uridine and 2'-O-methyl-cytidine. The preparation of these sugars or sugar analogs and the respective "nucleosides" wherein such sugars or analogs are attached to a heterocyclic base (nucleic acid base) per se is known, and need not be described here, except to the extent such preparation can pertain to any specific example. Sugar modifications may also be made and combined with any phosphate modification in the preparation of an ISS.

The heterocyclic bases, or nucleic acid bases, which are incorporated in the ISS can be the naturally-occurring principal purine and pyrimidine bases, (namely uracil, thymine, cytosine, adenine and guanine, as mentioned above), as well as naturally-occurring and synthetic modifications of said principal bases. Thus, an ISS may include 2'-deoxyuridine and/or 2-amino-2'-deoxyadenosine.

Those skilled in the art will recognize that a large number of "synthetic" non-natural nucleosides comprising various heterocyclic bases and various sugar moieties (and sugar analogs) are available in the art, and that as long as other criteria of the present invention are satisfied, the ISS can include one or several heterocyclic bases other than the principal five base components of naturally-occurring nucleic acids. Preferably, however, the heterocyclic base in the ISS includes, but is not limited to, uracil-5-yl, cytosin-5-yl, adenin-7-yl, adenin-8-yl, guanin-7-yl, guanin-8-yl, 4-aminopyrrolo[2,3-d]pyrimidin-5-yl, 2-amino-4-oxopyrolo[2,3-d]pyrimidin-5-yl, 2-amino-4-oxopyrrolo[2,3-d]pyrimidin-3-yl groups, where the purines are attached to the sugar moiety of the ISS via the 9-position, the pyrimidines via the 1-position, the pyrrolopyrimidines via the 7-position and the pyrazolopyrimidines via the 1-position.

The ISS may comprise at least one modified base. As used herein, the term "modified base" is synonymous with "base analog," for example, "modified cytosine" is synonymous with "cytosine analog." Similarly, "modified" nucleosides or nucleotides are herein defined as being synonymous with nucleoside or nucleotide "analogs." Examples of base modifications include, but are not limited to, addition of an electron-withdrawing moiety to C-5 and/or C-6 of a cytosine of the ISS. Preferably, the electron-withdrawing moiety is a halogen. Such modified cytosines can include, but are not limited to, azacytosine, 5-bromocytosine, bromouracil, 5-chlorocytosine, chlorinated cytosine, cyclocytosine, cytosine arabinoside, 5-fluorocytosine, fluoropyrimidine, fluorouracil, 5,6-dihydrocytosine, 5-iodocytosine, hydroxyurea, iodouracil, 5-nitrocytosine, uracil, and any other pyrimidine analog or modified pyrimidine. Other examples of base modifications include, but are not limited to, addition of an electron-withdrawing moiety to C-5 and/or C-6 of a uracil of the ISS. Preferably, the electron-withdrawing moiety is a halogen. Such modified uracils can include, but are not limited to, 5-bromouracil, 5-chlorouracil, 5-fluorouracil, and 5-iodouracil.

Other examples of base modifications include the addition of one or more thiol groups to the base including, but not limited to, 2-amino-adenine, 6-thio-guanine, 2-thio-thymine, 4-thio-thymine, 5-propynyl-uracil, and 4-thio-uracil. Other examples of base modifications include, but are not limited to, N4-ethylcytosine, 7-deazaguanine, 7-deaza-8-azaguanine and 5-hydroxycytosine. See, for example, Kandimalla et al. (2001) *Bioorg. Med. Chem.* 9:807-813.

The preparation of base-modified nucleosides, and the synthesis of modified oligonucleotides using said base-modified nucleosides as precursors, has been described, for example, in U.S. Pat. Nos. 4,910,300, 4,948,882, and 5,093,232. These base-modified nucleosides have been designed so that they can be incorporated by chemical synthesis into either terminal or internal positions of an oligonucleotide. Such base-modified nucleosides, present at either terminal or internal positions of an oligonucleotide, can serve as sites for attachment of a peptide or other antigen. Nucleosides modified in their sugar moiety have also been described (including, but not limited to, e.g., U.S. Pat. Nos. 4,849,513; 5,015,733; 5,118,800; and 5,118,802) and can be used similarly.

In some embodiments, an ISS is less than about any of the following lengths (in bases or base pairs): 10,000; 5,000; 2500; 2000; 1500; 1250; 1000; 750; 500; 300; 250; 200; 175; 150; 125; 100; 75; 60; 50; 40; 30; 25; 20; 15; 14; 13; 12; 11; 10. In some embodiments, an ISS is greater than about any of the following lengths (in bases or base pairs): 10; 11; 12; 13; 14; 15; 20; 25; 30; 40; 50; 60; 75; 100; 125; 150; 175; 200; 250; 300; 350; 400; 500; 750; 1000; 2000; 5000; 7500; 10000; 20000; 50000. Alternately, the ISS can be any of a range of sizes having an upper limit of 10,000; 5,000; 2500; 2000; 1500; 1250; 1000; 750; 500; 300; 250; 200; 175; 150; 125; 100; 75; 60; 50; 40; 30; 25; 20; 15; 14; 13; 12; 11; 10 and an independently selected lower limit of 10; 11; 12; 13; 14; 15; 20; 25; 30; 40; 50; 60; 75; 100; 125; 150; 175; 200; 250; 300; 350; 400; 500; 750; 1000; 2000; 5000; 7500, wherein the lower limit is less than the upper limit. In some embodiments, an ISS is preferably about 200 or less bases in length.

Alternatively, ISS may be isolated from microbial species (especially mycobacteria) using techniques well-known in the art, such as nucleic acid hybridization. Preferably, such isolated ISS will be purified to a substantially pure state, i.e., to be free of endogenous contaminants, such as lipopolysaccharides. ISS isolated as part of a larger polynucleotide can be reduced to the desired length by techniques well known in the art, such as by endonuclease digestion. Those of ordinary skill in the art will be familiar with, or can readily ascertain, techniques suitable for isolation, purification and digestion of polynucleotides to obtain ISS of potential use in the invention.

Confirmation that a particular oligonucleotide has the properties of an ISS useful in the invention can be obtained by evaluating whether the ISS affects cytokine secretion as described in infra. Details of in vitro techniques useful in making such an evaluation are given in the Examples; those of ordinary skill in the art will also know of, or can readily ascertain, other methods for measuring cytokine secretion along the parameters taught herein.

Antigen that May be Administered with ISS

Any antigen may be co-administered with an ISS and/or used in compositions comprising an ISS and antigen (and preparation of these compositions).

In some embodiments, the antigen is an allergen. Examples of recombinant allergens are provided in Table 1. Preparation of many allergens is well-known in the art, including, but not limited to, preparation of ragweed pollen allergen Antigen E (Amb a I) (Rafnar et al. (1991) *J. Biol. Chem.* 266:1229-1236), grass allergen Lol p 1 (Tamborini et al. (1997) *Eur. J. Biochem.* 249:886-894), major dust mite allergens Der pI and Der PII (Chua et al. (1988) *J. Exp. Med.* 167:175-182; Chua et al. (1990) *Int. Arch. Allergy Appl. Immunol.* 91:124-129), domestic cat allergen Fel d I (Rogers et al. (1993) *Mol. Immunol.* 30:559-568), white birch pollen Bet v1 (Breiteneder et al. (1989) *EMBO J.* 8:1935-1938), Japanese cedar allergens Cry j 1 and Cry j 2 (Kingetsu et al. (2000) *Immunology* 99:625-629), and protein antigens from other tree pollen (Elsayed et al. (1991) *Scand. J. Clin. Lab. Invest. Suppl.* 204:17-31). As indicated, allergens from trees are known, including allergens from birch, juniper and Japanese cedar. Preparation of protein antigens from grass pollen for in vivo administration has been reported.

In some embodiments, the allergen is a food allergen, including, but not limited to, peanut allergen, for example Ara h I (Stanley et al. (1996) *Adv. Exp. Med. Biol.* 409:213-216); walnut allergen, for example, Jug r I (Tueber et al. (1998) *J. Allergy Clin. Immunol.* 101:807-814); brazil nut allergen, for example, albumin (Pastorello et al. (1998) *J. Allergy Clin. Immunol.* 102:1021-1027; shrISS allergen, for example, Pen a I (Reese et al. (1997) *Int. Arch. Allergy Immunol.* 113:240-242); egg allergen, for example, ovomucoid (Crooke et al. (1997) *J. Immunol.* 159:2026-2032); milk allergen, for example, bovine β-lactoglobin (Selot al. (1999) *Clin. Exp. Allergy* 29:1055-1063); fish allergen, for example, parvalbumins (Van Do et al. (1999) *Scand. J. Immunol.* 50:619-625; Galland et al. (1998) *J. Chromatogr. B. Biomed. Sci. Appl.* 706:63-71). In some embodiments, the allergen is a latex allergen, including but not limited to, Hev b 7 (Sowka et al. (1998) *Eur. J. Biochem.* 255:213-219). Table 1 shows an exemplary list of allergens that may be used.

TABLE 1

| RECOMBINANT ALLERGENS | | |
|---|---|---|
| Group | Allergen | Reference |
| ANIMALS: CRUSTACEA | | |
| ShrISS/lobster | tropomyosin | Leung et al. (1996) J. Allergy Clin. Immunol. 98: 954-961 |
| | Pan s I | Leung et al. (1998) Mol. Mar. Biol. Biotechnol. 7: 12-20 |
| INSECTS | | |
| Ant | Sol i 2 (venom) | Schmidt et al. J Allergy Clin Immunol., 1996, 98: 82-8 |
| Bee | Phospholipase A2 (PLA) | Muller et al. J Allergy Clin Immunol, 1995, 96: 395-402 |

TABLE 1-continued

RECOMBINANT ALLERGENS

| Group | Allergen | Reference |
|---|---|---|
| Cockroach | Hyaluronidase (Hya)<br>Bla g Bd9OK<br>Bla g 4 (a calycin)<br>Glutathione S-transferase<br>Per a 3 | Forster et al. J Allergy Clin Immunol, 1995, 95: 1229-35<br>Muller et al. Clin Exp Allergy, 1997, 27: 915-20<br>Soldatova et al. J Allergy Clin Immunol, 1998, 101: 691-8<br>Helm et al. J Allergy Clin Immunol, 1996, 98: 172-180<br>Vailes et al. J Allergy Clin Immunol, 1998, 101: 274-280<br>Arruda et al. J Biol Chem, 1997, 272: 20907-12<br>Wu et al. Mol Immunol, 1997, 34: 1-8 |
| Dust mite | Der p 2 (major allergen) | Lynch et al. J Allergy Clin Immunol, 1998, 101: 562-4<br>Hakkaart et al. Clin Exp Allergy, 1998, 28: 169-74<br>Hakkaart et al. Clin Exp Allergy, 1998, 28: 45-52<br>Hakkaart et al. Int Arch Allergy Immunol, 1998, 115 (2): 150-6<br>Mueller et al. J Biol Chem, 1997, 272: 26893-8 |
|  | Der p2 variant<br>Der f2 | Smith et al. J Allergy Clin Immunol, 1998, 101: 423-5<br>Yasue et al. Clin Exp Immunol, 1998, 113: 1-9<br>Yasue et al. Cell Immunol, 1997, 181: 30-7 |
|  | Der p10<br>Tyr p 2 | Asturias et al. Biochim Biophys Acta, 1998, 1397: 27-30<br>Eriksson et al. Eur J Biochem, 1998 |
| Hornet | Antigen 5 aka Dol m V (venom) | Tomalski et al. Arch Insect Biochem Physiol, 1993, 22: 303-13 |
| Mosquito | Aed a I (salivary apyrase) | Xu et al. Int Arch Allergy Immunol, 1998, 115: 245-51 |
| Yellow jacket | antigen 5, hyaluronidase and phospholipase (venom) | King et al. J Allergy Clin Immunol, 1996, 98: 588-600 |
| MAMMALS |  |  |
| Cat | Fel d I | Slunt et al. J Allergy Clin Immunol, 1995, 95: 1221-8<br>Hoffmann et al. (1997) J Allergy Clin Immunol 99: 227-32<br>Hedlin Curr Opin Pediatr, 1995, 7: 676-82 |
| Cow | Bos d 2 (dander; a lipocalin)<br>β-lactoglobulin (BLG, major cow milk allergen) | Zeiler et al. J Allergy Clin Immunol, 1997, 100: 721-7<br>Rautiainen et al. Biochem Bioph. Res Comm., 1998, 247: 746-50<br>Chatel et al. Mol Immunol, 1996, 33: 1113-8<br>Lehrer et al. Crit Rev Food Sci Nutr, 1996, 36: 553-64 |
| Dog | Can f I and Can f 2, salivary lipocalins | Konieczny et al. Immunology, 1997, 92: 577-86<br>Spitzauer et al. J Allergy Clin Immunol, 1994, 93: 614-27<br>Vrtala et al. J Immunol, 1998, 160: 6137-44 |
| Horse | Equ c1 (major allergen, a lipocalin) | Gregoire et al. J Biol Chem, 1996, 271: 32951-9 |
| Mouse | mouse urinary protein (MUP) | Konieczny et al. Immunology, 1997, 92: 577-86 |
| OTHER MAMMALIAN ALLERGENS |  |  |
| Insulin |  | Ganz et al. J Allergy Clin Immunol, 1990, 86: 45-51<br>Grammer et al. J Lab Clin Med, 1987, 109: 141-6<br>Gonzalo et al. Allergy, 1998, 53: 106-7 |
| Interferons | interferon alpha 2c | Detmar et al. Contact Dermatis, 1989, 20: 149-50 |
| MOLLUSCS | topomyosin | Leung et al. J Allergy Clin Immunol, 1996, 98: 954-61 |
| PLANT ALLERGENS: |  |  |
| Barley | Hor v 9 | Astwood et al. Adv Exp Med Biol, 1996, 409: 269-77 |
| Birch | pollen allergen, Bet v 4<br>rBet v 1 Bet v 2: (profilin) | Twardosz et al. Biochem Bioph. Res Comm., 1997, 239: 197<br>Pauli et al. J Allergy Clin Immunol, 1996, 97: 1100-9<br>van Neerven et al. Clin Exp Allergy, 1998, 28: 423-33<br>Jahn-Schmid et al. Immunotechnology, 1996, 2: 103-13<br>Breitwieser et al. Biotechniques, 1996, 21: 918-25<br>Fuchs et al. J Allergy Clin Immunol, 1997, 100: 3 56-64 |
| Brazil nut | globulin | Bartolome et al. Allergol Immunopathol, 1997, 25: 135-44 |
| Cherry | Pru a I (major allergen) | Scheurer et al. Mol Immunol, 1997, 34: 619-29 |
| Corn | Zml3 (pollen) | Heiss et al. FEBS Lett, 1996, 381: 217-21<br>Lehrer et al. Int Arch Allergy Immunol, 1997, 113: 122-4 |
| Grass | Phl p 1, Phl p 2, Phl p 5 (timothy grass pollen) | Bufe et al. Am J Respir Crit Care Med, 1998, 157: 1269-76<br>Vrtala et al. J Immunol Jun. 15, 1998, 160: 6137-44<br>Niederberger et al. J Allergy Clin Immun., 1998, 101: 258-64 |
|  | Hol 1 5 velvet grass pollen | Schramm et al. Eur J Biochem, 1998, 252: 200-6 |
|  | Bluegrass allergen | Zhang et al. J Immunol, 1993, 151: 791-9 |
|  | Cyn d 7 Bermuda grass | Smith et al. Int Arch Allergy Immunol, 1997, 114: 265-71 |
|  | Cyn d 12 (a profilin) | Asturias et al. Clin Exp Allergy, 1997, 27: 1307-13<br>Fuchs et al. J Allergy Clin Immunol, 1997, 100: 356-64 |
| Japanese Cedar | Jun a 2 (*Juniperus ashei*) | Yokoyama et al. Biochem. Biophys. Res. Commun., 2000, 275: 195-202 |
|  | Cry j 1, Cry j 2 (*Cryptomeria japonica*) | Kingetsu et al. Immunology, 2000, 99: 625-629 |

TABLE 1-continued

RECOMBINANT ALLERGENS

| Group | Allergen | Reference |
|---|---|---|
| Juniper | Jun o 2 (pollen) | Tinghino et al. J Allergy Clin Immunol, 1998, 101: 772-7 |
| Latex | Hev b 7 | Sowka et al. Eur J Biochem, 1998, 255: 213-9 |
| | | Fuchs et al. J Allergy Clin Immunol, 1997, 100: 356-64 |
| *Mercurialis* | Mer a I (profilin) | Vallverdu et al. J Allergy Clin Immunol, 1998, 101: 3 63-70 |
| Mustard (Yellow) | Sin a I (seed) | Gonzalez de la Pena et al. Biochem Bioph. Res Comm., 1993, 190: 648-53 |
| Oilseed rape | Bra r I pollen allergen | Smith et al. Int Arch Allergy Immunol, 1997, 114: 265-71 |
| Peanut | Ara h I | Stanley et al. Adv Exp Med Biol, 1996, 409: 213-6 |
| | Ara h II | Burks et al. J Clin Invest, 1995, 96: 1715-21 |
| | | Burks et al. Int Arch Allergy Immunol, 1995, 107: 248-50 |
| *Poa pratensis* | Poa p9 | Parronchi et al. Eur J Immunol, 1996, 26: 697-703 |
| | | Astwood et al. Adv Exp Med Biol, 1996, 409: 269-77 |
| Ragweed | Amb a I | Sun et al. Biotechnology August 1995, 13: 779-86 |
| | | Hirschwehr et al. J Allergy Clin Immunol, 1998, 101: 196-206 |
| | | Casale et al. J Allergy Clin Immunol, 1997, 100: 110-21 |
| Rye | Lol p I | Tamborini et al. Eur J Biochem, 1997, 249: 886-94 |
| Walnut | Jug r I | Teuber et al. J Allergy Clin Immun., 1998, 101: 807-14 |
| Wheat | allergen | Fuchs et al. J Allergy Clin Immunol, 1997, 100: 356-64 |
| | | Donovan et al. Electrophoresis, 1993, 14: 917-22 |
| FUNGI: | | |
| *Aspergillus* | Asp f 1, Asp f 2, Asp f3, Asp f 4, rAsp f 6 | Crameri et al. Mycoses, 1998, 41 Suppl 1: 56-60 |
| | | Hemmann et al. Eur J Immunol, 1998, 28: 1155-60 |
| | | Banerjee et al. J Allergy Clin Immunol, 1997, 99: 821-7 |
| | | Crameri Int Arch Allergy Immunol, 1998, 115: 99-114 |
| | | Crameri et al. Adv Exp Med Biol, 1996, 409: 111-6 |
| | | Moser et al. J Allergy Clin Immunol, 1994, 93: 1-11 |
| | Manganese superoxide dismutase (MNSOD) | Mayer et al. Int Arch Allergy Immunol, 1997, 113: 213-5 |
| *Blomia* | allergen | Caraballo et al. Adv Exp Med Biol, 1996, 409: 81-3 |
| *Penicillinium* | allergen | Shen et al. Clin Exp Allergy, 1997, 27: 682-90 |
| *Psilocybe* | Psi c 2 | Horner et al. Int Arch Allergy Immunol, 1995, 107: 298-300 |

In some embodiments, the antigen is from an infectious agent, including protozoan, bacterial, fungal (including unicellular and multicellular), and viral infectious agents. Examples of suitable viral antigens are described herein and are known in the art. Bacteria include *Hemophilus influenza, Mycobacterium tuberculosis* and *Bordetella pertussis*. Protozoan infectious agents include malarial plasmodia, *Leishmania* species, *Trypanosoma* species and *Schistosoma* species. Fungi include *Candida albicans*.

In some embodiments, the antigen is a viral antigen. Viral polypeptide antigens include, but are not limited to, HIV proteins such as HIV gag proteins (including, but not limited to, membrane anchoring (MA) protein, core capsid (CA) protein and nucleocapsid (NC) protein), HIV polymerase, influenza virus matrix (M) protein and influenza virus nucleocapsid (NP) protein, hepatitis B surface antigen (HBsAg), hepatitis B core protein (HBcAg), hepatitis e protein (HBeAg), hepatitis B DNA polymerase, hepatitis C antigens, and the like. References discussing influenza vaccination include Scherle and Gerhard (1988) *Proc. Natl. Acad. Sci. USA* 85:4446-4450; Scherle and Gerhard (1986) *J. Exp. Med.* 164:1114-1128; Granoff et al. (1993) *Vaccine* 11:S46-51; Kodihalli et al. (1997) *J. Virol.* 71:3391-3396; Ahmeida et al. (1993) *Vaccine* 11:1302-1309; Chen et al. (1999) *Vaccine* 17:653-659; Govorkova and Smirnov (1997) *Acta Virol.* (1997) 41:251-257; Koide et al. (1995) *Vaccine* 13:3-5; Mbawuike et al. (1994) *Vaccine* 12:1340-1348; Tamura et al. (1994) *Vaccine* 12:310-316; Tamura et al. (1992) *Eur. J. Immunol.* 22:477-481; Hirabayashi et al. (1990) *Vaccine* 8:595-599. Other examples of antigen polypeptides are group- or sub-group specific antigens, which are known for a number of infectious agents, including, but not limited to, adenovirus, herpes simplex virus, papilloma virus, respiratory syncytial virus and poxviruses.

Many antigenic peptides and proteins are known, and available in the art; others can be identified using conventional techniques. For immunization against tumor formation or treatment of existing tumors, immunomodulatory peptides can include tumor cells (live or irradiated), tumor cell extracts, or protein subunits of tumor antigens such as Her-2/neu, Mart1, carcinoembryonic antigen (CEA), gangliosides, human milk fat globule (HMFG), mucin (MUC1), MAGE antigens, BAGE antigens, GAGE antigens, gp100, prostate specific antigen (PSA), and tyrosinase. Vaccines for immuno-based contraception can be formed by including sperm proteins administered with ISS. Lea et al. (1996) *Biochim. Biophys. Acta* 1307:263.

Attenuated and inactivated viruses are suitable for use herein as the antigen. Preparation of these viruses is well-known in the art and many are commercially available (see, e.g., Physicians' Desk Reference (1998) 52nd edition, Medical Economics Company, Inc.). For example, polio virus is available as IPOL® (Pasteur Merieux Connaught) and ORIMUNE® (Lederle Laboratories), hepatitis A virus as VAQTA® (Merck), measles virus as ATTENUVAX® (Merck), mumps virus as MUMPSVAX® (Merck) and rubella virus as MERUVAX®II (Merck). Additionally, attenuated and inactivated viruses such as HIV-1, HIV-2, herpes simplex virus, hepatitis B virus, rotavirus, human and non-human papillomavirus and slow brain viruses can provide peptide antigens. In some embodiments, the antigen comprises a viral vector, such as vaccinia, adenovirus, and canary pox.

Antigens may be isolated from their source using purification techniques known in the art or, more conveniently, may be produced using recombinant methods. Antigenic peptides can include purified native peptides, synthetic peptides, recombinant proteins, crude protein extracts, attenuated or inactivated viruses, cells, micro-organisms, or fragments of such peptides. Immunomodulatory peptides can be native or synthesized chemically or enzymatically. Any method of chemical synthesis known in the art is suitable. Solution phase peptide synthesis can be used to construct peptides of moderate size or, for the chemical construction of peptides, solid phase synthesis can be employed. Atherton et al. (1981) *Hoppe Seylers Z. Physiol. Chem.* 362:833-839. Proteolytic enzymes can also be utilized to couple amino acids to produce peptides. Kullmann (1987) Enzymatic Peptide Synthesis, CRC Press, Inc. Alternatively, the peptide can be obtained by using the biochemical machinery of a cell, or by isolation from a biological source. Recombinant DNA techniques can be employed for the production of peptides. Hames et al. (1987) Transcription and Translation: A Practical Approach, IRL Press. Peptides can also be isolated using standard techniques such as affinity chromatography.

Preferably the antigens are peptides, lipids (e.g., sterols excluding cholesterol, fatty acids, and phospholipids), polysaccharides such as those used in *H. influenza* vaccines, gangliosides and glycoproteins. These can be obtained through several methods known in the art, including isolation and synthesis using chemical and enzymatic methods. In certain cases, such as for many sterols, fatty acids and phospholipids, the antigenic portions of the molecules are commercially available.

Examples of viral antigens useful in the subject compositions and methods using the compositions include, but are not limited to, HIV antigens. Such antigens include, but are not limited to, those antigens derived from HIV envelope glycoproteins including, but not limited to, gp160, gp120 and gp41. Numerous sequences for HIV genes and antigens are known. For example, the Los Alamos National Laboratory HIV Sequence Database collects, curates and annotates HIV nucleotide and amino acid sequences. This database is accessible via the internet and in a yearly publication, see Human Retroviruses and AIDS Compendium (for example, 2000 edition).

Antigens derived from infectious agents may be obtained using methods known in the art, for example, from native viral or bacterial extracts, from cells infected with the infectious agent, from purified polypeptides, from recombinantly produced polypeptides and/or as synthetic peptides.

ISS-Antigen

When used with antigen, ISS may be administered with antigen in a number of ways. In some embodiments, an ISS and antigen may be administered spatially proximate with respect to each other, or as an admixture (i.e., in solution). As described below, spatial proximation can be accomplished in a number of ways, including conjugation (linkage), encapsidation, via affixation to a platform or adsorption onto a surface. Generally, and most preferably, an ISS and antigen are proximately associated at a distance effective to enhance the immune response generated compared to the administration of the ISS and the antigen as an admixture.

In some embodiments, the ISS is conjugated with the antigen. The ISS portion can be coupled with the antigen portion of a conjugate in a variety of ways, including covalent and/or non-covalent interactions.

The link between the portions can be made at the 3' or 5' end of the ISS, or at a suitably modified base at an internal position in the ISS. If the antigen is a peptide and contains a suitable reactive group (e.g., an N-hydroxysuccinimide ester) it can be reacted directly with the $N^4$ amino group of cytosine residues. Depending on the number and location of cytosine residues in the ISS, specific coupling at one or more residues can be achieved.

Alternatively, modified oligonucleosides, such as are known in the art, can be incorporated at either terminus, or at internal positions in the ISS. These can contain blocked functional groups which, when deblocked, are reactive with a variety of functional groups which can be present on, or attached to, the antigen of interest.

Where the antigen is a peptide or polypeptide, this portion of the conjugate can be attached to the 3'-end of the ISS through solid support chemistry. For example, the ISS portion can be added to a polypeptide portion that has been pre-synthesized on a support. Haralambidis et al. (1990a) *Nucleic Acids Res.* 18:493-499; and Haralambidis et al. (1990b) *Nucleic Acids Res.* 18:501-505. Alternatively, the ISS can be synthesized such that it is connected to a solid support through a cleavable linker extending from the 3'-end. Upon chemical cleavage of the ISS from the support, a terminal thiol group is left at the 3'-end of the oligonucleotide (Zuckermann et al. (1987) *Nucleic Acids Res.* 15:5305-5321; and Corey et al. (1987) *Science* 238:1401-1403) or a terminal amino group is left at the 3'-end of the oligonucleotide (Nelson et al. (1989) *Nucleic Acids Res.* 17:1781-1794). Conjugation of the amino-modified ISS to amino groups of the peptide can be performed as described in Benoit et al. (1987) *Neuromethods* 6:43-72. Conjugation of the thiol-modified ISS to carboxyl groups of the peptide can be performed as described in Sinah et al. (1991) *Oligonucleotide Analogues: A Practical Approach*, IRL Press. Coupling of an oligonucleotide carrying an appended maleimide to the thiol side chain of a cysteine residue of a peptide has also been described. Tung et al. (1991) *Bioconjug. Chem.* 2:464-465.

The peptide or polypeptide portion of the conjugate can be attached to the 5'-end of the ISS through an amine, thiol, or carboxyl group that has been incorporated into the oligonucleotide during its synthesis. Preferably, while the oligonucleotide is fixed to the solid support, a linking group comprising a protected amine, thiol, or carboxyl at one end, and a phosphoramidite at the other, is covalently attached to the 5'-hydroxyl. Subsequent to deprotection, the amine, thiol, and carboxyl functionalities can be used to covalently attach the oligonucleotide to a peptide. Benoit et al. (1987); and Sinah et al. (1991).

An ISS-antigen conjugate can also be formed through non-covalent interactions, such as ionic bonds, hydrophobic interactions, hydrogen bonds and/or van der Waals attractions.

Non-covalently linked conjugates can include a non-covalent interaction such as a biotin-streptavidin complex. A biotinyl group can be attached, for example, to a modified base of an ISS. Roget et al. (1989) *Nucleic Acids Res.* 17:7643-7651. Incorporation of a streptavidin moiety into the peptide portion allows formation of a non-covalently bound complex of the streptavidin conjugated peptide and the biotinylated oligonucleotide.

Non-covalent associations can also occur through ionic interactions involving an ISS and residues within the antigen, such as charged amino acids, or through the use of a linker portion comprising charged residues that can interact with both the oligonucleotide and the antigen. For example, non-covalent conjugation can occur between a generally negatively-charged ISS and positively-charged amino acid residues of a peptide, e.g., polylysine, polyarginine and polyhistidine residues.

Non-covalent conjugation between ISS and antigens can occur through DNA binding motifs of molecules that interact with DNA as their natural ligands. For example, such DNA binding motifs can be found in transcription factors and anti-DNA antibodies.

The linkage of the ISS to a lipid can be formed using standard methods. These methods include, but are not limited to, the synthesis of oligonucleotide-phospholipid conjugates (Yanagawa et al. (1988) *Nucleic Acids Symp. Ser.* 19:189-192), oligonucleotide-fatty acid conjugates (Grabarek et al. (1990) *Anal. Biochem.* 185:131-135; and Staros et al. (1986) *Anal. Biochem.* 156:220-222), and oligonucleotide-sterol conjugates. Boujrad et al. (1993) *Proc. Natl. Acad. Sci. USA* 90:5728-5731.

The linkage of the oligonucleotide to an oligosaccharide can be formed using standard known methods. These methods include, but are not limited to, the synthesis of oligonucleotide-oligosaccharide conjugates, wherein the oligosaccharide is a moiety of an immunoglobulin. O'Shannessy et al. (1985) *J. Applied Biochem.* 7:347-355.

The linkage of a circular ISS to a peptide or antigen can be formed in several ways. Where the circular ISS is synthesized using recombinant or chemical methods, a modified nucleoside is suitable. Ruth (1991) in *Oligonucleotides and Analogues: A Practical Approach*, IRL Press. Standard linking technology can then be used to connect the circular ISS to the antigen or other peptide. Goodchild (1990) *Bioconjug. Chem.* 1:165. Where the circular ISS is isolated, or synthesized using recombinant or chemical methods, the linkage can be formed by chemically activating, or photoactivating, a reactive group (e.g. carbene, radical) that has been incorporated into the antigen or other peptide.

Additional methods for the attachment of peptides and other molecules to oligonucleotides can be found in U.S. Pat. No. 5,391,723; Kessler (1992) "Nonradioactive labeling methods for nucleic acids" in Kricka (ed.) *Nonisotopic DNA Probe Techniques*, Academic Press; and Geoghegan et al. (1992) *Bioconjug. Chem.* 3:138-146.

An ISS may be proximately associated with an antigen(s) in other ways. In some embodiments, an ISS and antigen are proximately associated by encapsulation. In other embodiments, an ISS and antigen are proximately associated by linkage to a platform molecule. A "platform molecule" (also termed "platform") is a molecule containing sites which allow for attachment of the ISS and antigen(s). In other embodiments, an ISS and antigen are proximately associated by adsorption onto a surface, preferably a carrier particle.

In some embodiments, the methods of the invention employ an encapsulating agent that can maintain the proximate association of the ISS and first antigen until the complex is available to the target (or compositions comprising such encapsulating agents). Preferably, the composition comprising ISS, antigen and encapsulating agent is in the form of adjuvant oil-in-water emulsions, microparticles and/or liposomes. More preferably, adjuvant oil-in-water emulsions, microparticles and/or liposomes encapsulating an ISS-immunomodulatory molecule are in the form of particles from about 0.04 µm to about 100 µm in size, preferably any of the following ranges: from about 0.1 µm to about 20 µm; from about 0.15 µm to about 10 µm; from about 0.05 µm to about 1.00 µm; from about 0.05 µm to about 0.5 µm.

Colloidal dispersion systems, such as microspheres, beads, macromolecular complexes, nanocapsules and lipid-based system, such as oil-in-water emulsions, micelles, mixed micelles and liposomes can provide effective encapsulation of ISS-containing compositions.

The encapsulation composition further comprises any of a wide variety of components. These include, but are not limited to, alum, lipids, phospholipids, lipid membrane structures (LMS), polyethylene glycol (PEG) and other polymers, such as polypeptides, glycopeptides, and polysaccharides.

Polypeptides suitable for encapsulation components include any known in the art and include, but are not limited to, fatty acid binding proteins. Modified polypeptides contain any of a variety of modifications, including, but not limited to glycosylation, phosphorylation, myristylation, sulfation and hydroxylation. As used herein, a suitable polypeptide is one that will protect an ISS-containing composition to preserve the immunomodulatory activity thereof. Examples of binding proteins include, but are not limited to, albumins such as bovine serum albumin (BSA) and pea albumin.

Other suitable polymers can be any known in the art of pharmaceuticals and include, but are not limited to, naturally-occurring polymers such as dextrans, hydroxyethyl starch, and polysaccharides, and synthetic polymers. Examples of naturally occurring polymers include proteins, glycopeptides, polysaccharides, dextran and lipids. The additional polymer can be a synthetic polymer. Examples of synthetic polymers which are suitable for use in the present invention include, but are not limited to, polyalkyl glycols (PAG) such as PEG, polyoxyethylated polyols (POP), such as polyoxyethylated glycerol (POG), polytrimethylene glycol (PTG) polypropylene glycol (PPG), polyhydroxyethyl methacrylate, polyvinyl alcohol (PVA), polyacrylic acid, polyethyloxazoline, polyacrylamide, polyvinylpyrrolidone (PVP), polyamino acids, polyurethane and polyphosphazene. The synthetic polymers can also be linear or branched, substituted or unsubstituted, homopolymeric, co-polymers, or block co-polymers of two or more different synthetic monomers.

The PEGs for use in encapsulation compositions of the present invention are either purchased from chemical suppliers or synthesized using techniques known to those of skill in the art.

The term "LMS", as used herein, means lamellar lipid particles wherein polar head groups of a polar lipid are arranged to face an aqueous phase of an interface to form membrane structures. Examples of the LMSs include liposomes, micelles, cochleates (i.e., generally cylindrical liposomes), microemulsions, unilamellar vesicles, multilamellar vesicles, and the like.

A preferred colloidal dispersion system of this invention is a liposome. In mice immunized with a liposome-encapsulated antigen, liposomes appeared to enhance a Th1-type immune response to the antigen. Aramaki et al. (1995) *Vaccine* 13:1809-1814. As used herein, a "liposome" or "lipid vesicle" is a small vesicle bounded by at least one and possibly more than one bilayer lipid membrane. Liposomes are made artificially from phospholipids, glycolipids, lipids, steroids such as cholesterol, related molecules, or a combination thereof by any technique known in the art, including but not limited to sonication, extrusion, or removal of detergent from lipid-detergent complexes. A liposome can also optionally comprise additional components, such as a tissue targeting component. It is understood that a "lipid membrane" or "lipid bilayer" need not consist exclusively of lipids, but can additionally contain any suitable other components, including, but not limited to, cholesterol and other steroids, lipid-soluble chemicals, proteins of any length, and other amphipathic molecules, providing the general structure of the membrane is a sheet of two hydrophilic surfaces sandwiching a hydrophobic core. For a general discussion of membrane structure, see *The Encyclopedia of Molecular Biology* by J. Kendrew (1994). For suitable lipids see e.g., Lasic (1993) "Liposomes: from Physics to Applications" Elsevier, Amsterdam.

Processes for preparing liposomes containing ISS-containing compositions are known in the art. The lipid vesicles can be prepared by any suitable technique known in the art. Methods include, but are not limited to, microencapsulation, microfluidization, LLC method, ethanol injection, freon injection, the "bubble" method, detergent dialysis, hydration, sonication, and reverse-phase evaporation. Reviewed in Watwe et al. (1995) *Curr. Sci.* 68:715-724. Techniques may be combined in order to provide vesicles with the most desirable attributes.

The invention encompasses use of LMSs containing tissue or cellular targeting components. Such targeting components are components of a LMS that enhance its accumulation at certain tissue or cellular sites in preference to other tissue or cellular sites when administered to an intact animal, organ, or cell culture. A targeting component is generally accessible from outside the liposome, and is therefore preferably either bound to the outer surface or inserted into the outer lipid bilayer. A targeting component can be inter alia a peptide, a region of a larger peptide, an antibody specific for a cell surface molecule or marker, or antigen binding fragment thereof, a nucleic acid, a carbohydrate, a region of a complex carbohydrate, a special lipid, or a small molecule such as a drug, hormone, or hapten, attached to any of the aforementioned molecules. Antibodies with specificity toward cell type-specific cell surface markers are known in the art and are readily prepared by methods known in the art.

The LMSs can be targeted to any cell type toward which a therapeutic treatment is to be directed, e.g., a cell type which can modulate and/or participate in an immune response. Such target cells and organs include, but are not limited to, APCs, such as macrophages, dendritic cells and lymphocytes, lymphatic structures, such as lymph nodes and the spleen, and nonlymphatic structures, particularly those in which dendritic cells are found.

The LMS compositions of the present invention can additionally comprise surfactants. Surfactants can be cationic, anionic, amphiphilic, or nonionic. One class of surfactants that can be used is nonionic surfactants; particularly preferred are those that are water soluble.

In embodiments in which an ISS and antigen are proximately associated by linkage to a platform molecule, the platform may be proteinaceous or non-proteinaceous (i.e., organic). Examples of proteinaceous platforms include, but are not limited to, albumin, gammaglobulin, immunoglobulin (IgG) and ovalbumin. Borel et al. (1990) *Immunol. Methods* 126:159-168; Dumas et al. (1995) *Arch. Dematol. Res.* 287: 123-128; Borel et al. (1995) *Int. Arch. Allergy Immunol.* 107: 264-267; Borel et al. (1996) *Ann. N.Y. Acad. Sci.* 778:80-87. A platform is multi-valent (i.e., contains more than one binding, or linking, site) to accommodate binding to both an ISS and antigen. Accordingly, a platform may contain 2 or more, 3 or more, 4 or more, 5 or more, 6 or more, 7 or more, 8 or more, 9 or more, 10 or more binding or linking sites Other examples of polymeric platforms are dextran, polyacrylamide, ficoll, carboxymethylcellulose, polyvinyl alcohol, and poly D-glutamic acid/D-lysine.

The principles of using platform molecules are well understood in the art. Generally, a platform contains, or is derivatized to contain, appropriate binding sites for ISS and antigen. In addition, or alternatively, ISS and/or antigen is derivatized to provide appropriate linkage groups. For example, a simple platform is a bi-functional linker (i.e., has two binding sites), such as a peptide. Further examples are discussed below.

Platform molecules may be biologically stabilized, i.e., they exhibit an in vivo excretion half-life often of hours to days to months to confer therapeutic efficacy, and are preferably composed of a synthetic single chain of defined composition. They generally have a molecular weight in the range of about 200 to about 1,000,000, preferably any of the following ranges: from about 200 to about 500,000; from about 200 to about 200,000; from about 200 to about 50,000 (or less, such as 30,000). Examples of valency platform molecules are polymers (or are comprised of polymers) such as polyethylene glycol (PEG; preferably having a molecular weight of about 200 to about 8000), poly-D-lysine, polyvinyl alcohol, polyvinylpyrrolidone, D-glutamic acid and D-lysine (in a ratio of 3:2). Other molecules that may be used are albumin and IgG.

Other platform molecules suitable for use within the present invention are the chemically-defined, non-polymeric valency platform molecules disclosed in U.S. Pat. No. 5,552, 391. Other homogeneous chemically-defined valency platform molecules suitable for use within the present invention are derivatized 2,2'-ethylenedioxydiethylamine (EDDA) and triethylene glycol (TEG).

Additional suitable valency platform molecules include, but are not limited to, tetraminobenzene, heptaminobetacyclodextrin, tetraminopentaerythritol, 1,4,8,11-tetraazacyclotetradecane (Cyclam) and 1,4,7,10-tetraazacyclododecane (Cyclen).

In general, these platforms are made by standard chemical synthesis techniques. PEG must be derivatized and made multivalent, which is accomplished using standard techniques. Some substances suitable for conjugate synthesis, such as PEG, albumin, and IgG are available commercially.

Conjugation of an ISS and antigen to a platform molecule may be effected in any number of ways, typically involving one or more crosslinking agents and functional groups on the antigen and ISS platform and platform molecule. Platforms and ISS and antigen must have appropriate linking groups. Linking groups are added to platforms using standard synthetic chemistry techniques. Linking groups may be added to polypeptide antigens and ISS using either standard solid phase synthetic techniques or recombinant techniques. Recombinant approaches may require post-translational modification in order to attach a linker, and such methods are known in the art.

As an example, polypeptides contain amino acid side chain moieties containing functional groups such as amino, carboxyl or sulfhydryl groups that serve as sites for coupling the polypeptide to the platform. Residues that have such functional groups may be added to the polypeptide if the polypeptide does not already contain these groups. Such residues may be incorporated by solid phase synthesis techniques or recombinant techniques, both of which are well known in the peptide synthesis arts. When the polypeptide has a carbohydrate side chain(s) (or if the antigen is a carbohydrate), functional amino, sulfhydryl and/or aldehyde groups may be incorporated therein by conventional chemistry. For instance, primary amino groups may be incorporated by reaction of the oxidized sugar with ethylenediamine in the presence of sodium cyanoborohydride, sulfhydryls may be introduced by reaction of cysteamine dihydrochloride followed by reduction with a standard disulfide reducing agent, while aldehyde groups may be generated following periodate oxidation. In a similar fashion, the platform molecule may also be derivatized to contain functional groups if it does not already possess appropriate functional groups.

Hydrophilic linkers of variable lengths are useful for connecting ISS and antigen to platform molecules. Suitable linkers include linear oligomers or polymers of ethylene glycol. Such linkers include linkers with the formula $R^1S(CH_2CH_2O)_nCH_2CH_2O(CH_2)_mCO_2R^2$ wherein n=0-200, m=1 or 2, $R^1$=H or a protecting group such as trityl, $R^2$=H or alkyl or aryl, e.g., 4-nitrophenyl ester. These linkers are useful in connecting a molecule containing a thiol reactive group such as haloaceyl, maleiamide, etc., via a thioether to a second molecule which contains an amino group via an amide bond. These linkers are flexible with regard to the order of attachment, i.e., the thioether can be formed first or last.

In embodiments in which an ISS and antigen are proximately associated by adsorption onto a surface, the surface may be in the form of a carrier particle (for example, a nanoparticle) made with either an inorganic or organic core. Examples of such nanoparticles include, but are not limited to, nanocrystalline particles, nanoparticles made by the polymerization of alkylcyanoacrylates and nanoparticles made by the polymerization of methylidene malonate. Additional surfaces to which an ISS and antigen may be adsorbed include, but are not limited to, activated carbon particles and protein-ceramic nanoplates. Other examples of carrier particles are provided herein.

Adsorption of polynucleotides and polypeptides to a surface for the purpose of delivery of the adsorbed molecules to cells is well known in the art. See, for example, Douglas et al. (1987) Crit. Rev. Ther. Drug. Carrier Syst. 3:233-261; Hagiwara et al. (1987) In Vivo 1:241-252; Bousquet et al. (1999) Pharm. Res. 16:141-147; and Kossovsky et al., U.S. Pat. No. 5,460,831. Preferably, the material comprising the adsorbent surface is biodegradable. Adsorption of an ISS and/or antigen to a surface may occur through non-covalent interactions, including ionic and/or hydrophobic interactions.

In general, characteristics of carriers such as nanoparticles, such as surface charge, particle size and molecular weight, depend upon polymerization conditions, monomer concentration and the presence of stabilizers during the polymerization process (Douglas et al., 1987). The surface of carrier particles may be modified, for example, with a surface coating, to allow or enhance adsorption of the ISS and/or antigen. Carrier particles with adsorbed ISS and/or antigen may be further coated with other substances. The addition of such other substances may, for example, prolong the half-life of the particles once administered to the subject and/or may target the particles to a specific cell type or tissue, as described herein.

Nanocrystalline surfaces to which an ISS and antigen may be adsorbed have been described (see, for example, U.S. Pat. No. 5,460,831). Nanocrystalline core particles (with diameters of 1 µm or less) are coated with a surface energy modifying layer that promotes adsorption of polypeptides, polynucleotides and/or other pharmaceutical agents. As described in U.S. Pat. No. 5,460,831, for example, a core particle is coated with a surface that promotes adsorption of an oligonucleotide and is subsequently coated with an antigen preparation, for example, in the form of a lipid-antigen mixture. Such nanoparticles are self-assembling complexes of nanometer sized particles, typically on the order of 0.1 µm, that carry an inner layer of ISS and an outer layer of antigen.

Another adsorbent surface are nanoparticles made by the polymerization of alkylcyanoacrylates. Alkylcyanoacrylates can be polymerized in acidified aqueous media by a process of anionic polymerization. Depending on the polymerization conditions, the small particles tend to have sizes in the range of 20 to 3000 nm, and it is possible to make nanoparticles specific surface characteristics and with specific surface charges (Douglas et al., 1987). For example, oligonucleotides may be adsorbed to polyisobutyl- and polyisohexlcyanoacrylate nanoparticles in the presence of hydrophobic cations such as tetraphenylphosphonium chloride or quaternary ammonium salts, such as cetyltrimethyl ammonium bromide. Oligonucleotide adsorption on these nanoparticles appears to be mediated by the formation of ion pairs between negatively charged phosphate groups of the nucleic acid chain and the hydrophobic cations. See, for example, Lambert et al. (1998) Biochimie 80:969-976, Chavany et al. (1994) Pharm. Res. 11:1370-1378; Chavany et al. (1992) Pharm. Res. 9:441-449. Polypeptides may also be adsorbed to polyalkylcyanoacrylate nanoparticles. See, for example, Douglas et al., 1987; Schroeder et al. (1998) Peptides 19:777-780.

Another adsorbent surface is nanoparticles made by the polymerization of methylidene malonate. For example, as described in Bousquet et al., 1999, polypeptides adsorbed to poly(methylidene malonate 2.1.2) nanoparticles appear to do so initially through electrostatic forces followed by stabilization through hydrophobic forces.

ISS/MC Complexes

ISSs may be administered in the form of ISS/microcarrier (ISS/MC) complexes. Accordingly, the invention provides compositions comprising ISS/MC complexes.

Microcarriers useful in the invention are less than about 150, 120 or 100 µm in size, more commonly less than about 50-60 µm in size, preferably less than about 10 µm in size, and are insoluble in pure water. Microcarriers used in the invention are preferably biodegradable, although nonbiodegradable microcarriers are acceptable. Microcarriers are commonly solid phase, such as "beads" or other particles, although liquid phase microcarriers such as oil in water emulsions comprising a biodegradable polymers or oils are also contemplated. A wide variety of biodegradable and nonbiodegradable materials acceptable for use as microcarriers are known in the art.

Microcarriers for use in the compositions or methods of the invention are generally less than about 10 µm in size (e.g., have an average diameter of less than about 10 µm, or at least about 97% of the particles pass through a 10 µm screen filter), and include nanocarriers (i.e., carriers of less than about 1 µm size). Preferably, microcarriers are selected having sizes within an upper limit of about 9, 7, 5, 2, or 1 µm or 900, 800, 700, 600, 500, 400, 300, 250, 200, or 100 nm and an independently selected lower limit of about 4, 2, or 1 µm or about 800, 600, 500, 400, 300, 250, 200, 150, 100, 50, 25, or 10 nm, where the lower limit is less than the upper limit. In some embodiments, the microcarriers have a size of about 1.0-1.5 µm, about 1.0-2.0 µm or about 0.9-1.6 m. In certain preferred embodiments, the microcarriers have a size of about 10 nm to about 5 µm or about 25 nm to about 4.5 µm, about 1 µm, about 1.2 µm, about 1.4 µm, about 1.5 µm, about 1.6 µm, about 1.8 µm, about 2.0 µm, about 2.5 µm or about 4.5 µm. When the microcarriers are nanocarriers, preferred embodiments include nanocarriers of about 25 to about 300 nm, 50 to about 200 nm, about 50 nm or about 200 nm.

Solid phase biodegradable microcarriers may be manufactured from biodegradable polymers including, but not limited to: biodegradable polyesters, such as poly(lactic acid), poly(glycolic acid), and copolymers (including block copolymers) thereof, as well as block copolymers of poly(lactic acid) and poly(ethylene glycol); polyorthoesters such as polymers based on 3,9-diethylidene-2,4,8,10-tetraoxaspiro [5.5]undecane (DETOSU); polyanhydrides such as poly(anhydride) polymers based on relatively hydrophilic monomers such as sebacic acid; polyanhydride imides, such as polyanhydride polymers based on sebacic acid-derived monomers incorporating amino acids (i.e., linked to sebacic acid by imide bonds through the amino-terminal nitrogen) such as glycine or alanine; polyanhydride esters; polyphosphazenes, especially poly(phosphazenes) which contain hydrolysis-sensitive ester groups which can catalyze degradation of the polymer backbone through generation of carboxylic acid groups (Schacht et al., (1996) Biotechnol. Bioeng. 1996:102); and polyamides such as poly(lactic acid-co-lysine).

A wide variety of nonbiodegradable materials suitable for manufacturing microcarriers are also known, including, but not limited to polystyrene, polypropylene, polyethylene, silica, ceramic, polyacrylamide, dextran, hydroxyapatite, latex, gold, and ferromagnetic or paramagnetic materials. Certain embodiments exclude gold, latex, and/or magnetic beads. In certain embodiments, the microcarriers may be made of a first material (e.g., a magnetic material) encapsulated with a second material (e.g., polystyrene).

Solid phase microspheres are prepared using techniques known in the art. For example, they can be prepared by emulsion-solvent extraction/evaporation technique. Generally, in this technique, biodegradable polymers such as polyanhydrates, poly(alkyl-α-cyanoacrylates) and poly(α-hydroxy esters), for example, poly(lactic acid), poly(glycolic acid), poly(D,L-lactic-co-glycolic acid) and poly(caprolactone), are dissolved in a suitable organic solvent, such as methylene chloride, to constitute the dispersed phase (DP) of emulsion. DP is emulsified by high-speed homogenization into excess volume of aqueous continuous phase (CP) that contains a dissolved surfactant, for example, polyvinylalcohol (PVA) or polyvinylpirrolidone (PVP). Surfactant in CP is to ensure the formation of discrete and suitably-sized emulsion droplet. The organic solvent is then extracted into the CP and subsequently evaporated by raising the system temperature. The solid microparticles are then separated by centrifugation or filtration, and dried, for example, by lyophilization or application of vacuum, before storing at 4° C.

Physico-chemical characteristics such as mean size, size distribution and surface charge of dried microspheres may be determined. Size characteristics are determined, for example, by dynamic light scattering technique and the surface charge was determined by measuring the zeta potential.

Liquid phase microcarriers include liposomes, micelles, oil droplets and other lipid or oil-based particles which incorporate biodegradable polymers or oils. In certain embodiments, the biodegradable polymer is a surfactant. In other embodiments, the liquid phase microcarriers are biodegradable due to the inclusion of a biodegradable oil such as squalene or a vegetable oil. One preferred liquid phase microcarrier is oil droplets within an oil-in-water emulsion. Preferably, oil-in-water emulsions used as microcarriers comprise biodegradable substituents such as squalene.

ISS/MC complexes comprise an ISS bound to the surface of a microcarrier (i.e., the ISS is not encapsulated in the MC), and preferably comprise multiple molecules of ISS bound to each microcarrier. In certain embodiments, a mixture of different ISSs may be complexed with a microcarrier, such that the microcarrier is bound to more than one ISS species. The bond between the ISS and MC may be covalent or non-covalent. As will be understood by one of skill in the art, the ISS may be modified or derivatized and the composition of the microcarrier may be selected and/or modified to accommodate the desired type of binding desired for ISS/MC complex formation.

Covalently bonded ISS/MC complexes may be linked using any covalent crosslinking technology known in the art. Typically, the ISS portion will be modified, either to incorporate an additional moiety (e.g., a free amine, carboxyl or sulfhydryl group) or incorporate modified (e.g., phosphorothioate) nucleotide bases to provide a site at which the ISS portion may be linked to the microcarrier. The link between the ISS and MC portions of the complex can be made at the 3' or 5' end of the ISS, or at a suitably modified base at an internal position in the ISS. The microcarrier is generally also modified to incorporate moieties through which a covalent link may be formed, although functional groups normally present on the microcarrier may also be utilized. The ISS/MC is formed by incubating the ISS with a microcarrier under conditions which permit the formation of a covalent complex (e.g., in the presence of a crosslinking agent or by use of an activated microcarrier comprising an activated moiety which will form a covalent bond with the ISS).

A wide variety of crosslinking technologies are known in the art, and include crosslinkers reactive with amino, carboxyl and sulfhydryl groups. As will be apparent to one of skill in the art, the selection of a crosslinking agent and crosslinking protocol will depend on the configuration of the ISS and the microcarrier as well as the desired final configuration of the ISS/MC complex. The crosslinker may be either homobifunctional or heterobifunctional. When a homobifunctional crosslinker is used, the crosslinker exploits the same moiety on the ISS and MC (e.g., an aldehyde crosslinker may be used to covalently link an ISS and MC where both the ISS and MC comprise one or more free amines). Heterobifunctional crosslinkers utilize different moieties on the ISS and MC, (e.g., a maleimido-N-hydroxysuccinimide ester may be used to covalently link a free sulfhydryl on the ISS and a free amine on the MC), and are preferred to minimize formation of inter-microcarrier bonds. In most cases, it is preferable to crosslink through a first crosslinking moiety on the microcarrier and a second crosslinking moiety on the ISS, where the second crosslinking moiety is not present on the microcarrier. One preferred method of producing the ISS/MC complex is by 'activating' the microcarrier by incubating with a heterobifunctional crosslinking agent, then forming the ISS/MC complex by incubating the ISS and activated MC under conditions appropriate for reaction. The crosslinker may incorporate a "spacer" arm between the reactive moieties, or the two reactive moieties in the crosslinker may be directly linked.

In one preferred embodiment, the ISS portion comprises at least one free sulfhydryl (e.g., provided by a 5'-thiol modified base or linker) for crosslinking to the microcarrier, while the microcarrier comprises free amine groups. A heterobifunctional crosslinker reactive with these two groups (e.g., a crosslinker comprising a maleimide group and a NHS-ester), such as succinimidyl 4-(N-maleimidomethyl)cyclohexane-1-carboxylate is used to activate the MC, then covalently crosslink the ISS to form the ISS/MC complex.

Non-covalent ISS/MC complexes may be linked by any non-covalent binding or interaction, including ionic (electrostatic) bonds, hydrophobic interactions, hydrogen bonds, van der Waals attractions, or a combination of two or more different interactions, as is normally the case when a binding pair is to link the ISS and MC.

Preferred non-covalent ISS/MC complexes are typically complexed by hydrophobic or electrostatic (ionic) interactions, or a combination thereof, (e.g., through base pairing between an ISS and a polynucleotide bound to an MC use of a binding pair). Due to the hydrophilic nature of the backbone of polynucleotides, ISS/MC complexes which rely on hydrophobic interactions to form the complex generally require modification of the ISS portion of the complex to incorporate a highly hydrophobic moiety. Preferably, the hydrophobic moiety is biocompatible, nonimmunogenic, and is naturally occurring in the individual for whom the composition is intended (e.g., is found in mammals, particularly humans). Examples of preferred hydrophobic moieties include lipids, steroids, sterols such as cholesterol, and terpenes. The method of linking the hydrophobic moiety to the ISS will, of course, depend on the configuration of the ISS and the identity of the hydrophobic moiety. The hydrophobic moiety may be added at any convenient site in the ISS, preferably at either the 5' or 3' end; in the case of addition of a cholesterol moiety to an ISS, the cholesterol moiety is preferably added to the 5' end of the ISS, using conventional chemical reactions (see, for example, Godard et al. (1995) *Eur. J. Biochem.* 232:404-410). Preferably, microcarriers for use in ISS/MC complexes linked by hydrophobic bonding are made from hydrophobic materials, such as oil droplets or hydrophobic polymers, although hydrophilic materials modified to incorporate hydrophobic moieties may be utilized as well. When the microcarrier is a liposome or other liquid phase microcarrier comprising a lumen, the ISS/MC complex is formed by mixing the ISS and the MC after preparation of the MC, in order to avoid encapsulation of the ISS during the MC preparation process.

Non-covalent ISS/MC complexes bound by electrostatic binding typically exploit the highly negative charge of the polynucleotide backbone. Accordingly, microcarriers for use in non-covalently bound ISS/MC complexes are generally positively charged (cationic) at physiological pH (e.g., about pH 6.8-7.4). The microcarrier may intrinsically possess a positive charge, but microcarriers made from compounds not normally possessing a positive charge may be derivatized or otherwise modified to become positively charged (cationic). For example, the polymer used to make the microcarrier may be derivatized to add positively charged groups, such as primary amines. Alternately, positively charged compounds may be incorporated in the formulation of the microcarrier during manufacture (e.g., positively charged surfactants may be used during the manufacture of poly(lactic acid)/poly(glycolic acid) copolymers to confer a positive charge on the resulting microcarrier particles).

As described herein, to prepare cationic microspheres, cationic lipids or polymers, for example, 1,2-dioleoyl-1,2,3-trimethylammoniopropane (DOTAP), cetyltrimethylammonium bromide (CTAB) or polylysine, are added either to DP or CP, as per their solubility in these phases.

As described herein, ISS/MC complexes can be preformed by adsorption onto cationic microspheres by incubation of polynucleotide and the particles, preferably in an aqueous admixture. Such incubation may be carried out under any desired conditions, including ambient (room) temperature (e.g., approximately 20° C.) or under refrigeration (e.g., 4° C.). Because cationic microspheres and polynucleotides associate relatively quickly, the incubation may be for any convenient time period, such as 5, 10, 15 minutes or more, including overnight and longer incubations. For example, ISSs can be adsorbed onto the cationic microspheres by overnight aqueous incubation of polynucleotide and the particles at 4° C. However, because cationic microspheres and polynucleotides spontaneously associate, the ISS/MC complex can be formed by sISSle co-administration of the polynucleotide and the MC. Microspheres may be characterized for size and surface charge before and after polynucleotide association. Selected batches may then evaluated for activity against suitable controls in, for example, established human peripheral blood mononuclear cell (PBMC), as described herein, and mouse splenocyte assays. The formulations may also evaluated in suitable animal models.

Non-covalent ISS/MC complexes linked by nucleotide base pairing may be produced using conventional methodologies. Generally, base-paired ISS/MC complexes are produced using a microcarrier comprising a bound, preferably a covalently bound, polynucleotide (the "capture polynucleotide") that is at least partially complementary to the ISS. The segment of complementarity between the ISS and the capture nucleotide is preferably at least 6, 8, 10 or 15 contiguous base pairs, more preferably at least 20 contiguous base pairs. The capture nucleotide may be bound to the MC by any method known in the art, and is preferably covalently bound to the ISS at the 5' or 3' end.

In other embodiments, a binding pair may be used to link the ISS and MC in an ISS/MC complex. The binding pair may be a receptor and ligand, an antibody and antigen (or epitope), or any other binding pair which binds at high affinity (e.g., Kd less than about 10-8). One type of preferred binding pair is biotin and streptavidin or biotin and avidin, which form very tight complexes. When using a binding pair to mediate ISS/MC complex binding, the ISS is derivatized, typically by a covalent linkage, with one member of the binding pair, and the MC is derivatized with the other member of the binding pair. Mixture of the two derivatized compounds results in ISS/MC complex formation.

Many ISS/MC complex embodiments do not include an antigen, and certain embodiments exclude antigen(s) associated with the disease or disorder which is the object of the ISS/MC complex therapy. In further embodiments, the ISS is also bound to one or more antigen molecules. Antigen may be coupled with the ISS portion of an ISS/MC complex in a variety of ways, including covalent and/or non-covalent interactions, as described, for example, in WO 98/16247. Alternately, the antigen may be linked to the microcarrier. The link between the antigen and the ISS in ISS/MC complexes comprising an antigen bound to the ISS can be made by techniques described herein and known in the art, including, but not limited to, direct covalent linkage, covalent conjugation via a crosslinker moiety (which may include a spacer arm), noncovalent conjugation via a specific binding pair (e.g., biotin and avidin), and noncovalent conjugation via electrostatic or hydrophobic bonding.

ISS Complexes with Cationic Condensing Agent and Stabilizing Agent

ISSs may be administered as a composition comprising a cationic condensing agent, an ISS, and a stabilizing agent (i.e., CIS composition) for modulating an immune response in the recipient. See, U.S. Patent Application No. 60/402,968. In some embodiments, the CIS composition may also comprise an antigen and/or a fatty acid.

The CIS compositions of the invention are typically in particulate form. As will be apparent to those of skill in the art, CIS particulate compositions of the invention will consist of a population of particles of different sizes. Due to this naturally arising variability, the "size" of the particles in the compositions of the invention may be described in ranges or as a maximum or minimum diameter. Particles are considered to be a particular size if at least 95% of the particles (by mass) meet the specified dimension (e.g., if at least 97% of the particles are less than 20 μm in diameter, then the composition is considered to consist of particles of less than 20 μm in diameter). Particle size may be measured by any convenient method known in the art, including filtration (e.g., use of a "depth" filter to capture particles greater than a cutoff size), dynamic light scattering, electron microscopy, including TEM (particularly in combination with freeze-fracture processing) and SEM, and the like.

Preferably, the CIS compositions of the invention comprise particles which are less than about 50 μm in diameter, more preferably less than about 20 μm in diameter, although in some embodiments the particles will be less than about 3, 2 or 1 μm in diameter. Preferred particle size ranges include about 0.01 μm to 50 μm, 0.02 to 20 μm, 0.05 to 5 μm, and 0.05 to 3 μm in diameter.

The components of the CIS compositions may be present in various ratios/quantities in the compositions, although it is contemplated that the amounts of the stabilizing agent(s) and optional components such as fatty acids and antigen will remain relatively invariant, with stabilizing agents generally ranging from about 0.1% to 0.5% (v/v), fatty acids ranging from about 0 to 0.5%, and antigen concentrations ranging from about 0.1 to about 100 µg/mL, preferably about 1 to about 100 µg/mL, more preferably about 10 to 50 µg/mL. The amounts and ratios of the ISS and the cationic condensing agent are subject to a greater range of variation in the compositions of the invention. The amount of ISS will vary to a certain extent as a function of the molecular weight of the ISS, and generally ranges from about 50 µg/mL to about 2 mg/mL, preferably about 100 µg/mL to 1 mg/mL. The cationic condensing agent is generally present in excess (in terms of mass) over the ISS, generally in ratios of about 1:2 (ISS:cationic condensing agent) to about 1:6, more preferably about 2:5 to 1:5.

Particle size in the CIS compositions is a function of a number of variables. The size distribution of particles in the compositions can be modulated by altering the ratio of cationic condensing agent to ISS. For example, altering the ratio of cationic condensing agent to ISS in the exemplary +ISS/ 0.4% Tween 85/0.4% oleate/polymyxin B compositions can alter mean particle size from about 1.5 µm at cationic condensing agent:IMC=1 to about 45 µm at cationic condensing agent:ISS=10.

In certain embodiments, the CIS compositions comprise a cationic condensing agent, an ISS and a stabilizing agent that is a nonionic detergent. In other embodiments, the compositions comprise a membrane disrupting cationic lipopeptide (preferably a polymyxin, more preferably polymyxin B), an ISS and a stabilizing agent. In some embodiments the stabilizing agent is not a serum protein (particularly not a bovine serum protein). An exemplary composition of this class of embodiments utilizes a polyoxyethylene ether detergent such as Tween 80 or Tween 85 as the stabilizing agent, with oleate as an optional additional stabilizing agent.

In some embodiments, CIS compositions comprise immunomodulatory particles, wherein the particles are made by the process of combining a cationic condensing agent, an ISS and a stabilizing agent that is a nonionic detergent. In other embodiments, compositions of the invention comprise immunomodulatory particles, wherein the particles are made by the process of combining a membrane disrupting cationic lipopeptide (preferably a polymyxin, more preferably polymyxin B), an ISS and a stabilizing agent. In some embodiments, the stabilizing agent is not a serum protein (particularly not a bovine serum protein).

In some embodiments, CIS compositions comprise immunomodulatory particles, wherein the particles are formed by the process of combining an ISS and a stabilizing agent that is a nonionic detergent, thereby forming an ISS/stabilizing agent mixture, and combining a cationic condensing agent with the ISS/stabilizing agent mixture. In other embodiments, compositions of the invention comprise immunomodulatory particles, wherein the particles are formed by the process of combining an ISS and a stabilizing agent, thereby forming an ISS/stabilizing agent mixture, and combining a membrane disrupting cationic lipopeptide (preferably a polymyxin, more preferably polymyxin B) with the ISS/stabilizing agent mixture. In some embodiments, the stabilizing agent is not a serum protein (particularly not a bovine serum protein).

In some embodiments, CIS compositions comprise immunomodulatory particles, wherein the particles comprise a cationic condensing agent, an ISS and a stabilizing agent that is a nonionic detergent. In other embodiments, compositions of the invention comprise immunomodulatory particles, wherein the particles comprise a membrane disrupting cationic lipopeptide (preferably a polymyxin, more preferably polymyxin B), an ISS and a stabilizing agent. In some embodiments, the stabilizing agent is not a serum protein (particularly not a bovine serum protein).

Cationic condensing agents useful in the CIS compositions and methods of using the CIS compositions are molecules which are positively charged at physiological pH (i.e., pH of about 7.0 to about 7.5). Preferably, cationic condensing agents used in the instant invention are not zwitterionic and are polycationic, that is, having more than one positive charge per molecule. Cationic condensing agents useful in the instant invention include hydrophilic or amphipathic polycations.

Preferred cationic condensing agents include: (a) membrane disrupting cationic lipopeptides including, but not limited to polymyxins including polymyxin A, polymyxin B (including polymyxin $B_1$ and polymyxin $B_2$), polymyxin C, polymyxin D, polymyxin E (also known as colistin), polymyxin K, polymyxin M, polymyxin P, polymyxin S and polymyxin T, circulins including circulin A, circulin B, circulin C, circulin D, circulin E and circulin F, octapeptin, amphotericins including amphotericin B, and acylated peptides including octanoyl-KFFKFFKFF (SEQ ID NO: 25) and acyl KALA (octanoyl-WEAKLAKALAKALA-KHLAKALAKALEACEA (SEQ ID NO: 26); (b) membrane disrupting cationic peptides including, but not limited to polymyxin B nonapeptide, cecropins including cecropin A, cecropin B and cecropin P1, KFFKFFKFF (SEQ ID NO: 25) and KALA (WEAKLAKALAKALA-KHLAKALAKALKACEA) (SEQ ID NO: 27); (c) single chain cationic surfactants including, but not limited to cetyltrimethylammonium bromide (CTAB), benzyl-dimethyl-ammonium bromide (BDAB), CpyrB (cetyl-pyridinium bromide), CimB (cetyl imidazolium bromide), and polycationic polymers, including, but not limited to, poly-L-lysine (PLL) and polyethyleneimine (PEI). In certain embodiments, the cationic condensing agent is a membrane disrupting cationic lipopeptide, preferably a polymyxin, more preferably polymyxin B. In some embodiments, cationic condensing agents may exclude fatty acid esters (i.e., lipids) and double chain cationic surfactants.

Stabilizing agents useful in the CIS compositions and methods of using the CIS compositions include those which are suspendable in water and reduce the surface tension of water, although stabilizing agents which are water soluble and/or completely miscible in water are preferred. A number of classes of stabilizing agents are useful in the compositions and methods of the invention, including proteins (preferably hydrophilic proteins), nonionic detergents, polymeric surfactants (e.g., polyvinyl alcohol and polyvinyl pyrrolidone), cationic detergents, anionic detergents and fatty acids, although in certain embodiments, serum proteins (particularly bovine serum proteins), fatty acids, and/or ionic detergents may be excluded from the definition of stabilizing agents.

Any protein may be used as a stabilizing agent in accordance with the invention. In some embodiments, the stabilizing agent is a protein which is not intended as an antigen (see discussion below); in these embodiments, it is preferred that the protein be derived from the same species as the intended recipient of the composition (e.g., if the composition is intended for use in humans, then it is preferred that the protein used as the stabilizing agent be a human protein). Serum albumin is an exemplary protein useful as a stabilizing agent in such embodiments. In other embodiments, an antigen is utilizing as the stabilizing agent, in which case the antigen need not be, and in general is preferably not, species matched with the intended recipient. Antigens useful in the compositions and methods of the invention are disclosed below.

Nonionic detergents useful in the CIS compositions and methods of using the CIS compositions include glucamides such as decyldimethylphosphine oxide (APO-10) and dimethyldodecylphosphine oxide (APO-12), octanoyl-N-methylglucamide (MEGA-8), nonanoyl-N-methylglucamide (MEGA-9) and decanoyl-N-methyl glucamide (MEGA-10), polyoxyethylene ether detergents including polyoxyethylene (10) dodecyl ester (Genapol C100), polyoxyethylene(4) lauryl ether (BRIJ® 30), polyoxyethylene(9) lauryl ether (LUBROL® PX) polyoxyethylene(23) lauryl ether (BRIJ® 35), polyoxyethylene(2) cetyl ether (BRIJ® 52), polyoxyethylene (10) cetyl ether (BRIJ® 56), polyoxyethylene(20) cetyl ether (BRIJ® 58), polyoxyethylene(2) stearyl ether (BRIJ® 72), polyoxyethylene(10) stearyl ether (BRIJ® 76), polyoxyethylene(20) stearyl ether (BRIJ® 78), polyoxyethylene(100) stearyl ether (BRIJ® 700), polyoxyethylene(2) oleyl ether (BRIJ® 92), polyoxyethylene(10) oleyl ether (BRIJ® 97), polyoxyethylene(20) oleyl ether (BRIJ® 98), isotridecylpoly (ethyleneglycolether)$_8$ (Genapol 80), PLURONIC® F-68, PLURONIC® F-127, dodecylpoly(ethyleneglycolether)$_9$ (Thesit) polyoxyethylene(10) isooctylphenyl ether (TRITON® X-100), polyoxyethylene(8) isooctylphenyl ether (TRITON® X-114), polyethylene glycol sorbitan monolaurate (TWEEN® 20), polyoxyethylenesorbitan monopalmitate (TWEEN® 40), polyethylene glycol sorbitan monostearate (TWEEN® 60), polyoxyethylenesorbitan tristearate (TWEEN® 65), polyethylene glycol sorbitan monooleate (TWEEN® 80), polyoxyethylene(20) sorbitan trioleate (TWEEN® 85), poloxamer 188, and polyethyleneglycol-p-isooctylphenyl ether (Nonidet NP40), alkyl maltoside detergents including cyclohexyl-n-ethyl-β-D-maltoside, cyclohexyl-n-hexyl-β-D-maltoside, and cyclohexyl-n-methyl-β-D-maltoside, n-decanoylsucrose, glucopyranosides including methyl 6-O—(N-heptylcarbamoyl)-α-D-glucopyranoside (HECAMEG) and alkyl glucopyranosides such as n-decyl-β-D-glucopyranoside, n-heptyl-β-D-glucopyranoside, n-dodecyl-β-D-glucopyranoside, n-nonyl-β-D-glucopyranoside, n-octyl-α-D-glucopyranoside, and n-octyl-β-D-glucopyranoside, alkyl thioglucopyranosides including n-heptyl-β-D-thioglucopyranoside, alkyl maltopyranosides including n-decyl-β-D-maltopyranoside and n-octyl-β-D-maltopyranoside, n-decyl-β-D-thiomaltoside, digitonin, n-dodecanoyl sucrose, n-dodecyl-β-D-maltoside, heptane 1,2,3-triol, n-octanoyl-β-D-glucosylamine (NOGA), n-octanoyl sucrose, poloxamers (polyoxyethylene/polyoxypropylene block copolymers) such as poloxamer 188 and poloxamer 407, and sulfobetaines including SB-10, SB-12, and SB-14 and n-undecyl-β-D-maltoside. Preferred stabilizing agents include polyoxyethylene ether detergents, particularly polyethylene glycol sorbitan monooleate and polyoxyethylene(20) sorbitan trioleate.

Anionic detergents useful in the CIS compositions and methods of using the CIS compositions include caprylic acid and salts thereof, chenodeoxycholic acid and salts thereof, cholic acid and salts thereof, decanesulfonic acid and salts thereof, deoxycholic acid and salts thereof, glycodeoxycholic acid and salts thereof, lauroylsarcosine and salts thereof, n-dodecyl sulfate and salts thereof (including sodium and lithium salts), taurochenodeoxycholic acid and salts thereof, taurocholic acid and salts thereof, taurodehydrocholic acid and salts thereof, taurodeoxycholic acid and salts thereof, taurolithocholic acid and salts thereof, and tauroursodeoxycholic acid and salts thereof.

Cationic detergents include cetylpyridinium and salts thereof, cetyltrimethylammonia and salts thereof including cetyltrimethylammonium bromide (CTAB), dodecyltrimethylammonia and salts thereof including dedecyltrimethylammonium bromide, alklylammonium imidazolines, quaternary imidazolines, and tetradecyltrimtheylammonia and salts thereof including tetradecyltrimtheylammonium bromide.

Detergents selected for use as stabilizing agents are preferably those that are considered oil/water emulsifying detergents. Oil/water emulsifying detergents are known in the art, and are generally characterized by a hydrophobic/lipophilic balance (HLB) value of about 8 to about 18. Preferably, detergents incorporated into the particulate compositions have HLB values of about 10 to about 16, more preferably about 11 to about 15 (e.g., polyethylene glycol sorbitan monooleate, HLB=15.4; polyoxyethylene(10) isooctylphenyl ether, HLB=13.5; polyoxyethylene(20) sorbitan trioleate HLB=11).

In certain embodiments, the CIS compositions may also include one or more fatty acids, or a salt thereof, as an additional component. In those embodiments employing a fatty acid as the stabilizing agent component and a fatty acid as an additional component of the composition, the fatty acid utilized as the stabilizing agent will be different than the fatty acid used as the 'additional' component. Fatty acids useful in the CIS compositions of the invention may range in size from four to 30 carbon atoms, and may be unsaturated (e.g., stearic acid), monounsaturated (e.g., oleic acid), or polyunsaturated (e.g., linoleic acid), although monounsaturated and polyunsaturated fatty acids are generally preferred.

In some embodiments, the CIS compositions will incorporate a fatty acid having a carbon chain length of at least about 4, 5, 6, 8, 10, 15, 18, or 20 carbon atoms and less than about 30, 25, 20, 19, 15 or 10 carbon atoms. Accordingly, in some embodiments, the fatty acids utilized in the invention may have carbon chains with a length in the range of about 4 to 30, 5 to 25, 10 to 20, or 15 to 20 carbon atoms.

Fatty acids useful in the CIS compositions include, but are not limited to, arachidonic acid, decanoic acid, docosanoic acid, docosahexanoic acid eicosanoic acid, heneicosanoic acid, heptadecanoic acid, heptanoic acid, hexanoic acid, lauric acid, linoleic acid, linolenic acid, myristic acid, nonadecanoic acid, nonanoic acid, octanoic acid, oleic acid, palmitic acid, pentadecanoic acid, stearic acid, tetracosanoic acid, tricosanoic acid, tridecanoic acid, and undecanoic acid. Preferred fatty acids for use in the CIS compositions include oleic acid palmitoleic acid, and linoleic acid.

In certain embodiments of the invention, an antigen is incorporated into the CIS composition or administered in combination with a CIS composition. Those CIS compositions incorporating an antigen may incorporate the antigen into the particulate composition itself, or be dissolved or suspended in the solution in which the particulate composition is suspended. Any antigen may be incorporated into or co-administered with a CIS composition of the invention.

Delivery of ISS

In one embodiment, the ISS is delivered by itself into the individual. In another embodiment, the ISS is delivered with one or more antigens. In one embodiment, the antigen is co-administered with the ISS as a conjugate. In another embodiment, the antigen is administered with the ISS in a separate vehicle. The administration of the antigen can be contemporaneous or simultaneous with the ISS. Discussion of delivery of ISS infra also contemplates delivery of the antigen with the ISS.

ISS may be incorporated into a delivery vector, such as a plasmid, cosmid, virus or retrovirus, which may in turn code for therapeutically beneficial polypeptides, such as cytokines, hormones and antigens. Incorporation of ISS into such a vector does not adversely affect their activity.

A colloidal dispersion system may be used for targeted delivery of the ISS to an inflamed tissue, such as nasal membranes. Colloidal dispersion systems include macromolecule complexes, nanocapsules, microspheres, beads, and lipid-based systems including oil-in-water emulsions, micelles, mixed micelles, and liposomes. In one embodiment, the colloidal system of this invention is a liposome.

Liposomes are artificial membrane vesicles which are useful as delivery vehicles in vitro and in vivo. It has been shown that large unilamellar vesicles (LUV), which range in size from 0.2-4.0, um can encapsulate a substantial percentage of an aqueous buffer containing large macromolecules. RNA, DNA and intact virions can be encapsulated within the aqueous interior and be delivered to cells in a biologically active form (Fraley, et al, *Trends Biochem. Sci.,* 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes encoding the antisense polynucleotides at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., *Biotechniques,* 6:682, 1988).

The composition of the liposome is usually a combination of phospholipids, particularly high-phase transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14-18 carbon atoms, particularly from 16-18 carbon atoms, and is saturated. Illustrative phospholipids include egg phosphatidylcholine, dipalmitoylphosphatidylcholine and distearoylphosphatidylcholine.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various well known linking groups can be used for joining the lipid chains to the targeting ligand (see, e.g., Yanagawa, et al., *Nuc. Acids Symp. Ser.,* 19:189 (1988); Grabarek, et al., *Anal. Biochem.,* 185:131 (1990); Staros, et al., *Anal. Biochem.,* 156:220 (1986) and Boujrad, et al., *Proc. Natl. Acad. Sci. USA,* 90:5728 (1993). Targeted delivery of ISS can also be achieved by conjugation of the ISS to a the surface of viral and non-viral recombinant expression vectors, to an antigen or other ligand, to a monoclonal antibody or to any molecule which has the desired binding specificity.

Those of ordinary skill in the art will also be familiar with, or can readily determine, methods useful in preparing oligonucleotide-peptide conjugates. Conjugation can be accomplished at either termini of the ISS or at a suitably modified base in an internal position (e.g., a cytosine or uracil). For reference, methods for conjugating oligonucleotides to proteins and to oligosaccharide moieties of Ig are known (see, e.g., O'Shannessy, et al., *J. Applied Biochem.,* 7:347 (1985). Another useful reference is Kessler: "Nonradioactive Labeling Methods for Nucleic Acids", in Kricka (ed.), Nonisotopic DNA Probe Techniques (Acad. Press, 1992)).

Co-administration of a peptide drug with an ISS according to the invention may also be achieved by incorporating the ISS in cis or in trans into a recombinant expression vector (plasmid, cosmid, virus or retrovirus) which codes for any therapeutically beneficial protein deliverable by a recombinant expression vector. If incorporation of an ISS into an expression vector for use in practicing the invention is desired, such incorporation may be accomplished using conventional techniques which do not require detailed explanation to one of ordinary skill in the art. For review, however, those of ordinary skill may wish to consult Ausubel, *Current Protocols in Molecular Biology*, supra.

Briefly, construction of recombinant expression vectors (including those which do not code for any protein and are used as carriers for ISS) employs standard ligation techniques. For analysis to confirm correct sequences in vectors constructed, the ligation mixtures may be used to transform a individual cell and successful transformants selected by antibiotic resistance where appropriate. Vectors from the transformants are prepared, analyzed by restriction and/or sequenced by, for example, the method of Messing, et al., (*Nucleic Acids Res.,* 9:309, 1981), the method of Maxam, et al., (*Methods in Enzymology,* 65:499, 1980), or other suitable methods which will be known to those skilled in the art. Size separation of cleaved fragments is performed using conventional gel electrophoresis as described, for example, by Maniatis, et al., (*Molecular Cloning*, pp. 133-134, 1982).

Individual cells may be transformed with expression vectors and cultured in conventional nutrient media modified as is appropriate for inducing promoters, selecting transformants or amplifying genes. The culture conditions, such as temperature, pH and the like, are those previously used with the individual cell selected for expression, and will be apparent to the ordinarily skilled artisan.

If a recombinant expression vector is utilized as a carrier for the ISS of the invention, plasmids and cosmids are particularly preferred for their lack of pathogenicity. However, plasmids and cosmids are subject to degradation in vivo more quickly than viruses and therefore may not deliver an adequate dosage of ISS to substantially inhibit ISS immunostimulatory activity exerted by a systemically administered gene therapy vector. Of the viral vector alternatives, adenoassociated viruses would possess the advantage of low pathogenicity. The relatively low capacity of adeno-associated viruses for insertion of foreign genes would pose no problem in this context due to the relatively small size in which ISS of the invention can be synthesized.

Other viral vectors that can be utilized in the invention include adenovirus, adeno-associated virus, herpes virus, vaccinia or an RNA virus such as a retrovirus. Retroviral vectors are preferably derivatives of a marine, avian or human HIV retrovirus. Examples of retroviral vectors in which a single foreign gene can be inserted include, but are not limited to: Moloney marine leukemia virus (MoMuLV), Harvey marine sarcoma virus (HaMuSV), marine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence that enables the packaging mechanism to recognize an RNA transcript for encapsidation. Helper cell lines that have deletions of the packaging signal include, but are not limited to, T2, PA317 and PA 12, for example. These cell lines produce empty virions, since no genome is packaged. If a retroviral vector is introduced into such helper cells in which the packaging signal is intact, but the structural genes are replaced by other genes of interest, the vector can be packaged and vector virion can be produced. By inserting one or more sequences of interest into the viral vector, along with another gene which encodes the ligand for a receptor on a specific target cell, for example, the vector can be rendered target specific. Retroviral vectors can be made target specific by inserting, for example, a polynucleotide encoding a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome to allow target specific delivery of the retroviral vector containing ISS.

Pharmaceutical Compositions of ISS

If the ISS is to be delivered without use of a vector or other delivery system, the ISS will be prepared in a pharmaceutically acceptable composition. Pharmaceutically acceptable carriers preferred for use with the ISS of the invention may include sterile aqueous of non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like. A composition of ISS may also be lyophilized using means well known in the art, for subsequent reconstitution and use according to the invention.

Absorption promoters, detergents and chemical irritants (e.g., keritinolytic agents) can enhance transmission of an ISS composition into a target tissue. For reference concerning general principles regarding absorption promoters and detergents which have been used with success in mucosal delivery of organic and peptide-based drugs, see Chien, Novel Drug Delivery Systems, Ch. 4 (Marcel Dekker, 1992).

Examples of suitable nasal absorption promoters in particular are set forth at Chien, supra at Ch. 5, Tables 2 and 3; milder agents are preferred. Suitable agents for use in the method of this invention for mucosal/nasal delivery are also described in Chang, et al., Nasal Drug Delivery, "Treatise on Controlled Drug Delivery", Ch. 9 and Table 3-4B thereof, (Marcel Dekker, 1992). Suitable agents which are known to enhance absorption of drugs through skin are described in Sloan, Use of Solubility Parameters from-Regular Solution Theory to Describe Partitioning-Driven Processes, Ch. 5, "Prodrugs: Topical and Ocular Drug Delivery" (Marcel Dekker, 1992), and at places elsewhere in the text.

Methods and Routes for Administration of ISS to an Individual

The ISS of the invention are administered to an individual using any available method and route suitable for drug delivery. In one embodiment, the ISS, with or without antigen, is delivered to the upper and/or lower respiratory tract by any delivery means known to one of skill in the art. One preferred method of delivery of ISS is intranasal delivery, as described in the Examples. Another preferred method of ISS delivery is by insufflation. Other methods of administration include ex vivo methods (e.g., delivery of cells incubated or transfected with an ISS) as well as systemic or localized routes. One of ordinary skill in the art will appreciate that methods and routes of delivery which direct the ISS into the individual should avoid degradation of the ISS in vivo.

In one aspect, the invention provides for methods of administering the ISS along with an antigen that is present naturally in the environment (i.e., an "adventitious" antigen). Adventitious allergens can be allergens that fluctuate in levels throughout the seasons. The presence of seasonal allergens may be ascertained by using various sources, for example, weather reports from weather services, news reports broadcasted by television, radio or newspaper, institutional records, and private research. An example of an adventitious antigen is ragweed, e.g., ragweed pollen allergen Antigen E (Amb a I). Other non-limiting examples of adventitious antigens are grass allergen Lol p 1 (Tamborini et al. (1997) *Eur. J. Biochem.* 249:886-894), major dust mite allergens Der pI and Der PII (Chua et al. (1988) *J. Exp. Med.* 167:175-182; Chua et al. (1990) *Int. Arch. Allergy Appl. Immunol.* 91:124-129), domestic cat allergen Fel d I (Rogers et al. (1993) *Mol. Immunol.* 30:559-568), white birch pollen Bet v1 (Breiteneder et al. (1989) *EMBO J.* 8:1935-1938), Japanese cedar allergens Cry j 1 and Cry j 2 (Kingetsu et al. (2000) *Immunology* 99:625-629), and protein antigens from other tree pollen (Elsayed et al. (1991) *Scand. J. Clin. Lab. Invest. Suppl.* 204:17-31). As indicated, allergens from trees are known, including allergens from birch, juniper and Japanese cedar. Preparation of protein antigens from grass pollen for in vivo administration has been reported. Other antigens that may be used are described above in Table 1.

The entrance point for many exogenous antigens into an individual is through the skin or mucosa. Thus, delivery methods and routes which target the skin (e.g., for cutaneous and subcutaneous conditions) or mucosa (e.g., for respiratory, ocular, lingual or genital conditions) will be especially useful. Those of ordinary skill in the clinical arts will be familiar with, or can readily ascertain, means for drug delivery into skin and mucosa. For review, however, exemplary methods and routes of drug delivery useful in the invention are briefly discussed below.

Intranasal administration means are particularly useful in addressing respiratory problems such as asthma (e.g., allergic asthma), respiratory inflammation, particularly inflammation mediated by antigens transmitted from the nasal passages into the trachea or bronchioli. Such means include inhalation of aerosol suspensions of the polynucleotide compositions of the invention. Nebulizer devices suitable for delivery of polynucleotide compositions to the nasal mucosa, trachea and bronchioli are well-known in the art and will therefore not be described in detail here. For general review in regard to intranasal drug delivery, those of ordinary skill in the art may wish to consult Chien, Novel Drug Delivery Systems, Ch. 5 (Marcel Dekker, 1992).

Dermal routes of administration, as well as subcutaneous injections, are useful in addressing allergic reactions and inflammation in the skin. Examples of means for delivering drugs to the skin are topical application of a suitable pharmaceutical preparation, transdermal transmission, injection and epidermal administration.

For transdermal transmission, absorption promoters or iontophoresis are suitable methods. For review regarding such methods, those of ordinary skill in the art may wish to consult Chien, supra at Ch. 7. Iontophoretic transmission may be accomplished using commercially available "patches" which deliver their product continuously via electric pulses through unbroken skin for periods of several days or more. Use of this method allows for controlled transmission of pharmaceutical compositions in relatively great concentrations, permits infusion of combination drugs and allows for contemporaneous use of an absorption promoter.

An exemplary patch product for use in this method is the LECTRO PATCH trademarked product of General Medical Company of Los Angeles, Calif. This product electronically maintains reservoir electrodes at neutral pH and can be adapted to provide dosages of differing concentrations, to dose continuously and/or to dose periodically. Preparation and use of the patch should be performed according to the manufacturer's printed instructions which accompany the LECTRO PATCH product; those instructions are incorporated herein by this reference.

Epidermal administration essentially involves mechanically or chemically irritating the outermost layer of the epidermis sufficiently to provoke an immune response to the irritant. An exemplary device for use in epidermal administration employs a multiplicity of very narrow diameter, short tynes which can be used to scratch ISS coated onto the tynes into the skin. The device included in the MONO-VACC old tuberculin test manufactured by Pasteur Merieux of Lyon, France is suitable for use in epidermal administration of ISS. Use of the device is according to the manufacturer's written instructions included with the device product; these instructions regarding use and administration are incorporated herein by this reference to illustrate conventional use of the device. Similar devices which may also be used in this embodiment are those which are currently used to perform allergy tests.

Systemic administration involves invasive or systemically absorbed topical administration of pharmaceutical preparations. Topical applications as well as intravenous and intramuscular injections are examples of common means for systemic administration of drugs.

Dosing Parameters for ISS

A particular advantage of the ISS of the invention is their capacity to exert anti-inflammatory and/or immunotherapeutic activity even at low dosages. Although the dosage used will vary depending on the clinical goals to be achieved, a suitable dosage range is one which is an effective amount to obtain long term disease modification. In one embodiment, the long term disease embodiment is to reduce any one of the following symptoms of asthma: bronchial hyper responsiveness, eosinophil infiltration in the airways, mucus production in the airways, Th2 cytokines in the airways, airway remodeling, immediate asthmatic reaction (airway constriction immediately after allergen exposure), and late asthmatic reaction (airway constriction several hours after allergen exposure).

In one aspect, the ISS is administered in at least 3 weekly doses. The dosage of ISS to be administered is about 0.001 mg/kg to about 100 mg/kg. In one embodiment, the dosage to be administered is 0.005 mg/kg to about 50 mg/kg. In another embodiment, dosage of ISS to be administered is about 0.01 mg/kg to about 10 mg/kg. In another embodiment, at least 4, 5, 6, 7, 8, 9, 10, 11, or 12 doses of ISS are administered to the individual for achieving long term disease modification.

The ISS is administered multiple times over a period of time. The interval between administration of dosages may be once a week. In the alternative, a slightly shorter period of time between administration of dosages may be used, for example 3, 4, 5, or 6 days in between administration of dosages. In another alternative, a longer period of time may elapse in between administration of dosages, for example every 8, 9, 10, 11, 12, 13, or 14 days. In yet another alternative, the ISS may be administered in multiple dosages every 2.5 weeks, 3 weeks or 4 weeks. In one embodiment, the ISS is administered in at least 3 weekly doses at about 0.01 mg/kg to about 10 mg/kg per dose. In another embodiment, at least 4, 5, 6, 7, 8, 9, 10, 11, or 12 doses of ISS are administered to the individual for achieving long term effect.

In yet another aspect, the ISS is administered at dosage of about 0.01 mg/kg to about 10 mg/kg and at least 3 doses are administered to the individual with about 3, 4, 5, or 6 days in between the dosages for conferring long term disease modification. In another embodiment, the ISS is administered at dosage of about 0.01 mg/kg to about 10 mg/kg and at least 3 doses are administered to the individual with about 8, 9, 10, 11, 12, 13, or 14 days in between the dosages for conferring long term disease modification. In another embodiment, the ISS is administered at dosage of about 0.01 mg/kg to about 10 mg/kg and at least 3 doses are administered to the individual with about 2.5 weeks, 3 weeks or 4 weeks in between the dosages for conferring long term disease modification. In one embodiment, at least 4, 5, 6, 7, 8, 9, 10, 11, or 12 doses of ISS are administered to the individual at intervals ranging from about 3 to about 14 days in between dosages for achieving long term effect. In another embodiment, at least 4, 5, 6, 7, 8, 9, 10, 11, or 12 doses of ISS are administered to the individual at intervals ranging from about 2.5 weeks, 3 weeks or 4 weeks in between the dosages for achieving long term effect. In another embodiment, these doses of ISS are administered approximately once a week. One of skill in the art will be able to adjust the range of dosing accordingly by measuring the levels of Th2 cytokines, as exemplified in the Examples. In view of the teaching provided by this disclosure and what is generally known at the time of filing, those of ordinary skill in the clinical arts will be familiar with, or can readily ascertain, suitable parameters for administration of ISS according to the invention.

In this respect, it should be noted that the anti-inflammatory and immunotherapeutic activity of ISS in the invention is essentially dose-dependent. Therefore, to increase ISS potency by a magnitude of two, each single dose should be doubled in concentration. Clinically, it may be advisable to administer the ISS in a low dosage (e.g., about 0.01 mg/kg), then increase the dosage as needed to achieve the desired therapeutic goal. Based on current studies, ISS are believed to have little or no toxicity at these dosage levels.

Kits for Use in Practicing the Methods of the Invention

For use in the methods described above, kits are also provided by the invention. Such kits may include any or all of the following: ISS (conjugated or unconjugated); a pharmaceutically acceptable carrier (may be pre-mixed with the ISS) or suspension base for reconstituting lyophilized ISS; additional medicaments; a sterile vial for each ISS and additional medicament, or a single vial for mixtures thereof, devices) for use in delivering ISS to a individual; assay reagents for detecting indicia that the immunomodulatory effects sought have been achieved in treated individuals, instructions for how to and when administer the ISS and a suitable assay device.

Examples illustrating the practice of the invention are set forth below. The examples are for purposes of reference only and should not be construed to limit the invention.

EXAMPLES

Example 1 Inhibition of Th2-Type Gene Induction after Intranasal Treatment with 1018 ISS in a Mouse Model for Ragweed-Induced Allergic Asthma One purpose of this experiment was to investigate the duration of the effect of intranasal 1018 ISS treatment on the inhibition of allergen-induced Th2-gene induction in ragweed-sensitized and challenged mice. The genes evaluated included various Th2-cytokines, chemokines, and various other molecules involved in airway inflammation. Female BALB/c mice were intraperitoneally sensitized with ragweed on Alum on day −21 and day −14. At various time points (ranging from day −7 to day 0 plus 3 hrs), groups of mice were intranasally treated with 1018 ISS or saline under light anesthesia. On day 0, all groups were challenged intranasally with either ragweed or saline. Six hrs after challenge, lungs were harvested and snap-frozen in liquid nitrogen. Total RNA was isolated and converted into cDNA. Expression of mRNA was measured in the lung cDNA samples using real-time quantitative PCR.

The materials used were: 1018 (lot number AGU-003, Dynavax), Ragweed (Pollen lot #16, 24QQ 56-9FD-3, extract 17 Jan. 2003, Dynavax), pyrogenic-free saline (Sigma). The methods used were as follows: The study was performed with 6-8 week old female BALB/c mice from Charles River (Hollister, Calif.). A total of 90 mice were intraperitoneally sensitized with 10 µg of ragweed on Alum on day −21 and day −14. Starting from day −7 onwards groups of 5 mice were treated intranasally with pyrogenic-free saline (50 µl) or with 1018 ISS (20 µg/50 µl saline) under light isofloraine anesthesia according to the schedule below.

| sensitization | day of treatment | treatment | challenge |
| --- | --- | --- | --- |
| ragweed | −7 | saline | saline |
| ragweed | −7 | saline | ragweed |
| ragweed | −7 | 1018 ISS | ragweed |
| ragweed | −5 | saline | saline |
| ragweed | −5 | saline | ragweed |
| ragweed | −5 | 1018 ISS | ragweed |
| ragweed | −3 | saline | saline |
| ragweed | −3 | saline | ragweed |
| ragweed | −3 | 1018 ISS | ragweed |
| ragweed | −1 | saline | saline |
| ragweed | −1 | saline | ragweed |
| ragweed | −1 | 1018 ISS | ragweed |
| ragweed | 0 | saline | saline |
| ragweed | 0 | saline | ragweed |
| ragweed | 0 | 1018 ISS | ragweed |
| ragweed | 0 plus 3 hrs | saline | saline |
| ragweed | 0 plus 3 hrs | saline | ragweed |
| ragweed | 0 plus 3 hrs | 1018 ISS | ragweed |

On day 0, all mice were challenged intranasally with either ragweed (5 µg/50 µl saline) or saline (50 µl). Six hrs after challenge, lungs were harvested, snap-frozen in liquid nitrogen, and stored at −80° C. for later use. Total RNA was isolated using RNeasy mini kits (Qiagen Inc., Valencia, Calif.). The RNA samples were DNAse-treated (Roche Diagnostics, Mannheim, Germany) and converted into cDNA using Superscript II Rnase H-Reverse Transcriptase (Invitrogen, Rockville, Md.) according to previously published methods (Scheerens et al., Eur. J. of Immunology 2001, 31:1465-74).

In each cDNA sample, mRNA expression levels of a variety of genes were measured using real-time quantitative PCR (ABI Prism 5700, Perkin Elmer Applied Biosystems) and SYBR green (Qiagen Inc., Valencia, Calif.). Sense and anti-sense primers used for detection were developed in house and included primer sets to Th2-cytokines, chemokines, and various other molecules involved in airway inflammation. In addition to the gene of interest, in each sample the mRNA expression of a house keeping gene was measured (in this case ubiquitin). After correcting for the amount of RNA per sample, all data were calculated relative to the expression of the house keeping gene (represented as gene/ubiquitin ratio).

Results: In FIG. 1, six genes essential for the development of a Th2-type airway inflammatory response are depicted and data are expressed as gene/ubiquitin ratio. The data demonstrate that intranasal challenge with ragweed in sensitized mice upregulated mRNA expression levels of Th2-genes such as IL-4, IL-5, and IL-13 when compared to saline-challenged mice (ragweed-challenged mice denoted as RW/RW/Saline in grey bars, saline-challenged mice denoted as RW/Saline/Saline in open bars). In addition, mRNA expression levels of the chemokines TARC, MDC and eotaxin were upregulated after allergen challenge in the RW/RW/Saline mice. In contrast, in mice pretreated with 1018 ISS (denoted as RW/RW/1018 in black bars), the ragweed-induced upregulation of the various cytokines and chemokines expression levels was inhibited, however, only when 1018 ISS pretreatment was given on day −1 or on day −3, or for some genes on day −5.

Figure 2:
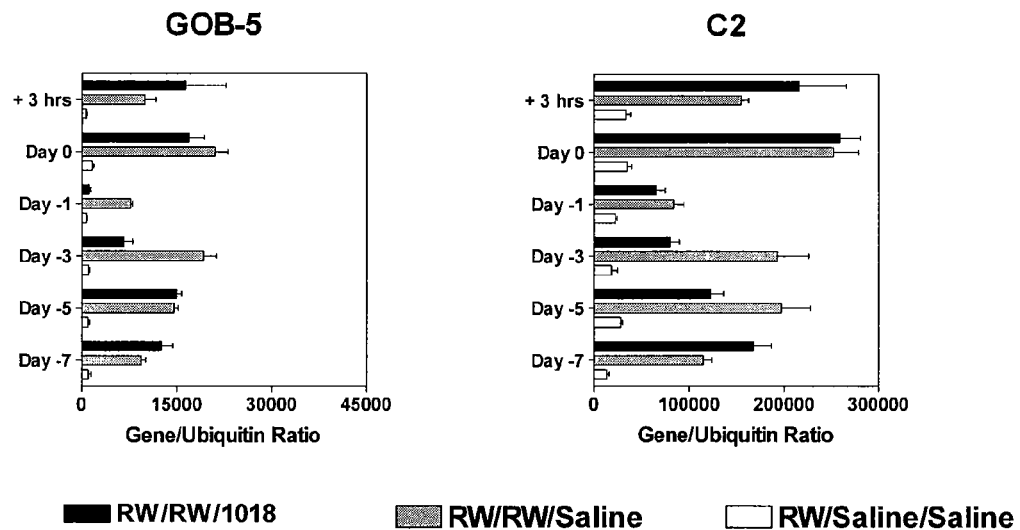
FIG. 2 is a graph that depicts inhibition of Th2 gene induction for GOB-5 and C2 by pretreatment with 1018 ISS. The data are expressed as gene/ubiquitin ratio.

In FIG. 2, gene/ubiquitin ratios are shown for GOB-5 and C2. GOB-5 and C2 (also known as FIZZ-1) are both genes that are known to be induced in the airways by IL-4. It is clear from our data that challenge with ragweed led to upregulation of both genes. In contrast, pretreatment with 1018 ISS given a few days before the challenge with ragweed inhibited the expression of these mRNAs associated with a Th2-type airway inflammation. For GOB-5, 1018 ISS treatment is effective when given on day −1 or day −3. For C2, 1018 ISS treatment is effective when given on day −3 or day −5.

It has been published that pretreatment with ISS inhibits allergen-induced airway eosinophilia and airway hyperresponsiveness in a mouse model for allergic asthma (Broide et al., J. Immunol., 161:7054, 1998). We have shown that this inhibition correlates with ISS-induced down-regulation of Th2 and Th2-dependent gene expression levels in the airways (Hessel et al. (2005) J. Exp. Med., 202(11):1563.

Here, we determined the duration of ISS-mediated inhibition of the allergen-induced Th2 response in the airways. As a way to establish this window of effectiveness, we measured the expression of a series of genes in the airways that are essential in or closely related to the development of Th2-type airway inflammation after allergen challenge in sensitized mice. Our data demonstrate that 1018 ISS given between one to three days before the allergen challenge is able to inhibit the majority of these genes, which results in a greatly diminished Th2 response in the airways. If 1018 ISS is given further removed from the allergen challenge (i.e., earlier than day −3), we found that 1018 ISS is not able to down-regulate Th2 or Th2-dependent gene expression.

Thus, if one seeks to study the direct effects of ISS treatment on the airway Th2 response, it is advisable to pretreat within one to three days before the allergen challenge, whereas if one is interested in studying the long-term effects of ISS on disease modification, it is advisable to wait at least a week after ISS treatment to ensure the absence of direct ISS effects.

Example 2 The Effects of Long-Term Intranasal Treatment with 1018 ISS in a Mouse Model for Ragweed-Induced Allergic Asthma One purpose of this set of experiments is to investigate whether long-term intranasal treatment with 1018 ISS leads to disease modification in a mouse model for ragweed-induced allergic asthma. The long-term effects of weekly intranasal treatment with 1018 ISS in ragweed-sensitized and challenged mice were investigated.

Mice were sensitized and subsequently challenged with an intranasal low dose of ragweed on a weekly basis. Also on a weekly basis the mice were treated intranasally with either saline or 1018 ISS. At several time points during the course of the experiment, mice were set aside to rest for a period of 2 weeks. This rest period was to ensure that the direct effects of 1018 ISS treatment had waned. At the end of the 2 weeks, these mice were re-challenged with a high dose of ragweed and the response to this allergen challenge was evaluated by ways of measuring the amount of Th2 and Th1 cytokines in the airways and by determining the amount of airway eosinophil infiltration.

More specifically, the materials used were: 1018 (lot number AGU-003, Dynavax); Ragweed (Pollen lot #16, 24QQ 56-9FD-3, extract 17 Jan. 2003, Dynavax); pyrogenic-free saline (Sigma). The methods used were as follows: The study was performed with 6-8 week old female BALB/c mice from Charles River (Hollister, Calif.). The mice were intraperitoneally sensitized with 15 µg of ragweed on Alum on day 0 and day 7. Starting from day 14 onwards, mice were challenged intranasally on a weekly basis with 0.5 µg ragweed or pyrogenic-free saline (50 µl) under light isofloraine anesthesia. Simultaneously, the mice were treated weekly with 1018 ISS (20 µg/50 µl saline) or pyrogenic-free saline (50 µl) via the intranasal route. After 1, 2, 6, and after 10 weeks of antigen challenge and ISS treatment, mice were set aside for a rest period of 2 weeks and subsequently re-challenged intranasally with 5 µg of ragweed. Twenty-four hrs later lungs were lavaged and cytokines were measured in the lavage fluid by ELISA. The detection levels for the IL-4, IL-13, IL-10, and IFN-γ ELISA were respectively 8, 8, 8, and 23 pg/ml. Lavage fluid was spun down and the cells recovered were counted using trypan blue. The remaining cells were used to prepare a cytospin and stained with Wright-Giemsa staining. Differential cell counts were performed and the number of eosinophils was determined for each cytospin.

Figure 5:
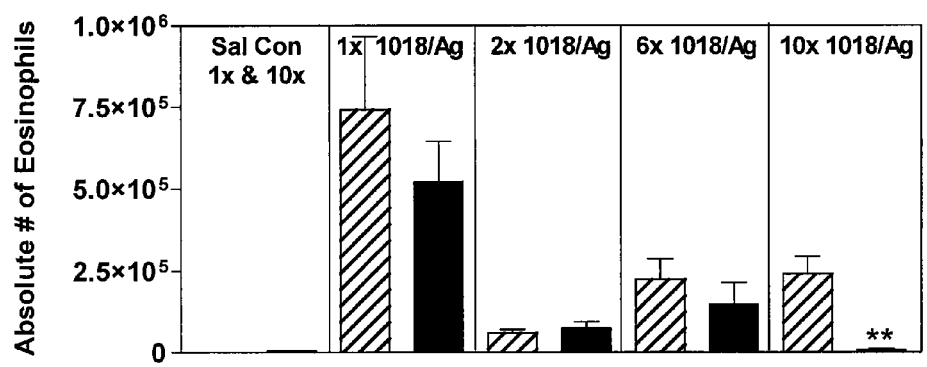
FIG. 5 is a graph that depicts absolute number of eosinophils detected in BAL fluid. The double asterisks indicate a statistical significance of $p<0.01$.

In FIGS. 3 and 4, levels of the Th2-type cytokines IL-4, IL-13 and IL-10 measured in lavage fluid (BAL fluid) are depicted in pg/ml. In addition, in FIG. 4 the Th1-type cytokine IFN-γ is shown. The results indicate that weekly challenges with ragweed in sensitized mice led to a robust Th2 inflammation in the airways with high levels of IL-4, IL-13, and IL-10, as well as a high number of eosinophils (shown in FIG. 5). These high levels of Th2 cytokines and eosinophils were absent when ragweed-sensitized mice were challenged with saline only. When mice were challenged with ragweed and simultaneously treated with 1018 ISS, no significant differences were observed after 1, 2, or 6 weeks of ISS treatment when comparing ragweed-challenged mice treated with saline or with ISS. However, after 10 weeks of 1018 ISS treatment, the Th2 cytokine levels as well as the number of eosinophils were significantly diminished (IL-13: * p<0.05; IL-4, IL-10, and eosinophils: ** p<0.01), indicating that the Th2 inflammation was inhibited in those mice. Furthermore, these data show that no increased levels of IFN-γ were induced in the mice treated with 1018 ISS at any of the time points measured, indicating that 10 weekly treatments with 1018 ISS did not induce an overt Th1-type response in the airways.

Our experimental data described in this experiment demonstrated that ISS treatments did lead to disease modification, i.e. inhibition of the Th2 response to allergen, however, this was in our hands not accompanied by the development of an overt Th1 response in the airways. In Example 1, we determined that the direct effects of 1018 ISS on the Th2 response in the airways lasted less than a week. Therefore, in this Example, all mice were rested for at least 2 weeks after their last ISS treatment, before being re-challenged with allergen. Thus any effects seen could not be attributed direct effects of ISS treatment. The response to the re-challenge with allergen was to determine whether the airways would still develop a Th2 inflammation in response to the allergen challenge or whether they had become refractory to allergen challenge. Our data showed that at least 10 weekly intranasal 1018 ISS treatments was needed to achieve this disease modifying effect.

Example 3 The Effects of Long-Term Intranasal Treatment with 1018 ISS in a Mouse Model for Ragweed-Induced Allergic Asthma This set of experiments was conducted to investigate whether long-term intranasal treatment with 1018 ISS conferred disease modification in a mouse model for ragweed-induced allergic asthma and to evaluate whether this disease modification persists after 1018 ISS treatment is stopped but allergen exposure is continued.

Mice were sensitized and subsequently challenged with an intranasal low dose of ragweed on a weekly basis. Also on a weekly basis the mice were treated intranasally with either saline or 1018 ISS. At several time points during the course of the experiment, mice were set aside to rest for a period of 2 weeks. This rest period was to ensure that the direct effects of 1018 ISS treatment had waned. At the end of the 2 weeks, these mice were re-challenged with a high dose of ragweed and the response to this allergen challenge was evaluated by ways of measuring the amount of Th2 and Th1 cytokines in the airways. The experimental groups included in this study were as follows:

| sensitization | weekly allergen | weekly treatment |
| --- | --- | --- |
| ragweed day 0 and 7 | ragweed wk 1-25 | saline week 1-25 |
| ragweed day 0 and 7 | ragweed wk 1-25 | 1018 ISS week 1-25 |
| ragweed day 0 and 7 | ragweed wk 1-25 | 1018 ISS week 1-12 |
| ragweed day 0 and 7 | ragweed wk 1-12 | 1018 ISS week 1-12 |

The purpose of the mice receiving ISS treatment for 12 weeks and allergen challenges for a total of 25 weeks was to evaluate whether ISS-induced disease modification was long-lasting in the presence of continued allergen exposure.

More specifically, the materials used were: 1018 (lot number AGU-003, Dynavax); Ragweed (Pollen lot # Jan. 26, 2005, Dynavax); pyrogenic-free saline (Sigma). The study was performed with 6-8 week old female BALB/c mice from Charles River (Hollister, Calif.). The mice were intraperitoneally sensitized with 15 µg of ragweed on Alum on day 0 and day 7. Starting from day 14 onwards, mice were challenged intranasally on a weekly basis with 0.5 µg ragweed or pyrogenic-free saline (50 µl) under light isofloraine anesthesia. Simultaneously, the mice were treated weekly with 1018 ISS (20 µg/50 µl saline) or TOLAMBA (20 µg/50 µl saline) or pyrogenic-free saline (50 µl) via the intranasal route. After 1, 8, 12, 16, and after 25 weeks of antigen challenges and ISS treatment, mice were set aside for a rest period of 2 weeks and subsequently re-challenged intranasally with 5 µg of ragweed. Twenty-four hours later lungs were lavaged and cytokines were measured in the lavage fluid by ELISA.

Figure 6:
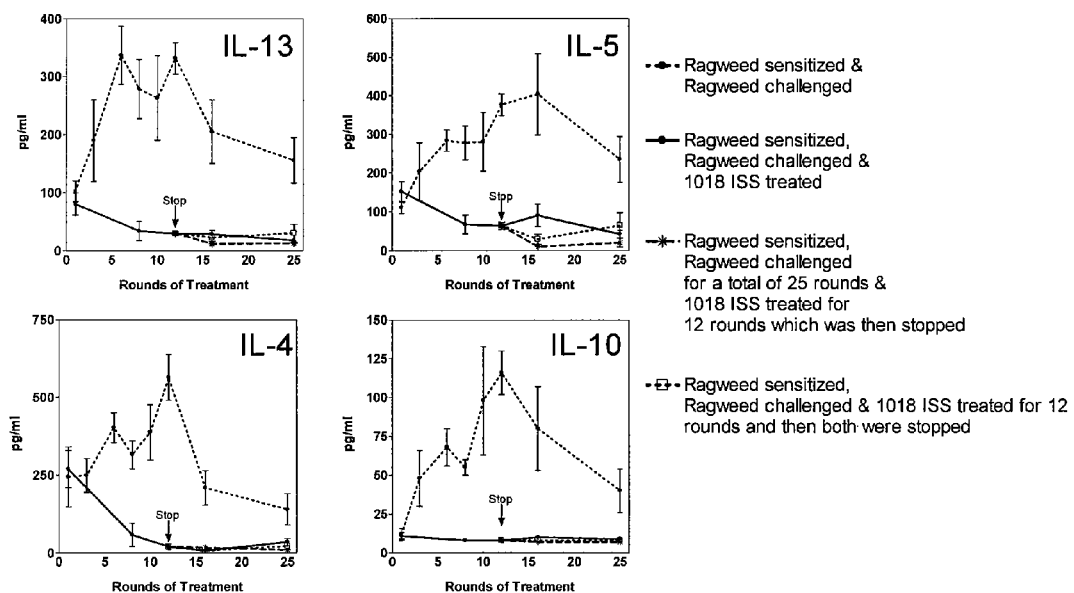
FIG. 6 is a graph that depicts levels of the Th2-type cytokines IL-4, IL-5, IL-10 and IL-13 measured in lavage fluid (BAL fluid) in mice that have been treated with multiple administrations of 1018 ISS.

Results: In FIG. 6, levels of the Th2-type cytokines IL-4, IL-5, IL-13 and IL-10 measured in lavage fluid (BAL fluid) are depicted in pg/ml. The detection levels for the IL-4, IL-5, IL-13, IL-10, and IFN-γ ELISA were respectively 8, 8, 8, 8, and 23 pg/ml. In addition, the Th1-type cytokine IFN-γ was measured but no induction of IFN-γ above detection level was measured in any of the treatment groups. Our results show that weekly challenges with ragweed in sensitized mice led to a robust Th2 inflammation in the airways with high levels of IL-4, IL-5, IL-13, and IL-10. When mice were challenged with ragweed and simultaneously treated with 1018 ISS, no significant differences were observed after 1 week of ISS treatment when comparing ragweed-challenged mice treated with saline or with ISS. However, after 8, 12, 16, and 25 weeks of 1018 ISS treatment, the Th2 cytokine levels were significantly diminished, indicating that the allergen-induced Th2 inflammation was inhibited in the 1018 ISS-treated mice. The observation that no detectable levels of IFN-γ were induced in the mice treated with 1018 ISS at any of the time points measured indicates that 25 weekly treatments with 1018 ISS did not induce an overt Th1-type response in the airways. In groups treated for 12 weeks with 1018 ISS that subsequently continued to receive allergen challenges for another 13 weeks, the Th2 response remained inhibited, indicating that the disease modification induced by 1018 ISS is long-lasting.

In Example 2, we demonstrated that 10 weekly ISS treatments led to disease modification, i.e., inhibition of the Th2 response to allergen, however, this was not accompanied by the development of an overt Th1 response in the airways. The experiment described here extends this finding with the observation that disease modification is in fact already achieved after 8 weekly 1018 ISS treatments and that this disease modification persists even when allergen exposures continued for another 13 weeks.

Example 4 ISS-Conjugates

Figure 7:
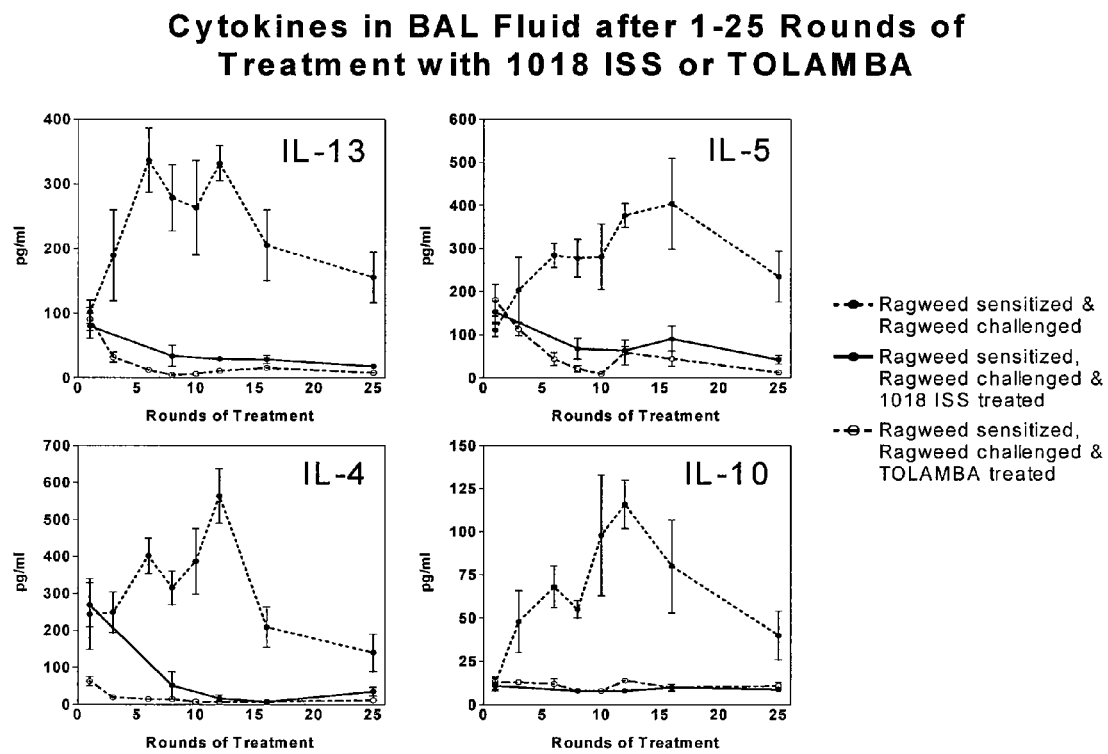
FIG. 7 is a graph that depicts levels of the Th2-type cytokines IL-4, IL-5, IL-10 and IL-13 measured in lavage fluid (BAL fluid) in mice that have been treated with multiple administrations of 1018 ISS or TOLAMBA.

Methods similar to Example 3 above were used except that both 1018 ISS and 1018 ISS conjugated to Amb a I (conjugate known as TOLAMBA) were used. FIG. 7 is a graph that depicts the results of measuring Th2-type cytokines, IL-4, IL-5, IL-10, and IL-13 in mice that have been treated with 20 µg of 1018 ISS via the intranasal route on a weekly basis for 25 weeks or 20 µg TOLAMBA via the intranasal route on a weekly basis for 25 weeks. Th2 suppression was also observed when using ISS-conjugate.

Example 5 The Effects of Long-Term Intranasal Treatment with 1018 ISS in a Mouse Model for Ragweed-Induced Allergic Asthma and the Role of IFN-γ

This experiment was conducted to investigate whether the maintenance of the disease modification induced by long-term intranasal treatment with 1018 ISS in a mouse model for ragweed-induced allergic asthma was mediated by the cytokine IFN-γ.

Mice were sensitized and subsequently challenged with an intranasal low dose of ragweed on a weekly basis. Also on a weekly basis the mice were treated intranasally with either saline or 1018 ISS. At several time points during the course of the experiment, mice were set aside to rest for a period of 2 weeks. This rest period was to ensure that the direct effects of 1018 ISS treatment had waned. At the end of the 2 weeks, these mice were re-challenged with a high dose of ragweed and the response to this allergen challenge was evaluated by ways of measuring the amount of Th2 and Th1 cytokines in the airways. The experimental groups included in this study were as follows:

| sensitization | weekly allergen | weekly treatment | antibody treatment |
|---|---|---|---|
| ragweed day 0 and 7 | saline wk 1-17 | saline week 1-17 | none |
| ragweed day 0 and 7 | ragweed 1-17 | saline week 1-17 | none |
| ragweed day 0 and 7 | ragweed 1-17 | 1018 ISS week 1-17 | none |
| ragweed day 0 and 7 | ragweed 1-17 | 1018 ISS week 1-13 | none |
| ragweed day 0 and 7 | ragweed 1-13 | 1018 ISS week 1-13 | none |
| ragweed day 0 and 7 | ragweed 1-17 | 1018 ISS week 1-13 | isotype (GL113) wk 13-17 |
| ragweed day 0 and 7 | ragweed 1-17 | 1018 ISS week 1-13 | anti-IFN-g (XMG1.2) wk 13-17 |

The purpose of the mice receiving ISS treatment for 13 weeks and allergen challenges for a total of 17 weeks was to evaluate whether ISS-induced disease modification was long-lasting in the presence of continued allergen exposure. The purpose of the groups receiving antibody treatment (either control or anti-IFN-γ antibodies) was to evaluate whether IFN-γ was necessary for the maintenance of the ISS-induced disease modification.

More specifically, the materials used were: 1018 ISS (lot number AGU-003, Dynavax); Ragweed (Pollen lot # Jan. 26, 2005, Dynavax); pyrogenic-free saline (Sigma). The study was performed with 6-8 week old female BALB/c mice from Charles River (Hollister, Calif.). The mice were intraperitoneally sensitized with 15 µg of ragweed on Alum on day 0 and day 7. Starting from day 14 onwards, mice were challenged intranasally on a weekly basis with 0.5 µg ragweed or pyrogenic-free saline (50 µl) under light isofloraine anesthesia. Simultaneously, the mice were treated weekly with 1018 ISS (20 µg/50 µl saline) or pyrogenic-free saline (50 µl) via the intranasal route. In some groups mice were intraperitoneally treated with isotype control antibodies (clone GL113) or with antibodies to IFN-γ (clone XMG1.2) (2 mg in 200 µl, once per week) during week 13-17. After 1, 3, 8, 13, and 17 weeks of antigen challenges and ISS treatment, mice were set aside for a rest period of 2 weeks and subsequently re-challenged intranasally with 5 µg of ragweed. Twenty-four hours later lungs were lavaged and cytokines were measured in the lavage fluid by ELISA.

Figure 8:
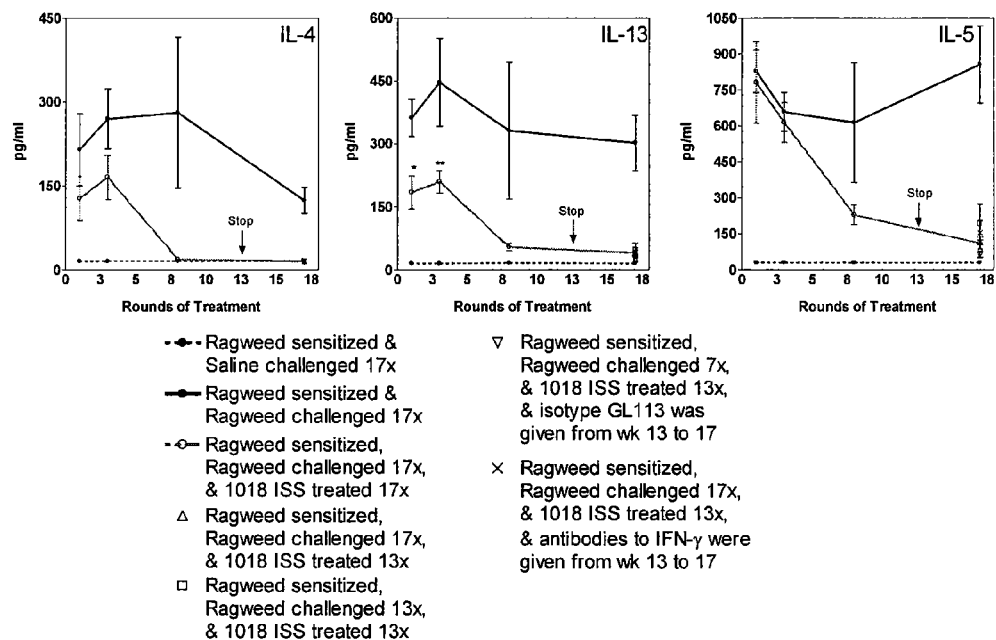
FIG. 8 is a graph that depicts the effects of long term intranasal treatment with 1018 ISS in a mouse model for ragweed-induced allergic asthma.

Results: In FIG. 8, levels of the Th2-type cytokines IL-4, IL-13 and IL-5 measured in lavage fluid (BAL fluid) are depicted in pg/ml. The detection levels for the IL-4, IL-113, IL-5, and IFN-γ ELISA were respectively 16, 16, 31, and 16 pg/ml. In addition, the Th1-type cytokine IFN-γ was measured but no induction of IFN-γ above detection level was measured in any of the treatment groups. Our results show that weekly challenges with ragweed in sensitized mice led to a robust Th2 inflammation in the airways with high levels of IL-4, IL-113, and IL-5. When mice were challenged with ragweed and simultaneously treated with 1018 ISS, no significant differences in IL-4 and IL-5 were observed after 1 or 3 weeks of ISS treatment when comparing ragweed-challenged mice treated with saline or with ISS. IL-13 levels were significantly inhibited in ISS-treated and ragweed-challenged mice after 1 or 3 weeks of ISS-treatment. After 8, 13, and 17 weeks of 1018 ISS treatment, however, all three Th2 cytokine levels were significantly diminished, indicating that the allergen-induced Th2 inflammation was inhibited in the 1018 ISS-treated mice. The observation that no detectable levels of IFN-γ were induced in the mice treated with 1018 ISS at any of the time points measured indicates that 17 weekly treatments with 1018 ISS did not induce an overt Th1-type response in the airways. In groups treated for 13 weeks with 1018 ISS that subsequently continued to receive allergen challenges for another 4 weeks, the Th2 response remained inhibited, indicating that the disease modification induced by 1018 ISS is long-lasting. In groups that were treated for 13 weeks with 1018 ISS, subsequently continued with allergen exposures and were treated with either control or anti-IFN-γ antibodies the Th2 response remained inhibited as well, indicating that IFN-γ is not necessary for the maintenance of disease modification.

In Example 2, we demonstrated that 10 weekly ISS treatments led to disease modification, i.e., inhibition of the Th2 response to allergen, however, this was not accompanied by the development of an overt Th1 response in the airways. In Example 3 we demonstrated that disease modification is already achieved after 8 weekly 1018 ISS treatments and that this disease modification persists even when allergen exposures continued for another 13 weeks. This experiment repeats the observation that disease modification is achieved after 8 weekly 1018 ISS treatments and extends it with the observation that IFN-γ is not needed for the maintenance of this disease modification.

What is claimed is:

1. A method for treating asthma in an individual in need thereof comprising administering to the individual multiple administrations of an effective amount of composition comprising a CpG-containing immunostimulatory sequence (ISS), wherein the ISS is unconjugated ISS and is greater than about 10 bases or base pairs and less than about 200 bases or base pairs, wherein the cytosine of CpG is unmethylated, and wherein the administration of the composition results in long term disease modification of asthma, wherein the long term disease modification is determined by the reduction of one or more asthma symptoms for a period of at least 3 weeks following administration of the last dose of ISS, and wherein the composition is administered at least 5 times.

2. The method of claim 1 wherein the multiple administrations occur on a weekly basis.

3. The method of claim 1 wherein the composition is administered at least 8 times.

4. The method of claim 1 wherein the multiple administration of the composition comprising ISS occurs every two weeks.

5. The method of claim 1 wherein the long term disease modification is a decrease of Th2 response in the individual.

6. The method of claim 5 wherein the decrease of Th2 response in the individual is a decrease of any one of the cytokines selected from the group consisting of IL-4, IL-5, IL-10, and IL-13.

7. The method of claim 1 wherein the long term disease modification lasts at least 13 weeks after the last administration of the ISS.

8. The method of claim 1 wherein the treatment results in long term disease modification of asthma wherein the asthma is allergic asthma.

9. The method of claim 1 wherein the ISS is selected from the group consisting of 1018 ISS, wherein 1018 ISS is (5'-TGACTGTGAACGTTCGAGATGA-3') (SEQ ID NO:1) and an ISS comprising (1) at least one palindromic sequence of at least 8 bases in length, wherein the palindromic sequence comprises at least one CG dinucleotide, and (2) at least one TCG trinucleotide sequence at or near the 5'end of the polynucleotide.

10. The method of claim 1 wherein the ISS is 1018 ISS, wherein 1018 ISS is (5'-TGACTGTGAACGTTCGAGATGA-3') (SEQ ID NO:1).

11. The method of claim 5 wherein the decrease of Th2 response in an individual is a decrease in eosinophil infiltration in the airways.

12. The method of claim 1 wherein the modification lasts at least 8 weeks after the last administration of the composition comprising ISS.

13. The method of claim 1 wherein the ISS is 5'-$N_x$(TCG $(N_q)_y N_w(X_1 X_2 CGX_2' X_1'(CG)_p)_z$ wherein N are nucleosides with x=0-3, y=1-4, w=−2, −1, 0, 1 or 2, p=0 or 1, q=0, 1 or 2, and z=1-20, wherein $X_1$ and $X_1'$, $X_2$ and $X_2'$ are self-complimentary, and wherein the 5' T of the $(TCG(N_q))_y$ sequence is 0-3 bases from the 5' end of the polynucleotide.

14. The method of claim 1 or 13 wherein the ISS comprises phosphorothioate linkages.

15. A method for treating asthma in an individual in need thereof comprising administering to the individual multiple administrations of an effective amount of composition comprising a chimeric immunomodulatory molecule (CIC), wherein the CIC is a linear CIC comprising a core structure of: $N_1$—$S_1$—$N_2$ or $N_1$—$S_1$—$N_2$—$S_2$—$N_3$, wherein $N_1$, $N_2$, and $N_3$ are nucleic acid moieties and $S_1$ and $S_2$ are non-nucleic acid spacer moieties, and $S_1$ and $S_2$ are covalently bound to two nucleic acid moieties, or wherein the CIC is a branched CIC comprising a core structure with the formula $[N_v]_A$—$S_p$ wherein (a) A is at least 3; (b) $S_p$ is a multivalent spacer moiety covalently bonded to A independently selected nucleic acid moieties ($N_v$); wherein at least one nucleic acid moiety of the CIC comprises at least one 5'-cytosine, guanine-3' (5'-CG-3') sequence, wherein the cytosine is unmethylated, and wherein the nucleic acid moieties are 3-100 bases in length;

wherein the administration of the composition results in long term disease modification of asthma, wherein the long term disease modification is determined by the reduction of one or more asthma symptoms for a period of at least 3 weeks following administration of the last dose of CIC, and wherein the composition is administered at least 5 times.

16. The method of claim 15 wherein the multiple administrations occur on a weekly basis.

17. The method of claim 15 wherein the composition is administered at least 8 times.

18. The method of claim 15 wherein the multiple administration of the composition comprising ISS occurs every two weeks.

19. The method of claim 15 wherein the modification lasts at least 8 weeks after the last administration of the composition comprising CIC.

20. The method of claim 15 wherein the long term disease modification lasts at least 13 weeks after the last administration of the composition comprising CIC.

21. The method of claim 15 wherein the long term disease modification is a decrease of Th2 response in the individual.

22. The method of claim 21 wherein the decrease of Th2 response in the individual is a decrease of any one of the cytokines selected from the group consisting of IL-4, IL-5, IL-10, and IL-13.

23. The method of claim 21 wherein the decrease of Th2 response in an individual is a decrease in eosinophil infiltration in the airways.

24. The method of claim 15 wherein the treatment results in long term disease modification of asthma wherein the asthma is allergic asthma.

25. The method of claim 15 wherein the CIC comprises phosphorothioate linkages.

26. The method of claim 15 wherein at least one nucleic acid moiety comprises the sequence 5'-TCG-3'.

27. The method of claim 1 wherein the ISS is unconjugated ISS and is greater than 10 bases or base pairs and less than 200 bases or base pairs.

28. The method of claim 1 wherein the ISS is unconjugated ISS and is greater than 10 bases or base pairs and less than 100 bases or base pairs.

* * * * *

UNITED STATES PATENT AND TRADEMARK OFFICE
CERTIFICATE OF CORRECTION

| | | |
|---|---|---|
| PATENT NO. | : 8,252,757 B2 | Page 1 of 4 |
| APPLICATION NO. | : 11/938192 | |
| DATED | : August 28, 2012 | |
| INVENTOR(S) | : Edith M. Hessel et al. | |

It is certified that error appears in the above-identified patent and that said Letters Patent is hereby corrected as shown below:

Title Page, Item (56) under "OTHER PUBLICATIONS", in column 2, line 6, Delete "Oligonucletoides" and insert -- Oligonucleotides --, therefor.

On Title page 2, Item (56) under "OTHER PUBLICATIONS", in column 1, line 16, Delete "Administation" and insert -- Administration --, therefor.

On Title page 2, Item (56) under "OTHER PUBLICATIONS", in column 1, line 49, Delete "etl" and insert -- et --, therefor.

On Title page 2, Item (56) under "OTHER PUBLICATIONS", in column 2, line 27, Delete "Studay,"" and insert -- Study," --, therefor.

On Title page 3, Item (56) under "OTHER PUBLICATIONS", in column 1, line 1, Delete "Oliqonucleotide" and insert -- Oligonucleotide --, therefor.

On Title page 3, Item (56) under "OTHER PUBLICATIONS", in column 2, line 13, Delete "Invloved" and insert -- Involved --, therefor.

On Title page 3, Item (56) under "OTHER PUBLICATIONS", in column 2, line 61, Delete "Ctyptomeria" and insert -- Cryptomeria --, therefor.

On Title page 4, Item (56) under "OTHER PUBLICATIONS", in column 1, line 29, Delete "Iummunol." and insert -- Immunol. --, therefor.

On Title page 4, Item (56) under "OTHER PUBLICATIONS", in column 2, line 8, Delete "Phospholiapse" and insert -- Phospholipase --, therefor.

On Title page 4, Item (56) under "OTHER PUBLICATIONS", in column 2, line 20, Delete "(Ph1" and insert -- (Phl --, therefor.

Signed and Sealed this
First Day of July, 2014

Michelle K. Lee
*Deputy Director of the United States Patent and Trademark Office*

CERTIFICATE OF CORRECTION (continued)
U.S. Pat. No. 8,252,757 B2

On Title page 4, Item (56) under "OTHER PUBLICATIONS", in column 2, line 39, Delete "Mechanims:" and insert -- Mechanism: --, therefor.

On Title page 5, Item (56) under "OTHER PUBLICATIONS", in column 1, line 9, Delete "Immunolgy" and insert -- Immunology --, therefor.

In the Specification

In column 3, line 47, Delete "jointly" and insert -- (jointly --, therefor.

In column 3, line 61, Delete "Verlags gesellschaft" and insert -- Verlagsgesellschaft --, therefor.

In column 6, line 30, Delete "(Nw)y" and insert -- (Nq))y --, therefor.

In column 6, line 47, Delete "(Nq)y" and insert -- (Nq))y --, therefor.

In column 7, line 10, Delete "(Nq)y" and insert -- (Nq))y --, therefor.

In column 7, line 19, Delete "CGVX3'" and insert -- CGX4'X3' --, therefor.

In column 7, line 32, Delete "$X^{2'}$" and insert -- $X_2'$ --, therefor.

In column 7, line 41, Delete "(Nq)y" and insert -- (Nq))y --, therefor.

In column 7, line 58, Delete "(Nq)y" and insert -- (Nq))y --, therefor.

In column 8, line 2, Delete "X1'(CG" and insert -- X1'CG --, therefor.

In column 8, line 35, Delete "(Nq)y" and insert -- (Nq))y --, therefor.

In column 8, line 57, Delete "(Nq)y" and insert -- (Nq))y --, therefor.

In column 9, line 1, Delete "((X1" and insert -- (X1 --, therefor.

In column 9, line 21, Delete "(Nq)y" and insert -- (Nq))y --, therefor.

In column 9, line 44, Delete "(Nq)y" and insert -- (Nq))y --, therefor.

In column 14, line 14, Delete "2'-0-" and insert -- 2'-O- --, therefor.

In column 14, line 46, Delete "oxopyrolo" and insert -- oxopyrrolo --, therefor.

In column 16, line 45, Delete "β-lactoglobin" and insert -- β-lactoglobulin --, therefor.

CERTIFICATE OF CORRECTION (continued)
U.S. Pat. No. 8,252,757 B2

In column 16, line 45, Delete "Selot" and insert -- Selo --, therefor.

In TABLE 1, column 17-18, line 49, Delete "Dermatis," and insert -- Dermatitis, --, therefor.

In TABLE 1, column 17-18, line 50, Delete "topomyosin" and insert -- tropomyosin --, therefor.

In TABLE 1, column 19-20, line 32, Delete "Penicillinium" and insert -- Penicillium --, therefor.

In column 19, line 38, Delete "Hemophilus influenza," and insert -- Haemophilus influenzae --, therefor.

In column 25, line 43, Delete "Dematol." and insert -- Dermatol. --, therefor.

In column 26, line 17, Delete "tetraminobenzene," and insert -- tetraaminobenzene, --, therefor.

In column 26, line 17-18, Delete "heptaminobetacyclodextrin," and insert -- heptaaminobetacyclodextrin, --, therefor.

In column 26, line 18, Delete "tetraminopentaerythritol," and insert -- tetraaminopentaerythritol, --, therefor.

In column 26, line 67, Delete "maleiamide," and insert -- maleimide, --, therefor.

In column 27, line 60-61, Delete "polyisohexlcyanoacrylate" and insert -- polyisohexylcyanoacrylate --, therefor.

In column 28, line 41, Delete "0.9-1.6 m." and insert -- 0.9-1.6 μm. --, therefor.

In column 29, line 22, Delete "polyvinylpirrolidone" and insert -- polyvinylpyrrolidone --, therefor.

In column 36, line 1, Delete "alklylammonium" and insert -- alkylammonium --, therefor.

In column 36, line 2, Delete "tetradecyltrimtheylammonia" and insert -- tetradecyltrimethylammonia --, therefor.

In column 36, line 3, Delete "tetradecyltrimtheylammonium" and insert -- tetradecyltrimethylammonium --, therefor.

In column 37, line 11, Delete "0.2-0.4, um" and insert -- 0.2-0.4 μm, --, therefor.

In column 38, line 2, Delete "to a the" and insert -- to the --, therefor.

In column 38, line 58-59, Delete "adenoassociated" and insert -- adeno-associated --, therefor.

In column 39, line 58, Delete "keritinolytic" and insert -- keratolytic --, therefor.

CERTIFICATE OF CORRECTION (continued)
U.S. Pat. No. 8,252,757 B2

In column 41, line 64-65, Delete "hyper responsiveness," and insert -- hyperresponsiveness, --, therefor.

In column 43, line 45, Delete "isofloraine" and insert -- isoflurane --, therefor.

In column 45, line 40, Delete "isofloraine" and insert -- isoflurane --, therefor.

In column 47, line 2, Delete "isofloraine" and insert -- isoflurane --, therefor.

In column 48, line 41, Delete "isofloraine" and insert -- isoflurane --, therefor.

In column 48, line 54, Delete "IL-113," and insert -- IL-13, --, therefor.

In column 48, line 61, Delete "IL-113," and insert -- IL-13, --, therefor.

In the Claims

In column 83, line 50, In Claim 13, Delete "(Nq)y" and insert -- (Nq))y --, therefor.